(12) United States Patent
Cooper et al.

(10) Patent No.: US 11,883,287 B2
(45) Date of Patent: *Jan. 30, 2024

(54) STEERABLE RAIL DELIVERY SYSTEM

(71) Applicant: Edwards Lifesciences Corporation, Irvine, CA (US)

(72) Inventors: Alexander H. Cooper, Costa Mesa, CA (US); David Robert Landon, Costa Mesa, CA (US); Kevin M. Stewart, Corona, CA (US); Garrett Dallas Johnson, Costa Mesa, CA (US); Glen T. Rabito, Lake Forest, CA (US); Tarannum Ishaq Gutierrez, Ladera Ranch, CA (US); Hiroshi Okabe, Costa Mesa, CA (US); Ramon Aguilar, Jr., Corona, CA (US); Jesse Robert Edwards, Ladera Ranch, CA (US); Taylor Jacob Scheinblum, Newport Beach, CA (US); Patrick Chow, San Marino, CA (US); Julio Cesar Sanchez, Garden Grove, CA (US); Hieu Minh Luong, Westminster, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 675 days.

This patent is subject to a terminal disclaimer.

(21) Appl. No.: 17/071,745

(22) Filed: Oct. 15, 2020

(65) Prior Publication Data

US 2021/0022863 A1 Jan. 28, 2021

Related U.S. Application Data

(63) Continuation of application No. 16/028,172, filed on Jul. 5, 2018, now Pat. No. 10,813,757.

(Continued)

(51) Int. Cl.
  *A61F 2/24* (2006.01)
  *A61M 25/00* (2006.01)
  (Continued)

(52) U.S. Cl.
  CPC ............ *A61F 2/2436* (2013.01); *A61F 2/243* (2013.01); *A61F 2/2439* (2013.01);
  (Continued)

(58) Field of Classification Search
  None
  See application file for complete search history.

(56) References Cited

U.S. PATENT DOCUMENTS

| 3,657,744 A | 4/1972 | Ersek |
| 3,671,979 A | 6/1972 | Moulopoulos |

(Continued)

FOREIGN PATENT DOCUMENTS

| CA | 2304325 A1 | 10/2000 |
| CA | 2827556 A1 | 7/2012 |

(Continued)

OTHER PUBLICATIONS

Bavaria, Joseph E. M.D. et al.: "Transcatheter Mitral Valve Implantation: The Future Gold Standard for MR?," Applicant requests the Examiner to consider this reference to be prior art as of Dec. of 2010.

(Continued)

*Primary Examiner* — Shaun L David
(74) *Attorney, Agent, or Firm* — Knobbe Martens Olson & Bear LLP

(57) ABSTRACT

Devices, systems and methods are described herein to provide improved steerability for delivering a prosthesis to a body location, for example, for delivering a replacement mitral valve to a native mitral valve location. The steerable delivery system can contain a steerable rail configured for (Continued)

multi-plane bending to direct a distal end of the delivery system.

20 Claims, 48 Drawing Sheets

Related U.S. Application Data

(60) Provisional application No. 62/635,421, filed on Feb. 26, 2018, provisional application No. 62/529,394, filed on Jul. 6, 2017.

(51) Int. Cl.
*A61M 25/01* (2006.01)
*A61F 2/95* (2013.01)

(52) U.S. Cl.
CPC ...... *A61M 25/005* (2013.01); *A61M 25/0054* (2013.01); *A61M 25/0147* (2013.01); *A61F 2/2418* (2013.01); *A61F 2/9517* (2020.05)

(56) References Cited

U.S. PATENT DOCUMENTS

| | | |
|---|---|---|
| 3,739,402 A | 6/1973 | Cooley et al. |
| 4,056,854 A | 11/1977 | Boretos et al. |
| 4,079,468 A | 3/1978 | Liotta et al. |
| 4,204,283 A | 5/1980 | Bellhouse et al. |
| 4,222,126 A | 9/1980 | Boretos et al. |
| 4,265,694 A | 5/1981 | Boretos et al. |
| 4,339,831 A | 7/1982 | Johnson |
| 4,340,977 A | 7/1982 | Brownlee et al. |
| 4,470,157 A | 9/1984 | Love |
| 4,477,930 A | 10/1984 | Totten et al. |
| 4,490,859 A | 1/1985 | Black et al. |
| 4,553,545 A | 11/1985 | Maass et al. |
| 4,777,951 A | 10/1988 | Cribier et al. |
| 4,865,600 A | 9/1989 | Carpentier et al. |
| 4,994,077 A | 2/1991 | Dobben |
| 5,326,371 A | 7/1994 | Love et al. |
| 5,332,402 A | 7/1994 | Teitelbaum |
| 5,370,685 A | 12/1994 | Stevens |
| 5,411,552 A | 5/1995 | Andersen et al. |
| 5,415,667 A | 5/1995 | Frater |
| 5,545,214 A | 8/1996 | Stevens |
| 5,554,185 A | 9/1996 | Block et al. |
| 5,573,520 A | 11/1996 | Schwartz et al. |
| 5,697,382 A | 12/1997 | Love et al. |
| 5,840,081 A | 11/1998 | Andersen et al. |
| 5,855,601 A | 1/1999 | Bessler et al. |
| 5,944,690 A | 8/1999 | Falwell et al. |
| 5,957,949 A | 9/1999 | Leonhardt et al. |
| 6,086,612 A | 7/2000 | Jansen |
| 6,113,631 A | 9/2000 | Jansen |
| 6,168,614 B1 | 1/2001 | Andersen et al. |
| 6,251,093 B1 | 6/2001 | Valley et al. |
| 6,312,465 B1 | 11/2001 | Griffin et al. |
| 6,358,277 B1 | 3/2002 | Duran |
| 6,440,164 B1 | 8/2002 | Di Matteo et al. |
| 6,458,153 B1 | 10/2002 | Bailey et al. |
| 6,482,228 B1 | 11/2002 | Norred |
| 6,527,800 B1 | 3/2003 | McGuckin, Jr. et al. |
| 6,582,462 B1 | 6/2003 | Andersen et al. |
| 6,610,088 B1 | 8/2003 | Gabbay |
| 6,622,367 B1 | 9/2003 | Bolduc et al. |
| 6,629,534 B1 | 10/2003 | St. Goar et al. |
| 6,652,578 B2 | 11/2003 | Bailey et al. |
| 6,676,698 B2 | 1/2004 | McGuckin, Jr. et al. |
| 6,695,878 B2 | 2/2004 | McGuckin, Jr. et al. |
| 6,712,836 B1 | 3/2004 | Berg et al. |
| 6,716,207 B2 | 4/2004 | Farnholtz |
| 6,729,356 B1 | 5/2004 | Baker et al. |
| 6,730,118 B2 | 5/2004 | Spenser et al. |
| 6,746,422 B1 | 6/2004 | Noriega et al. |
| 6,749,560 B1 | 6/2004 | Konstorum et al. |
| 6,767,362 B2 | 7/2004 | Schreck |
| 6,780,200 B2 | 8/2004 | Jansen |
| 6,790,229 B1 | 9/2004 | Berreklouw |
| 6,790,230 B2 | 9/2004 | Beyersdorf et al. |
| 6,875,231 B2 | 4/2005 | Anduiza et al. |
| 6,893,460 B2 | 5/2005 | Spenser et al. |
| 6,908,481 B2 | 6/2005 | Cribier |
| 7,018,406 B2 | 3/2006 | Seguin et al. |
| 7,186,265 B2 | 3/2007 | Sharkawy et al. |
| 7,192,440 B2 | 3/2007 | Andreas et al. |
| 7,198,646 B2 | 4/2007 | Figulla et al. |
| 7,201,772 B2 | 4/2007 | Schwammenthal et al. |
| 7,276,078 B2 | 10/2007 | Spenser et al. |
| 7,329,278 B2 | 2/2008 | Seguin et al. |
| 7,381,219 B2 | 6/2008 | Salahieh et al. |
| 7,393,360 B2 | 7/2008 | Spenser et al. |
| 7,429,269 B2 | 9/2008 | Schwammenthal et al. |
| 7,442,204 B2 | 10/2008 | Schwammenthal et al. |
| 7,445,631 B2 | 11/2008 | Salahieh et al. |
| 7,462,191 B2 | 12/2008 | Spenser et al. |
| 7,510,575 B2 | 3/2009 | Spenser et al. |
| 7,524,330 B2 | 4/2009 | Berreklouw |
| 7,553,324 B2 | 6/2009 | Andreas et al. |
| 7,585,321 B2 | 9/2009 | Cribier |
| 7,618,446 B2 | 11/2009 | Andersen et al. |
| 7,621,948 B2 | 11/2009 | Herrmann et al. |
| 7,628,805 B2 | 12/2009 | Spenser et al. |
| 7,748,389 B2 | 7/2010 | Salahieh et al. |
| 7,753,949 B2 | 7/2010 | Lamphere et al. |
| 7,803,185 B2 | 9/2010 | Gabbay |
| 7,806,919 B2 | 10/2010 | Bloom et al. |
| 7,815,673 B2 | 10/2010 | Bloom et al. |
| 7,824,443 B2 | 11/2010 | Salahieh et al. |
| 7,892,281 B2 | 2/2011 | Seguin et al. |
| 7,914,569 B2 | 3/2011 | Nguyen et al. |
| 7,947,075 B2 | 5/2011 | Goetz et al. |
| 7,959,672 B2 | 6/2011 | Salahieh et al. |
| 7,972,378 B2 | 7/2011 | Tabor et al. |
| 7,981,151 B2 | 7/2011 | Rowe |
| 7,993,392 B2 | 8/2011 | Righini et al. |
| 8,016,877 B2 | 9/2011 | Seguin et al. |
| 8,048,153 B2 | 11/2011 | Salahieh et al. |
| 8,052,750 B2 | 11/2011 | Tuval et al. |
| 8,070,800 B2 | 12/2011 | Lock et al. |
| 8,070,802 B2 | 12/2011 | Lamphere et al. |
| 8,075,615 B2 | 12/2011 | Eberhardt et al. |
| 8,080,054 B2 | 12/2011 | Rowe |
| 8,092,520 B2 | 1/2012 | Quadri |
| 8,109,996 B2 | 2/2012 | Stacchino et al. |
| 8,118,866 B2 | 2/2012 | Herrmann et al. |
| 8,136,218 B2 | 3/2012 | Millwee et al. |
| 8,137,398 B2 | 3/2012 | Tuval et al. |
| 8,157,852 B2 | 4/2012 | Bloom et al. |
| 8,167,934 B2 | 5/2012 | Styrc et al. |
| 8,182,528 B2 | 5/2012 | Salahieh et al. |
| 8,182,530 B2 | 5/2012 | Huber |
| 8,216,301 B2 | 7/2012 | Bonhoeffer et al. |
| 8,219,229 B2 | 7/2012 | Cao et al. |
| 8,220,121 B2 | 7/2012 | Hendriksen et al. |
| 8,221,493 B2 | 7/2012 | Boyle et al. |
| 8,226,710 B2 | 7/2012 | Nguyen et al. |
| 8,236,045 B2 | 8/2012 | Benichou et al. |
| 8,246,675 B2 | 8/2012 | Zegdi |
| 8,246,678 B2 | 8/2012 | Salahieh et al. |
| 8,252,051 B2 | 8/2012 | Chau et al. |
| 8,252,052 B2 | 8/2012 | Salahieh et al. |
| 8,287,584 B2 | 10/2012 | Salahieh et al. |
| 8,303,653 B2 | 11/2012 | Bonhoeffer et al. |
| 8,313,525 B2 | 11/2012 | Tuval et al. |
| 8,323,335 B2 | 12/2012 | Rowe et al. |
| 8,353,953 B2 | 1/2013 | Giannetti et al. |
| 8,403,983 B2 | 3/2013 | Quadri et al. |
| 8,414,644 B2 | 4/2013 | Quadri et al. |
| 8,414,645 B2 | 4/2013 | Dwork et al. |
| 8,444,689 B2 | 5/2013 | Zhang |
| 8,449,599 B2 | 5/2013 | Chau et al. |
| 8,454,685 B2 | 6/2013 | Hariton et al. |
| 8,460,368 B2 | 6/2013 | Taylor et al. |

(56) References Cited

U.S. PATENT DOCUMENTS

| | | | |
|---|---|---|---|
| 8,470,023 B2 | 6/2013 | Eidenschink et al. |
| 8,475,521 B2 | 7/2013 | Suri et al. |
| 8,475,523 B2 | 7/2013 | Duffy |
| 8,479,380 B2 | 7/2013 | Malewicz et al. |
| 8,486,137 B2 | 7/2013 | Suri et al. |
| 8,491,650 B2 | 7/2013 | Wiemeyer et al. |
| 8,500,733 B2 | 8/2013 | Watson |
| 8,500,798 B2 | 8/2013 | Rowe et al. |
| 8,511,244 B2 | 8/2013 | Holecek et al. |
| 8,512,401 B2 | 8/2013 | Murray, III et al. |
| 8,518,096 B2 | 8/2013 | Nelson |
| 8,518,106 B2 | 8/2013 | Duffy et al. |
| 8,562,663 B2 | 10/2013 | Mearns et al. |
| 8,579,963 B2 | 11/2013 | Tabor |
| 8,579,964 B2 | 11/2013 | Lane et al. |
| 8,579,965 B2 | 11/2013 | Bonhoeffer et al. |
| 8,585,755 B2 | 11/2013 | Chau et al. |
| 8,585,756 B2 | 11/2013 | Bonhoeffer et al. |
| 8,591,570 B2 | 11/2013 | Revuelta et al. |
| 8,597,348 B2 | 12/2013 | Rowe et al. |
| 8,617,236 B2 | 12/2013 | Paul et al. |
| 8,640,521 B2 | 2/2014 | Righini et al. |
| 8,647,381 B2 | 2/2014 | Essinger et al. |
| 8,652,145 B2 | 2/2014 | Maimon et al. |
| 8,652,201 B2 | 2/2014 | Oberti et al. |
| 8,652,202 B2 | 2/2014 | Alon et al. |
| 8,652,203 B2 | 2/2014 | Quadri et al. |
| 8,668,733 B2 | 3/2014 | Haug et al. |
| 8,673,000 B2 | 3/2014 | Tabor et al. |
| 8,679,174 B2 | 3/2014 | Ottma et al. |
| 8,679,404 B2 | 3/2014 | Liburd et al. |
| 8,685,086 B2 | 4/2014 | Navia et al. |
| 8,721,708 B2 | 5/2014 | Seguin et al. |
| 8,721,714 B2 | 5/2014 | Kelley |
| 8,728,154 B2 | 5/2014 | Alkhatib |
| 8,728,155 B2 | 5/2014 | Montorfano et al. |
| 8,740,974 B2 | 6/2014 | Lambrecht et al. |
| 8,740,976 B2 | 6/2014 | Tran et al. |
| 8,747,458 B2 | 6/2014 | Tuval et al. |
| 8,747,459 B2 | 6/2014 | Nguyen et al. |
| 8,747,460 B2 | 6/2014 | Tuval et al. |
| 8,758,432 B2 | 6/2014 | Solem |
| 8,764,818 B2 | 7/2014 | Gregg |
| 8,771,344 B2 | 7/2014 | Tran et al. |
| 8,771,345 B2 | 7/2014 | Tuval et al. |
| 8,771,346 B2 | 7/2014 | Tuval et al. |
| 8,778,020 B2 | 7/2014 | Gregg et al. |
| 8,784,337 B2 | 7/2014 | Voeller et al. |
| 8,784,478 B2 | 7/2014 | Tuval et al. |
| 8,784,481 B2 | 7/2014 | Alkhatib et al. |
| 8,790,387 B2 | 7/2014 | Nguyen et al. |
| 8,795,356 B2 | 8/2014 | Quadri et al. |
| 8,795,357 B2 | 8/2014 | Yohanan et al. |
| 8,808,356 B2 | 8/2014 | Braido et al. |
| 8,828,078 B2 | 9/2014 | Salahieh et al. |
| 8,828,079 B2 | 9/2014 | Thielen et al. |
| 8,834,564 B2 | 9/2014 | Tuval et al. |
| 8,845,718 B2 | 9/2014 | Tuval et al. |
| 8,858,620 B2 | 10/2014 | Salahieh et al. |
| 8,870,948 B1 | 10/2014 | Erzberger et al. |
| 8,870,950 B2 | 10/2014 | Hacohen |
| 8,876,893 B2 | 11/2014 | Dwork et al. |
| 8,876,894 B2 | 11/2014 | Tuval et al. |
| 8,876,895 B2 | 11/2014 | Tuval et al. |
| 8,911,455 B2 | 12/2014 | Quadri et al. |
| 8,926,693 B2 | 1/2015 | Duffy et al. |
| 8,926,694 B2 | 1/2015 | Costello |
| 8,939,960 B2 | 1/2015 | Rosenman et al. |
| 8,945,209 B2 | 2/2015 | Bonyuet et al. |
| 8,951,299 B2 | 2/2015 | Paul et al. |
| 8,961,593 B2 | 2/2015 | Bonhoeffer et al. |
| 8,961,595 B2 | 2/2015 | Alkhatib |
| 8,974,524 B2 | 3/2015 | Yeung et al. |
| 8,979,922 B2 | 3/2015 | Jayasinghe et al. |
| 8,986,372 B2 | 3/2015 | Murry, III et al. |
| 8,986,375 B2 | 3/2015 | Garde et al. |
| 8,992,608 B2 | 3/2015 | Haug et al. |
| 8,998,979 B2 | 4/2015 | Seguin et al. |
| 8,998,980 B2 | 4/2015 | Shipley et al. |
| 9,005,273 B2 | 4/2015 | Salahieh et al. |
| 9,011,521 B2 | 4/2015 | Haug et al. |
| 9,011,523 B2 | 4/2015 | Seguin |
| 9,011,524 B2 | 4/2015 | Eberhardt |
| 9,028,545 B2 | 5/2015 | Taylor |
| 9,034,032 B2 | 5/2015 | McLean et al. |
| 9,034,033 B2 | 5/2015 | McLean et al. |
| 9,039,757 B2 | 5/2015 | McLean et al. |
| 9,055,937 B2 | 6/2015 | Rowe et al. |
| 9,066,801 B2 | 6/2015 | Kovalsky et al. |
| 9,078,749 B2 | 7/2015 | Lutter et al. |
| 9,078,751 B2 | 7/2015 | Naor |
| 9,084,676 B2 | 7/2015 | Chau et al. |
| 9,125,738 B2 | 9/2015 | Figulla et al. |
| 9,138,312 B2 | 9/2015 | Tuval et al. |
| 9,161,834 B2 | 10/2015 | Taylor et al. |
| 9,173,737 B2 | 11/2015 | Hill et al. |
| 9,180,004 B2 | 11/2015 | Alkhatib |
| 9,186,249 B2 | 11/2015 | Rolando et al. |
| 9,220,594 B2 | 12/2015 | Braido et al. |
| 9,241,790 B2 | 1/2016 | Lane et al. |
| 9,248,014 B2 | 2/2016 | Lane et al. |
| 9,277,990 B2 | 3/2016 | Klima et al. |
| 9,277,993 B2 | 3/2016 | Gamarra et al. |
| 9,289,291 B2 | 3/2016 | Gorman, III et al. |
| 9,289,296 B2 | 3/2016 | Braido et al. |
| 9,295,551 B2 | 3/2016 | Straubinger et al. |
| 9,326,815 B2 | 5/2016 | Watson |
| 9,331,328 B2 | 5/2016 | Eberhardt et al. |
| 9,339,382 B2 | 5/2016 | Tabor et al. |
| 9,351,831 B2 | 5/2016 | Braido et al. |
| 9,351,832 B2 | 5/2016 | Braido et al. |
| 9,364,321 B2 | 6/2016 | Alkhatib et al. |
| 9,445,897 B2 | 9/2016 | Bishop et al. |
| 9,456,877 B2 | 10/2016 | Weitzner et al. |
| 9,681,968 B2 | 6/2017 | Goetz et al. |
| 9,700,329 B2 | 7/2017 | Metzger et al. |
| 9,700,411 B2 | 7/2017 | Klima et al. |
| 9,795,479 B2 | 10/2017 | Lim et al. |
| 9,833,313 B2 | 12/2017 | Board et al. |
| 9,861,473 B2 | 1/2018 | Lafontaine |
| 9,861,476 B2 | 1/2018 | Salahieh et al. |
| 9,861,477 B2 | 1/2018 | Backus et al. |
| 9,867,698 B2 | 1/2018 | Kovalsky et al. |
| 9,877,830 B2 | 1/2018 | Lim et al. |
| 9,889,029 B2 | 2/2018 | Li et al. |
| 9,895,225 B2 | 2/2018 | Rolando et al. |
| 9,925,045 B2 | 3/2018 | Creaven et al. |
| 10,065,015 B2 | 9/2018 | Leeflang et al. |
| 10,076,638 B2 | 9/2018 | Tran et al. |
| 2001/0007956 A1 | 7/2001 | Letac et al. |
| 2002/0016623 A1 | 2/2002 | Kula et al. |
| 2002/0032481 A1 | 3/2002 | Gabbay |
| 2002/0045929 A1 | 4/2002 | Diaz |
| 2002/0052644 A1 | 5/2002 | Shaolian et al. |
| 2002/0072710 A1 | 6/2002 | Stewart et al. |
| 2003/0105517 A1 | 6/2003 | White et al. |
| 2003/0120333 A1 | 6/2003 | Ouriel et al. |
| 2003/0130729 A1 | 7/2003 | Paniagua et al. |
| 2003/0176914 A1 | 9/2003 | Rabkin et al. |
| 2003/0199971 A1 | 10/2003 | Tower et al. |
| 2003/0220683 A1 | 11/2003 | Minasian et al. |
| 2004/0117009 A1 | 6/2004 | Cali et al. |
| 2004/0133273 A1 | 7/2004 | Cox |
| 2004/0186561 A1 | 9/2004 | McGuckin et al. |
| 2004/0193193 A1 | 9/2004 | Laufer et al. |
| 2004/0210304 A1 | 10/2004 | Seguin et al. |
| 2004/0210307 A1 | 10/2004 | Khairkhahan |
| 2004/0215325 A1 | 10/2004 | Penn et al. |
| 2004/0225353 A1 | 11/2004 | McGuckin et al. |
| 2004/0236411 A1 | 11/2004 | Sarac et al. |
| 2005/0033398 A1 | 2/2005 | Seguin |
| 2005/0043682 A1 | 2/2005 | Kucklick et al. |
| 2005/0070844 A1 | 3/2005 | Chow et al. |
| 2005/0075727 A1 | 4/2005 | Wheatley |

(56) References Cited

U.S. PATENT DOCUMENTS

| | | |
|---|---|---|
| 2005/0090887 A1 | 4/2005 | Pryor |
| 2005/0090890 A1 | 4/2005 | Wu et al. |
| 2005/0096738 A1 | 5/2005 | Cali et al. |
| 2005/0107872 A1 | 5/2005 | Mensah et al. |
| 2005/0137682 A1 | 6/2005 | Justino |
| 2005/0137686 A1 | 6/2005 | Salahieh et al. |
| 2005/0137687 A1 | 6/2005 | Salahieh et al. |
| 2005/0137691 A1 | 6/2005 | Salahieh et al. |
| 2005/0137693 A1 | 6/2005 | Haug et al. |
| 2005/0159811 A1 | 7/2005 | Lane |
| 2005/0182486 A1 | 8/2005 | Gabbay |
| 2005/0216079 A1 | 9/2005 | MaCoviak |
| 2005/0234546 A1 | 10/2005 | Nugent et al. |
| 2005/0283231 A1 | 12/2005 | Haug et al. |
| 2006/0020327 A1 | 1/2006 | Lashinski et al. |
| 2006/0052867 A1 | 3/2006 | Revuelta et al. |
| 2006/0058872 A1 | 3/2006 | Salahieh et al. |
| 2006/0095115 A1 | 5/2006 | Bladillah et al. |
| 2006/0100687 A1 | 5/2006 | Fahey et al. |
| 2006/0135961 A1* | 6/2006 | Rosenman ......... A61B 17/0057 604/95.04 |
| 2006/0135962 A1* | 6/2006 | Kick ................... A61M 29/02 606/191 |
| 2006/0173537 A1 | 8/2006 | Yang et al. |
| 2006/0195183 A1 | 8/2006 | Navia et al. |
| 2006/0212110 A1 | 9/2006 | Osborne et al. |
| 2006/0241745 A1 | 10/2006 | Solem |
| 2006/0259135 A1 | 11/2006 | Navia et al. |
| 2006/0265056 A1 | 11/2006 | Nguyen et al. |
| 2006/0287717 A1 | 12/2006 | Rowe et al. |
| 2006/0293745 A1 | 12/2006 | Carpentier et al. |
| 2007/0005131 A1* | 1/2007 | Taylor ................. A61F 2/2427 623/2.11 |
| 2007/0010876 A1 | 1/2007 | Salahieh et al. |
| 2007/0043435 A1 | 2/2007 | Seguin et al. |
| 2007/0050021 A1 | 3/2007 | Johnson |
| 2007/0100432 A1 | 5/2007 | Case et al. |
| 2007/0129794 A1 | 6/2007 | Realyvasquez |
| 2007/0142906 A1 | 6/2007 | Figulla et al. |
| 2007/0213813 A1 | 9/2007 | Von Segesser et al. |
| 2007/0255394 A1 | 11/2007 | Ryan |
| 2008/0021546 A1 | 1/2008 | Patz et al. |
| 2008/0065011 A1* | 3/2008 | Marchand ........... A61F 2/2436 604/103.05 |
| 2008/0071366 A1 | 3/2008 | Tuval et al. |
| 2008/0082164 A1 | 4/2008 | Friedman |
| 2008/0082165 A1 | 4/2008 | Wilson et al. |
| 2008/0097581 A1 | 4/2008 | Shanley |
| 2008/0147179 A1 | 6/2008 | Cai et al. |
| 2008/0147183 A1 | 6/2008 | Styrc |
| 2008/0161911 A1 | 7/2008 | Revuelta et al. |
| 2008/0177381 A1 | 7/2008 | Navia et al. |
| 2008/0183273 A1 | 7/2008 | Mesana et al. |
| 2008/0188928 A1* | 8/2008 | Salahieh ............ A61M 25/0054 623/2.11 |
| 2008/0208328 A1 | 8/2008 | Antocci et al. |
| 2008/0228254 A1 | 9/2008 | Ryan |
| 2008/0243081 A1* | 10/2008 | Nance ................ A61B 17/3439 604/164.03 |
| 2009/0005863 A1 | 1/2009 | Goetz et al. |
| 2009/0099554 A1* | 4/2009 | Forster ................. A61F 2/2427 606/1 |
| 2009/0138079 A1 | 5/2009 | Tuval et al. |
| 2009/0171456 A1 | 7/2009 | Kveen et al. |
| 2009/0182413 A1 | 7/2009 | Burkart et al. |
| 2009/0188964 A1 | 7/2009 | Orlov |
| 2009/0270972 A1 | 10/2009 | Lane |
| 2009/0276027 A1 | 11/2009 | Glynn |
| 2009/0276040 A1 | 11/2009 | Rowe et al. |
| 2009/0281618 A1 | 11/2009 | Hill et al. |
| 2009/0287296 A1 | 11/2009 | Manasse |
| 2009/0292350 A1 | 11/2009 | Eberhardt et al. |
| 2009/0306768 A1 | 12/2009 | Quadri |
| 2010/0049313 A1 | 2/2010 | Alon et al. |
| 2010/0069882 A1 | 3/2010 | Jennings et al. |
| 2010/0114305 A1 | 5/2010 | Kang et al. |
| 2010/0191326 A1 | 7/2010 | Alkhatib |
| 2010/0217382 A1 | 8/2010 | Chau et al. |
| 2010/0249894 A1 | 9/2010 | Oba et al. |
| 2010/0249911 A1 | 9/2010 | Alkhatib |
| 2010/0256723 A1 | 10/2010 | Murray |
| 2010/0305685 A1 | 12/2010 | Millwee et al. |
| 2011/0004296 A1 | 1/2011 | Utter et al. |
| 2011/0015729 A1* | 1/2011 | Jimenez ............ A61M 25/0136 623/2.11 |
| 2011/0029067 A1 | 2/2011 | McGuckin, Jr. et al. |
| 2011/0098804 A1* | 4/2011 | Yeung ................... A61F 2/2412 623/2.1 |
| 2011/0208297 A1 | 8/2011 | Tuval et al. |
| 2011/0208298 A1 | 8/2011 | Tuval et al. |
| 2011/0224785 A1 | 9/2011 | Hacohen |
| 2011/0264196 A1 | 10/2011 | Savage et al. |
| 2011/0313515 A1 | 12/2011 | Quadri et al. |
| 2012/0016192 A1 | 1/2012 | Jansen et al. |
| 2012/0022639 A1 | 1/2012 | Hacohen et al. |
| 2012/0041550 A1 | 2/2012 | Salahieh et al. |
| 2012/0059454 A1 | 3/2012 | Millwee et al. |
| 2012/0078351 A1* | 3/2012 | Klima ............... A61B 17/00234 623/2.11 |
| 2012/0078360 A1 | 3/2012 | Rafiee |
| 2012/0101571 A1 | 4/2012 | Thambar et al. |
| 2012/0101572 A1 | 4/2012 | Kovalsky et al. |
| 2012/0123529 A1 | 5/2012 | Levi et al. |
| 2012/0172920 A1* | 7/2012 | Fifer ...................... A61F 2/012 606/200 |
| 2012/0215303 A1 | 8/2012 | Quadri et al. |
| 2012/0239142 A1* | 9/2012 | Liu ....................... A61F 2/2436 623/2.11 |
| 2012/0253131 A1 | 10/2012 | Malkowski et al. |
| 2012/0271398 A1 | 10/2012 | Essinger et al. |
| 2012/0290062 A1 | 11/2012 | McNamara et al. |
| 2012/0310328 A1 | 12/2012 | Olson et al. |
| 2013/0006294 A1 | 1/2013 | Kashkarov et al. |
| 2013/0030519 A1 | 1/2013 | Tran et al. |
| 2013/0030520 A1 | 1/2013 | Lee et al. |
| 2013/0035759 A1 | 2/2013 | Gross et al. |
| 2013/0053950 A1 | 2/2013 | Rowe et al. |
| 2013/0131788 A1 | 5/2013 | Quadri et al. |
| 2013/0144378 A1 | 6/2013 | Quadri et al. |
| 2013/0211508 A1 | 8/2013 | Lane et al. |
| 2013/0253635 A1 | 9/2013 | Straubinger et al. |
| 2013/0253642 A1 | 9/2013 | Brecker |
| 2013/0310928 A1 | 11/2013 | Morriss et al. |
| 2013/0331929 A1 | 12/2013 | Mitra et al. |
| 2013/0338766 A1 | 12/2013 | Hastings et al. |
| 2013/0345786 A1 | 12/2013 | Behan |
| 2014/0018912 A1 | 1/2014 | Delaloye et al. |
| 2014/0025163 A1 | 1/2014 | Padala et al. |
| 2014/0031922 A1 | 1/2014 | Duffy et al. |
| 2014/0039611 A1 | 2/2014 | Lane et al. |
| 2014/0052237 A1 | 2/2014 | Lane et al. |
| 2014/0052242 A1 | 2/2014 | Revuelta et al. |
| 2014/0088565 A1 | 3/2014 | Vongphakdy et al. |
| 2014/0100651 A1 | 4/2014 | Kheradvar et al. |
| 2014/0100653 A1 | 4/2014 | Savage et al. |
| 2014/0135909 A1 | 5/2014 | Carr et al. |
| 2014/0142694 A1 | 5/2014 | Tabor et al. |
| 2014/0163668 A1 | 6/2014 | Rafiee |
| 2014/0172077 A1 | 6/2014 | Bruchman et al. |
| 2014/0172083 A1 | 6/2014 | Bruchman et al. |
| 2014/0194981 A1 | 7/2014 | Menk et al. |
| 2014/0207231 A1 | 7/2014 | Hacohen et al. |
| 2014/0214153 A1 | 7/2014 | Ottma et al. |
| 2014/0214154 A1 | 7/2014 | Nguyen et al. |
| 2014/0214155 A1 | 7/2014 | Kelley |
| 2014/0214160 A1 | 7/2014 | Naor |
| 2014/0222136 A1 | 8/2014 | Geist et al. |
| 2014/0222139 A1 | 8/2014 | Nguyen et al. |
| 2014/0222142 A1 | 8/2014 | Kovalsky et al. |
| 2014/0230515 A1 | 8/2014 | Tuval et al. |
| 2014/0236288 A1 | 8/2014 | Lambrecht et al. |
| 2014/0257467 A1 | 9/2014 | Lane et al. |
| 2014/0277390 A1 | 9/2014 | Ratz et al. |

(56) References Cited

U.S. PATENT DOCUMENTS

| | | |
|---|---|---|
| 2014/0277402 A1 | 9/2014 | Essinger et al. |
| 2014/0277422 A1 | 9/2014 | Ratz et al. |
| 2014/0277427 A1 | 9/2014 | Ratz et al. |
| 2014/0296973 A1 | 10/2014 | Bergheim et al. |
| 2014/0296975 A1 | 10/2014 | Tegels et al. |
| 2014/0303719 A1 | 10/2014 | Cox et al. |
| 2014/0309661 A1* | 10/2014 | Sheps ............... A61F 2/2427 606/130 |
| 2014/0309728 A1 | 10/2014 | Dehdashtian et al. |
| 2014/0309732 A1 | 10/2014 | Solem |
| 2014/0324160 A1 | 10/2014 | Benichou et al. |
| 2014/0324164 A1 | 10/2014 | Gross et al. |
| 2014/0330368 A1 | 11/2014 | Gloss et al. |
| 2014/0330371 A1 | 11/2014 | Gloss et al. |
| 2014/0330372 A1 | 11/2014 | Weston et al. |
| 2014/0336754 A1 | 11/2014 | Gurskis et al. |
| 2014/0343669 A1 | 11/2014 | Lane et al. |
| 2014/0343670 A1* | 11/2014 | Bakis ............... A61F 2/2436 623/2.11 |
| 2014/0343671 A1 | 11/2014 | Yohanan et al. |
| 2014/0350663 A1 | 11/2014 | Braido et al. |
| 2014/0350666 A1 | 11/2014 | Righini |
| 2014/0350668 A1 | 11/2014 | Delaloye et al. |
| 2014/0358223 A1 | 12/2014 | Rafiee et al. |
| 2014/0364939 A1 | 12/2014 | Deshmukh et al. |
| 2014/0364943 A1 | 12/2014 | Conklin |
| 2014/0371842 A1 | 12/2014 | Marquez et al. |
| 2014/0371844 A1 | 12/2014 | Dale et al. |
| 2014/0371845 A1 | 12/2014 | Tuval et al. |
| 2014/0371847 A1 | 12/2014 | Madrid et al. |
| 2014/0371848 A1 | 12/2014 | Murray, III et al. |
| 2014/0379067 A1 | 12/2014 | Nguyen et al. |
| 2014/0379068 A1 | 12/2014 | Thielen et al. |
| 2014/0379077 A1 | 12/2014 | Tuval et al. |
| 2015/0005863 A1 | 1/2015 | Para |
| 2015/0012085 A1 | 1/2015 | Salahieh et al. |
| 2015/0018938 A1 | 1/2015 | Von Segesser et al. |
| 2015/0018944 A1 | 1/2015 | O'Connell et al. |
| 2015/0039083 A1 | 2/2015 | Rafiee |
| 2015/0045880 A1 | 2/2015 | Hacohen |
| 2015/0073539 A1 | 3/2015 | Geiger et al. |
| 2015/0127093 A1 | 5/2015 | Hosmer et al. |
| 2015/0142103 A1 | 5/2015 | Vidlund |
| 2015/0148731 A1 | 5/2015 | Mcnamara et al. |
| 2015/0157457 A1 | 6/2015 | Hacohen |
| 2015/0157458 A1 | 6/2015 | Thambar et al. |
| 2015/0173897 A1 | 6/2015 | Raanani et al. |
| 2015/0196390 A1 | 7/2015 | Ma et al. |
| 2015/0209141 A1 | 7/2015 | Braido et al. |
| 2015/0238315 A1 | 8/2015 | Rabito et al. |
| 2015/0272737 A1 | 10/2015 | Dale et al. |
| 2015/0297346 A1 | 10/2015 | Duffy et al. |
| 2015/0327994 A1 | 11/2015 | Morriss et al. |
| 2015/0328000 A1 | 11/2015 | Ratz et al. |
| 2015/0328001 A1 | 11/2015 | McLean et al. |
| 2015/0328429 A1 | 11/2015 | Morriss et al. |
| 2015/0351903 A1 | 12/2015 | Morriss et al. |
| 2015/0351906 A1 | 12/2015 | Hammer et al. |
| 2015/0359629 A1 | 12/2015 | Ganesan et al. |
| 2016/0000591 A1 | 1/2016 | Lei et al. |
| 2016/0022961 A1 | 1/2016 | Rosenman et al. |
| 2016/0030169 A1 | 2/2016 | Shahriari |
| 2016/0030170 A1 | 2/2016 | Alkhatib et al. |
| 2016/0030171 A1 | 2/2016 | Quijano et al. |
| 2016/0038281 A1 | 2/2016 | Delaloye et al. |
| 2016/0045311 A1 | 2/2016 | McCann et al. |
| 2016/0074160 A1 | 3/2016 | Christianson et al. |
| 2016/0100746 A1 | 4/2016 | Okazaki et al. |
| 2016/0106537 A1 | 4/2016 | Christianson et al. |
| 2016/0113765 A1 | 4/2016 | Ganesan et al. |
| 2016/0113766 A1 | 4/2016 | Ganesan et al. |
| 2016/0113768 A1 | 4/2016 | Ganesan et al. |
| 2016/0143732 A1 | 5/2016 | Glimsdale |
| 2016/0158010 A1 | 6/2016 | Lim et al. |
| 2016/0158497 A1* | 6/2016 | Tran ............... A61M 25/0147 604/95.04 |
| 2016/0166383 A1 | 6/2016 | Lim et al. |
| 2016/0184097 A1 | 6/2016 | Lim et al. |
| 2016/0199206 A1 | 7/2016 | Lim et al. |
| 2016/0213473 A1 | 7/2016 | Hacohen et al. |
| 2016/0235529 A1 | 8/2016 | Ma et al. |
| 2016/0279386 A1 | 9/2016 | Dale et al. |
| 2016/0317301 A1* | 11/2016 | Quadri ............... A61F 2/2418 |
| 2017/0035567 A1* | 2/2017 | Duffy ............... A61M 25/0052 |
| 2017/0056171 A1* | 3/2017 | Cooper ............... A61M 25/0051 |
| 2017/0128197 A1* | 5/2017 | Bialas ............... A61F 2/2427 |
| 2017/0128209 A1 | 5/2017 | Morriss et al. |
| 2017/0165064 A1 | 6/2017 | Nyuli et al. |
| 2017/0216023 A1 | 8/2017 | Lane et al. |
| 2017/0216575 A1 | 8/2017 | Asleson et al. |
| 2017/0258614 A1 | 9/2017 | Griffin |
| 2017/0325954 A1 | 11/2017 | Perszyk |
| 2017/0348096 A1 | 12/2017 | Anderson |
| 2017/0367823 A1 | 12/2017 | Hariton et al. |
| 2018/0021129 A1 | 1/2018 | Peterson et al. |
| 2018/0028787 A1 | 2/2018 | McNiven et al. |
| 2018/0049873 A1 | 2/2018 | Manash et al. |
| 2018/0055629 A1 | 3/2018 | Oba et al. |
| 2018/0055636 A1 | 3/2018 | Valencia et al. |
| 2018/0085218 A1 | 3/2018 | Eidenschink |
| 2018/0110534 A1 | 4/2018 | Gavala et al. |
| 2019/0298557 A1 | 10/2019 | Murray, III |
| 2020/0345493 A1* | 11/2020 | Gregg ............... A61F 2/2436 |
| 2021/0154010 A1* | 5/2021 | Schneider ............... A61F 2/2418 |

FOREIGN PATENT DOCUMENTS

| | | |
|---|---|---|
| DE | 102006052564 B3 | 12/2007 |
| EP | 1171059 A1 | 1/2002 |
| EP | 1255510 A1 | 11/2002 |
| EP | 1259194 B1 | 11/2002 |
| EP | 1281375 A2 | 2/2003 |
| EP | 1369098 A1 | 12/2003 |
| EP | 1472996 A1 | 11/2004 |
| EP | 1734903 A1 | 12/2006 |
| EP | 1827558 A2 | 9/2007 |
| EP | 1239901 B1 | 10/2007 |
| EP | 2124826 A1 | 12/2009 |
| EP | 1935377 B1 | 3/2010 |
| EP | 2237746 A2 | 10/2010 |
| EP | 2238947 A2 | 10/2010 |
| EP | 2285317 A1 | 2/2011 |
| EP | 2308425 A1 | 4/2011 |
| EP | 2319458 A1 | 5/2011 |
| EP | 2398543 A1 | 12/2011 |
| EP | 2496182 A1 | 9/2012 |
| EP | 2566416 A1 | 3/2013 |
| EP | 2745805 A1 | 6/2014 |
| EP | 2749254 A1 | 7/2014 |
| EP | 2750630 A1 | 7/2014 |
| EP | 2777617 A1 | 9/2014 |
| EP | 2815723 A1 | 12/2014 |
| EP | 2815725 A1 | 12/2014 |
| EP | 2898858 A1 | 7/2015 |
| EP | 2967858 A2 | 1/2016 |
| EP | 2926766 B1 | 2/2016 |
| EP | 2985006 A1 | 2/2016 |
| EP | 2168536 B1 | 4/2016 |
| EP | 2262451 B1 | 5/2017 |
| EP | 3184083 A1 | 6/2017 |
| EP | 2446915 B1 | 1/2018 |
| EP | 3057541 B1 | 1/2018 |
| EP | 3037064 B1 | 3/2018 |
| EP | 3046511 B1 | 3/2018 |
| EP | 3142603 B1 | 3/2018 |
| EP | 3294220 A1 | 3/2018 |
| GB | 1264471 A | 2/1972 |
| GB | 1315844 A | 5/1973 |
| GB | 2398245 A | 8/2004 |
| JP | 2002540889 A | 12/2002 |
| JP | 2008541865 A | 11/2008 |
| WO | 9749355 A1 | 12/1997 |
| WO | 0061034 A1 | 10/2000 |

(56) References Cited

FOREIGN PATENT DOCUMENTS

| | | |
|---|---|---|
| WO | 03092554 A1 | 11/2003 |
| WO | 2004030569 A2 | 4/2004 |
| WO | 2005011534 A1 | 2/2005 |
| WO | 2006070372 A2 | 7/2006 |
| WO | 2006085225 A1 | 8/2006 |
| WO | 2006089236 A1 | 8/2006 |
| WO | 2006127765 A1 | 11/2006 |
| WO | 2007025028 A1 | 3/2007 |
| WO | 2007058857 A2 | 5/2007 |
| WO | 2007123658 A1 | 11/2007 |
| WO | 2008013915 A2 | 1/2008 |
| WO | 2008070797 A2 | 6/2008 |
| WO | 2008103722 A2 | 8/2008 |
| WO | 2008125153 A1 | 10/2008 |
| WO | 2008150529 A1 | 12/2008 |
| WO | 2009026563 A2 | 2/2009 |
| WO | 2009033469 A1 | 3/2009 |
| WO | 2009045331 A1 | 4/2009 |
| WO | 2009053497 A1 | 4/2009 |
| WO | 2009091509 A1 | 7/2009 |
| WO | 2009094500 A1 | 7/2009 |
| WO | 2009134701 A2 | 11/2009 |
| WO | 2010005524 A2 | 1/2010 |
| WO | 2010008549 A1 | 1/2010 |
| WO | 2010022138 A2 | 2/2010 |
| WO | 2010037141 A1 | 4/2010 |
| WO | 2010040009 A1 | 4/2010 |
| WO | 2010057262 A1 | 5/2010 |
| WO | 2011008538 A1 | 1/2011 |
| WO | 2011025945 A1 | 3/2011 |
| WO | 2011057087 A1 | 5/2011 |
| WO | 2011111047 A2 | 9/2011 |
| WO | 2011137531 A1 | 11/2011 |
| WO | 2012177942 A2 | 12/2012 |
| WO | 2013028387 A2 | 2/2013 |
| WO | 2013075215 A1 | 5/2013 |
| WO | 2013120181 A1 | 8/2013 |
| WO | 2013175468 A2 | 11/2013 |
| WO | 2013192305 A2 | 12/2013 |
| WO | 2014018432 A2 | 1/2014 |
| WO | 2014099655 A1 | 6/2014 |
| WO | 2014110019 A1 | 7/2014 |
| WO | 2014110171 A2 | 7/2014 |
| WO | 2014121042 A1 | 8/2014 |
| WO | 2014139545 A1 | 9/2014 |
| WO | 2014145338 A1 | 9/2014 |
| WO | 2014149865 A1 | 9/2014 |
| WO | 2014163706 A1 | 10/2014 |
| WO | 2014164364 A1 | 10/2014 |
| WO | 2014194178 A1 | 12/2014 |
| WO | 2014204807 A1 | 12/2014 |
| WO | 2014205064 A1 | 12/2014 |
| WO | 2014210124 A1 | 12/2014 |
| WO | 2015077274 A1 | 5/2015 |
| WO | 2015148241 A1 | 10/2015 |
| WO | 2016016899 A1 | 2/2016 |

OTHER PUBLICATIONS

Banai, Shmeul et al., The Journal of the American College of Cardiology, "Transapical Mitral Implantation of the Tiara Bioprosthesis Pre-Clinical Results," Feb. 2014, <http://interventions.onlinejacc.org/article.aspx?articleid=1831234>.

BioSpace, "CardiAQ Valve Technologies (CVT) Reports First-In-Human Percutaneous Transfemoral, Transseptal Implantation With Its Second Generation Transcatheter Bioprosthetic Mitral Heart Valve," Jun. 23, 2015, p. 1, http://www.biospace.com/News/cardiaq-valve-technologies-cvt-reports-first- in/382370.

BioSpace, "CardiAQ Valve Technologies (CVT) Reports Cardiovascular Medicine Milestone: First-In-Humannonsurgical Percutaneous Implantation of a Bioprosthetic Mitral Heart Valve," Jun. 14, 2012, p. 1, http://www.biospace.com/News/cardiaq-valve-technologies-cvt-reports/263900.

Berreklouw, Eric, PhD, et al., "Sutureless Mitral Valve Replacement With Bioprostheses and Nitinol Attachment Rings: Feasibility in Acute Pig Experiments," The Journal of Thoracic and Cardiovascular Surgery, vol. 142, No. 2, Aug. 2011 in 7 pages, Applicant believes this may have been available online as early as Feb. 7, 2011.

Backer, Ole De, MD, et al., "Percutaneous Transcatheter Mitral Valve Replacement—An Overview of Devices in Preclinical and Early Clinical Evaluation," Contemporary Reviews in Interventional Cardiology, Circ Cardiovasc Interv. 2014;7:400-409, Applicant believes this may have been available as early as Jun. of 2014.

Bavaria, Joseph E. M.D.: "CardiAQ Valve Technologies: Transcatheter Mitral Valve Implantation," Sep. 21, 2009.

Boudjemline, Younes, et al., "Steps Toward the Percutaneous Replacement of Atrioventricular Valves," JACC, vol. 46, No. 2, Jul. 19, 2005:360-5.

"CardiAQTM Valve Technologies reports Successful First-in-Human Trans-Apical implantation of its Second Generation Transcatheter Mitral Valve," CardiAQ Valve Technologies Press Release, May 20, 2014.

CardiAQ Valve Technologies, "Innovations in Heart Valve Therapy," In3 San Francisco, Jun. 18, 2008, PowerPoint presentation in 19 slides.

Chiam, Paul T.L., et al., "Percutaneous Transcatheter Aortic Valve Implantation: Assessing Results, Judging Outcomes, and Planning Trials," JACC: Cardiovascular Interventions, The American College of Cardiology Foundation, vol. 1, No. 4, Aug. 2008:341-50.

Condado, Jose Antonio, et al., "Percutaneous Treatment of Heart Valves," Rev Esp Cardio. 2006;59(12):1225-31, Applicant believes this may have been available as early as Dec. of 2006.

"Company Overview," at TVT on Jun. 25, 2009.

Engager System, Precise Valve Positioning, Transcatheter Aortic Valve Implantation System, Transcatheter Aortic Valve Replacement—TAVR I Medtronic Engager, http://www.medtronic-engager.com/home/transcatheter-aortic-valve-repl., 2014 Medtronic, Inc. in 2 pages. Applicant believes this may have been available online as early as Aug. 25, 2013.

Feldman, Ted, MD. "Prospects for Percutaneous Valve Therapies," Circulation 2007;116:2866-2877. Applicant believes that this may be available as early as Dec. 11, 2007.

Fitzgerald, Peter J. M.D., "Tomorrow's Technology: Percutaneous Mitral Valve Replacement, Chordal Shortening, and Beyond," Transcatheter Valve Therapies (TVT) Conference. Seattle, WA. Applicant believes this may have been available as early as Jun. 7, 2010.

Fanning, Jonathon P., et al., "Transcatheter Aortic Valve Implantation (TAVI): Valve Design and Evolution," International Journal of Cardiology 168 (2013) 1822-1831, Applicant believes this may have been available as early as Oct. 3, 2013.

Fornell, Dave, "Transcatheter Mitral Valve replacement Devices in Development," Diagnostic and Interventional Cardiology, Dec. 30, 2014, p. 3, <http://www.dicardiology.com/article/transcatheter-mitral-valve-replacement-devices-development>.

Grube, E. et al, "Percutaneous aortic valve replacement for severe aortic stenosis in high-risk patients using the second- and current third-generation self-expanding CoreValve prosthesis: device success and 30-day clinical outcome." J Am Coll Cardiol. Jul. 3, 2007;50(1):69-76. Epub Jun. 6, 2007.

Horvath et al.: "Transapical Aortic Valve Replacement under Real-time Magnetic Resonance Imaging Guidance: Experimental Results with Balloon—Expandable and Self-Expanding Stents," http://www.ncbi.nlm.nih.gov/pmc/articles/PMC3038190/. Jun. 2011.

Karimi, Houshang, et al., "Percutaneous Valve Therapies," SIS 2007 Yearbook, Chapter 11, pp. 1-11.

Kronemyer, Bob, "CardiAQ Valve Technologies: Percutaneous Mitral Valve Replacement," Start Up—Windhover Review of Emerging Medical Ventures, vol. 14, Issue No. 6, Jun. 2009, pp. 48-49.

Leon, Martin B., et al., "Transcatheter Aortic Valve Replacement in Patients with Critical Aortic Stenosis: Rationale, Device Descriptions, Early Clinical Experiences, and Perspectives," Semin. Thorac. Cardiovasc. Surg. 18:165-174, 2006 in 10 pages, Applicant believes this may have been available as early as the Summer of 2006.

(56) References Cited

OTHER PUBLICATIONS

Lutter, Georg, et al., "Off-Pump Transapical Mitral Valve Replacement," European Journal of Cardio-thoracic Surgery 36 (2009) 124-128, Applicant believes this may have been available as early as Apr. 25, 2009.
Ma, Liang, et al., "Double-Crowned Valved Stents for Off-Pump Mitral Valve Replacement," European Journal of Cardio-thoracic Surgery 28 (2005) 194-199, Applicant believes this may have been available as early as Aug. of 2005.
Mack, Michael, M.D., "Antegrade Transcatheter Mitral valve Implantation: A Short-term Experience in Swine Model," Applicant believes this may have been presented on May of 2011 at TVT.
Mack, Michael, M.D., "Antegrade Transcatheter Mitral valve Implantation: On-Going Experience in Swine Model," Applicant believes this may have been presented on Nov. of 2011 at TCT.
Mack, Michael M.D., "Advantages and Limitations of Surgical Mitral Valve Replacement; Lessons for the Transcatheter Approach," Applicant believes this may have been available as early as Jun. 7, 2010. Applicant believes this may have been presented at the Texas Cardiovascular Innovative Ventures (TCIV) Conference in Dallas, TX on Dec. 8, 2010.
Masson, Jean-Bernard, et al., "Percutaneous Treatment of Mitral Regurgitation," Circulation: Cardiovascular Interventions, 2:140-146, Applicant believes this may have been available as early as Apr. 14, 2009.
Neovasc corporate presentation, Oct. 2009, available at http://www.neovasc.com/investors/documents/Neovasc-Corporate-Presentation-October-2009.pdf.
NJ350: Vote for Your Favorite New Jersey Innovations, Jun. 27, 2014, http://www.kilmerhouse.com/2014/06/nj350-vote-for-your-favorite-new-jersey-innovations/.
Ostrovsky, Gene, "Transcatheter Mitral Valve Implantation Technology from CardiAQ," medGadget, Jan. 15, 2010, available at: http://www.medgadget.com/2010/01/transcatheter_mitral_valve_implantation_technology_from_cardiaq.html.
Pluth, James R., M.D., et al., "Aortic and Mitral Valve Replacement with Cloth-Covered Braunwald-Cutter Prosthesis, A Three-Year Follow-up," The Annals of Thoracic Surgery, vol. 20, No. 3, Sep. 1975, pp. 239-248.
Piazza, Nicoló, MD, et al., "Anatomy of the Aortic Valvar Complex and Its Implications for Transcatheter Implantation of the Aortic Valve," Contemporary Reviews in Interventional Cardiology, Circ. Cardiovasc. Intervent., 2008;1:74-81, Applicant believes this may have been available as early as Aug. of 2008.
Preston-Maher, Georgia L., et al., "A Technical Review of Minimally Invasive Mitral Valve Replacements," Cardiovascular Engineering and Technology, vol. 6, No. 2, Jun. 2015, pp. 174-184. Applicant believes this may have been available as early as Nov. 25, 2014.
Quadri, Arshad M.D., "Transcatheter Mitral Valve Implantation (TMVI) (An Acute In Vivo Study)," Applicant believes this may have been presented on Sep. 22, 2010 at TCT.
Ratz, J. Brent et al., "Any experiences making an expandable stent frame?" Arch-Pub.com, Architecture Forums: Modeling, Multiple forum postings from Feb. 3, 2009 to Feb. 4, 2009, http://www.arch-pub.com.
Ratz, J. Brent, "LSI EMT Spotlight," May 15, 2009.
Ratz, J. Brent, "In3 Company Overview," Jun. 24, 2009.
Ruiz, Carlos E., "Overview of Novel Transcatheter Valve Technologies," Applicant believes this may have been presented on May 27, 2010 at EuroPCR.
Seidel, Wolfgang, et al., "A Mitral Valve Prosthesis and a Study of Thrombosis on Heart Valves in Dogs," JSR—vol. II, No. 3—May 1962, submitted for publication Oct. 9, 1961.
Sondergaard, Lars, et al., "Transcatheter Mitral Valve Implantation: CardiAQ™," Applicant believes this may have been presented at TCT 2013.
Sondergaard, Lars, et al., "Transcatheter Mitral Valve Implantation: CardiAQ™," Applicant believes this may have been presented at EuroPCR 2013.
Sondergaard, Lars, "CardiAQ TMVR FIH—Generation 2," Applicants believe this may have been presented in 2014 at the TVT symposium.
Spillner, J. et al., "New Sutureless 'Atrial—Mitral-Valve Prosthesis' for Minimally Invasive Mitral Valve Therapy," Textile Research Journal, 2010, in 7 pages, Applicant believes this may have been available as early as Aug. 9, 2010.
Taramasso et al.: "New devices for TAVI: technologies and initial clinical experiences" http://www.nature.com/nrcardio/journal/v11/n3/full/nrcardio.2013.221.html?message-global=remove#access. Jan. 21, 2014.
Treede et al.: "Transapical transcatheter aortic valve implantation using the JenaValve™ system: acute and 30-day results of the multicentre CE-mark study." http://ejcts.oxfordjournals.org/content/41/6/e131.long. Apr. 16, 2012.
"Update," Applicant believes this may have been presented on Jun. 6, 2010 at TVT.
Van Mieghem, et al., "Anatomy of the Mitral Valvular Complex and Its Implications for Transcatheter Interventions for Mitral Regurgitation," J. Am. Coll. Cardiol., 56:617-626 (Aug. 17, 2010).
Vu, Duc-Thang, et al., "Novel Sutureless Mitral Valve Implantation Method Involving a Bayonet Insertion and Release Mechanism: A Proof of Concept Study in Pigs," The Journal of Thoracic and Cardiovascular Surgery, vol. 143, No. 4, 985-988, Apr. 2012, Applicant believes this may have been available online as early as Feb. 13, 2012.
Wayback Machine, Cleveland Clinic Lerner Research Institute, Transcatheter Mitral Stent/Valve Prosthetic, https://web.archive.org/web/20130831094624/http://mds.clevelandclinic.org/Portfolio.aspx?n=331, indicated as archived on Aug. 31, 2013.
Webb, John G., et al., "Transcatheter Aortic Valve Implantation: The Evolution of Prostheses, Delivery Systems and Approaches," Archives of Cardiovascular Disease (2012) 105, 153-159. Applicant believes this may have been available as early as Mar. 16, 2012.

* cited by examiner

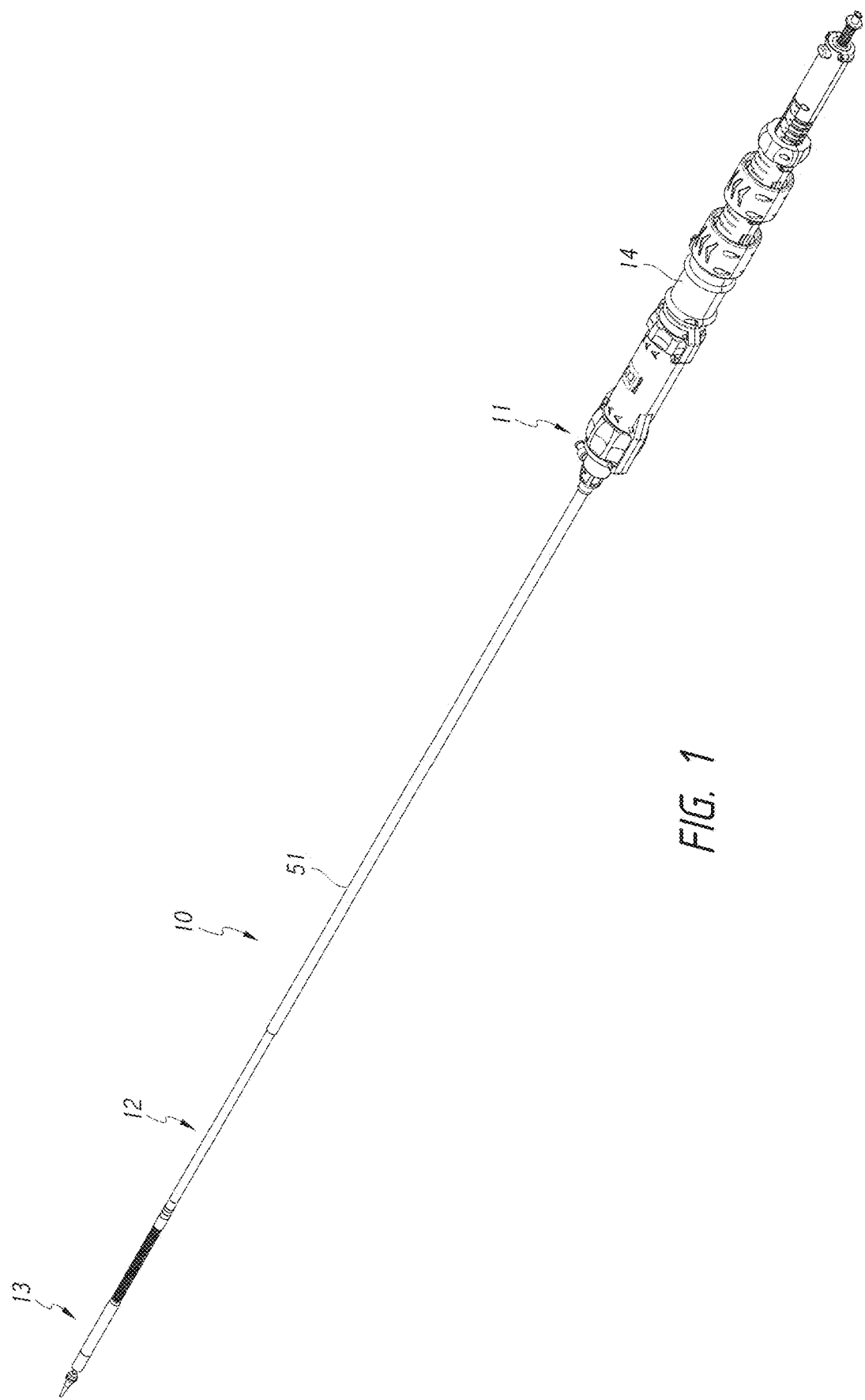

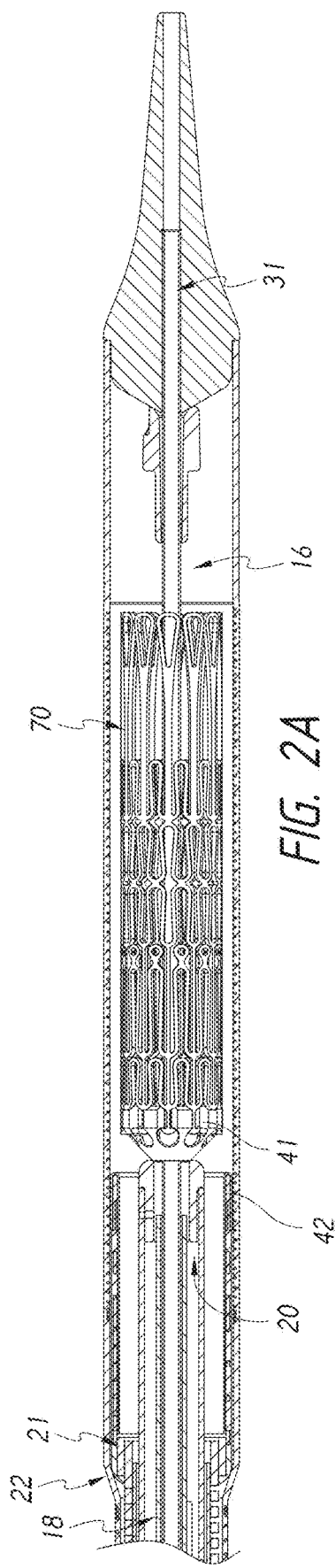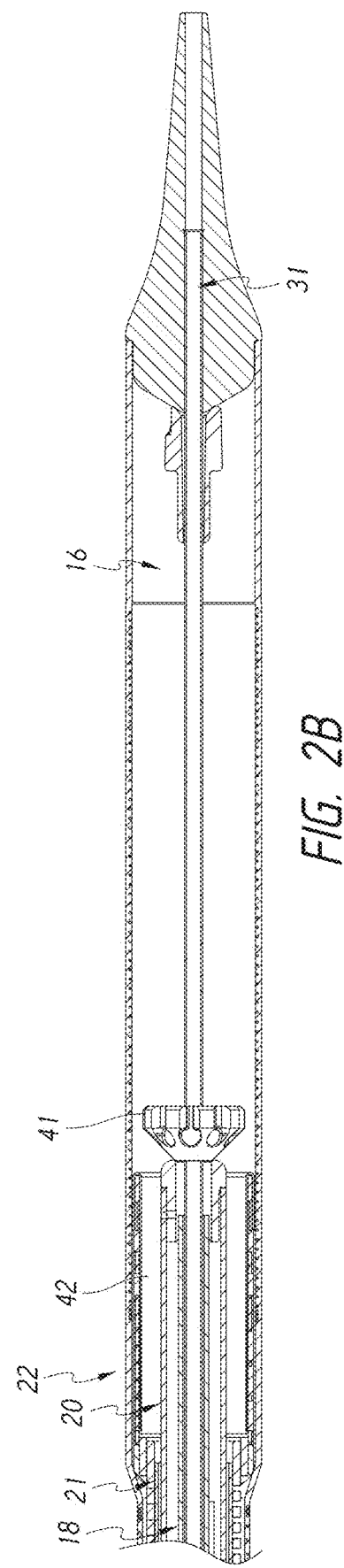

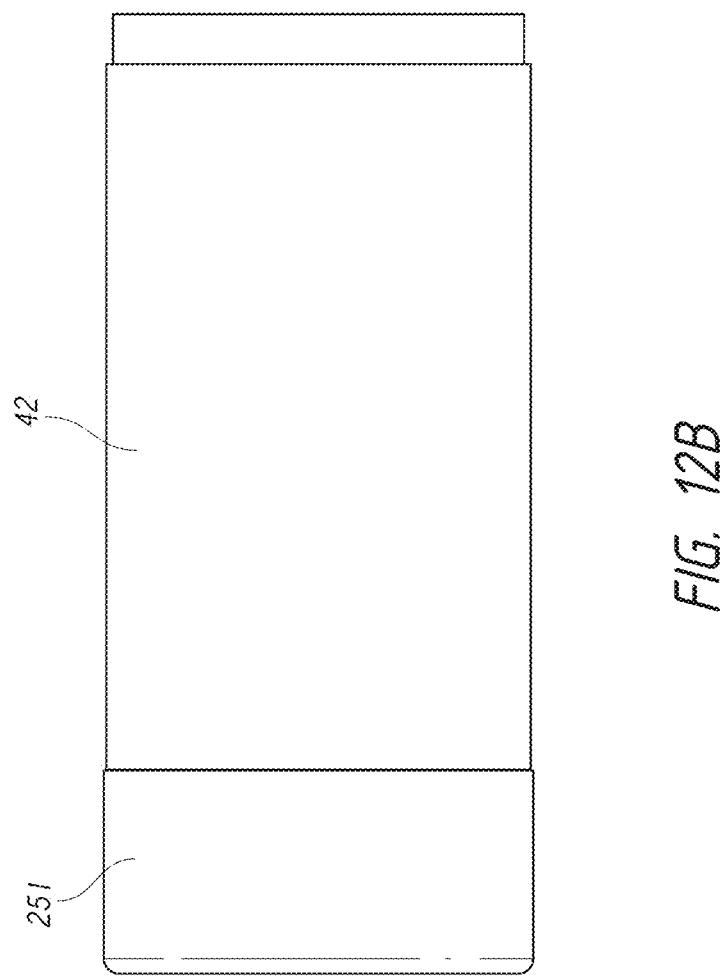

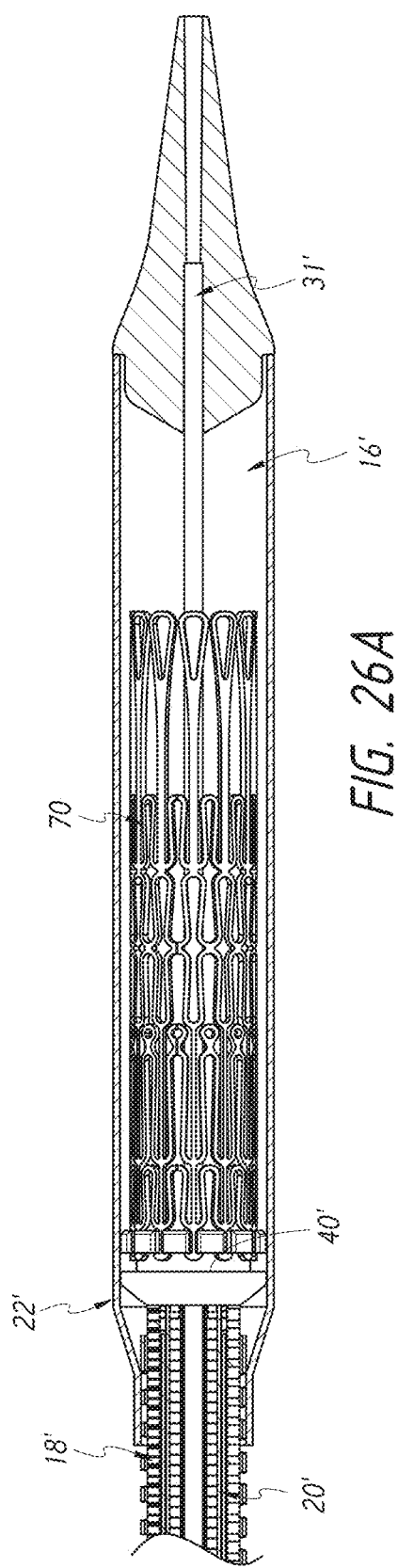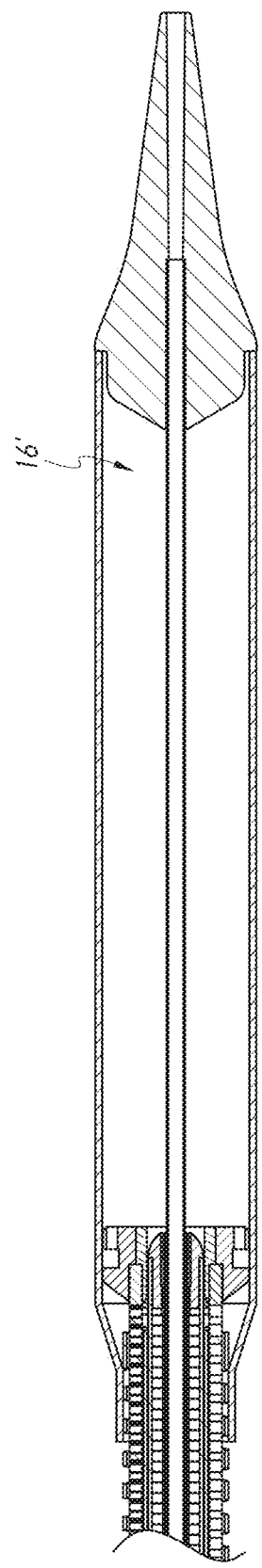

STEERABLE RAIL DELIVERY SYSTEM

CROSS REFERENCE TO RELATED APPLICATIONS

This application is a continuation of U.S. application Ser. No. 16/028,172, filed Jul. 5, 2018, now U.S. Pat. No. 10,813,757, which claims the benefit of U.S. Provisional Application No. 62/529,394, filed Jul. 6, 2017, entitled "STEERABLE RAIL DELIVERY SYSTEM" and U.S. Provisional Application No. 62/635,421, filed Feb. 26, 2018, entitled "STEERABLE RAIL DELIVERY SYSTEM", the entirety of each of which is hereby incorporated by reference. The embodiments of this application also relate to and may be combined with embodiments disclosed in U.S. application Ser. No. 16/027,974, filed on Jul. 5, 2018, entitled "STEERABLE DELIVERY SYSTEM AND COMPONENTS", the entirety of which is hereby incorporated by reference.

FIELD

Certain embodiments disclosed herein relate generally to prostheses for implantation within a lumen or body cavity and delivery systems for a prosthesis. In particular, the prostheses and delivery systems relate in some embodiments to replacement heart valves, such as replacement mitral heart valves.

BACKGROUND

Human heart valves, which include the aortic, pulmonary, mitral and tricuspid valves, function essentially as one-way valves operating in synchronization with the pumping heart. The valves allow blood to flow downstream, but block blood from flowing upstream. Diseased heart valves exhibit impairments such as narrowing of the valve or regurgitation, which inhibit the valves' ability to control blood flow. Such impairments reduce the heart's blood-pumping efficiency and can be a debilitating and life-threatening condition. For example, valve insufficiency can lead to conditions such as heart hypertrophy and dilation of the ventricle. Thus, extensive efforts have been made to develop methods and apparatuses to repair or replace impaired heart valves.

Prostheses exist to correct problems associated with impaired heart valves. For example, mechanical and tissue-based heart valve prostheses can be used to replace impaired native heart valves. More recently, substantial effort has been dedicated to developing replacement heart valves, particularly tissue-based replacement heart valves that can be delivered with less trauma to the patient than through open heart surgery. Replacement valves are being designed to be delivered through minimally invasive procedures and even percutaneous procedures. Such replacement valves often include a tissue-based valve body that is connected to an expandable frame that is then delivered to the native valve's annulus.

Development of prostheses including but not limited to replacement heart valves that can be compacted for delivery and then controllably expanded for controlled placement has proven to be particularly challenging. An additional challenge relates to the ability of such prostheses to be secured relative to intralumenal tissue, e.g., tissue within any body lumen or cavity, in an atraumatic manner.

Delivering a prosthesis to a desired location in the human body, for example delivering a replacement heart valve to the mitral valve, can also be challenging. Obtaining access to perform procedures in the heart or in other anatomical locations may require delivery of devices percutaneously through tortuous vasculature or through open or semi-open surgical procedures. The ability to control the deployment of the prosthesis at the desired location can also be challenging.

SUMMARY

Embodiments of the present disclosure are directed to a prosthesis, such as but not limited to a replacement heart valve. Further embodiments are directed to delivery systems, devices and/or methods of use to deliver and/or controllably deploy a prosthesis, such as but not limited to a replacement heart valve, to a desired location within the body. In some embodiments, a replacement heart valve and methods for delivering a replacement heart valve to a native heart valve, such as a mitral valve, are provided.

In some embodiments, a delivery system and method are provided for delivering a replacement heart valve to a native mitral valve location. The delivery system and method may utilize a transseptal approach. In some embodiments, components of the delivery system facilitate bending of the delivery system to steer a prosthesis from the septum to a location within the native mitral valve. In some embodiments, a capsule is provided for containing the prosthesis for delivery to the native mitral valve location. In other embodiments, the delivery system and method may be adapted for delivery of implants to locations other than the native mitral valve.

The present disclosure includes, but is not limited to, the following embodiments.

Embodiment 1: A delivery system for delivering an expandable implant to a body location, the delivery system comprising an outer sheath assembly comprising an outer shaft having an outer lumen and a proximal end and a distal end, wherein the outer sheath assembly comprises an implant retention area configured to retain the expandable implant in a compressed configuration, a rail assembly located within the outer lumen, the rail assembly comprising a rail shaft having a rail lumen and a proximal end and a distal end, wherein the rail assembly comprises one or more pull wires attached on an inner surface of the rail shaft configured to provide an axial force on the rail shaft to steer the rail assembly, and an inner assembly located within the outer lumen, the inner assembly comprising an inner shaft having an inner lumen and a proximal end and a distal end, wherein the inner assembly comprises an inner retention member configured to be releasably attached to the expandable implant, wherein the outer sheath assembly and the inner assembly are configured to move together distally relative to the rail assembly while the expandable implant remains in the compressed configuration, and wherein the outer sheath assembly is configured to retract proximally relative to the inner assembly in order to at least partially expand the expandable implant from the compressed configuration.

Embodiment 2: The delivery system of Embodiment 1, wherein the inner assembly is located within the rail lumen.

Embodiment 3: The delivery system of Embodiments 1 or 2, further comprising a mid shaft assembly within the outer lumen, the mid shaft assembly comprising a mid shaft having a middle lumen and a proximal end and a distal end, wherein the mid shaft assembly comprises an outer retention member configured to radially restrain at least a portion of the expandable implant, and wherein the mid shaft assembly is configured to move distally relative to the rail assembly while the expandable implant remains in the compressed configuration, and wherein the mid shaft assembly is configured to retract proximally relative to the inner assembly in order to fully release the expandable implant.

Embodiment 4: The delivery system of Embodiment 3, wherein the rail assembly is located within the middle lumen.

Embodiment 5: The delivery system of any one of the preceding Embodiments, further comprising a nose cone assembly located within the inner lumen, the nose cone assembly comprising a nose cone shaft having a guide wire lumen, a proximal and distal end, and a nose cone on the distal end, wherein the nose cone assembly is configured to move distally relative to the rail assembly while the expandable implant remains in the compressed configuration.

Embodiment 6: The delivery system of Embodiment 5, wherein the nose cone assembly is configured to move together distally with the outer sheath assembly and the inner assembly relative to the rail assembly while the expandable implant remains in the compressed configuration.

Embodiment 7: The delivery system of Embodiment 1, wherein the rail assembly is located within the inner lumen.

Embodiment 8: The delivery system of any one of the preceding Embodiments, wherein the rail shaft is configured to form a proximal bend and a distal bend.

Embodiment 9: The delivery system of any one of the preceding Embodiments, wherein the one or more pull wires comprise a proximal pull wire and a distal pull wire, wherein the proximal pull wire attaches to the rail shaft at a location proximal to an attachment point of the distal pull wire.

Embodiment 10: The delivery system of any one of the preceding Embodiments, further comprising a handle, wherein the handle comprises a first actuator configured to move together distally the outer sheath assembly and the inner assembly.

Embodiment 11: The delivery system of Embodiment 10, wherein the handle comprises a second actuator configured to retract proximally the outer sheath assembly relative to the inner assembly.

Embodiment 12: The delivery system of Embodiments 3 or 4, further comprising a handle, wherein the handle comprises a first actuator configured to move together distally the outer sheath assembly, the inner assembly and the mid shaft assembly, a second actuator configured to retract proximally the outer assembly relative to the inner assembly, and a third actuator configured to retract proximally the mid shaft assembly relative to the inner assembly.

Embodiment 13: The delivery system of Embodiments 5 or 6, further comprising a handle, wherein the handle comprises a locking button for preventing axial motion of the nose cone assembly.

Embodiment 14: The delivery system of Embodiments 3 or 4, further comprising a handle, wherein the handle comprises a single flush port, and wherein the single flush port is configured to provide fluid access between the rail lumen, the outer sheath lumen, and the mid shaft lumen.

Embodiment 15: The delivery system of any one of the preceding Embodiments, further comprising the expandable implant, wherein a distal end of the expandable implant is restrained by the outer sheath assembly and a proximal end of the expandable implant is restrained the inner retention member of the inner assembly.

Embodiment 16: The delivery system of Embodiment 15, wherein the expandable implant comprises a replacement mitral valve comprising a plurality of anchors configured to positioned on a ventricular side of a native mitral valve annulus.

Embodiment 17: The delivery system of any one of the preceding Embodiments, wherein the rail assembly is configured to steer the rail assembly toward a native mitral valve location in a transseptal approach.

Embodiment 18: The delivery system of any one of the preceding Embodiments, wherein the rail comprises at least one pull wire lumen attached to an inner surface of the rail lumen, wherein the at least one pull wire passes through the at least one pull wire lumen.

Embodiment 19: The delivery system of Embodiments 5 or 6, further comprising a guide wire shield having a proximal diameter smaller than a distal diameter, the guide wire shield located on the nose cone shaft, wherein the guide wire sheath is configured to protect the nose cone shaft from being crushed during implant crimping, and wherein a distal end of the expandable implant is configured to radially contact the proximal diameter in the compressed configuration.

Embodiment 20: The delivery system of Embodiment 1, further comprising a mid shaft assembly within the outer lumen, the mid shaft assembly comprising a mid shaft having a middle lumen and a proximal end and a distal end, wherein the mid shaft assembly comprises an outer retention member configured to radially restrain at least a portion of the expandable implant, and a nose cone assembly located within the inner lumen, the nose cone assembly comprising a nose cone shaft having a guide wire lumen, a proximal and distal end, and a nose cone on the distal end, wherein the mid shaft assembly and the nose cone assembly are configured to move together distally with the outer sheath assembly and the inner assembly relative to the rail assembly while the expandable implant remains in the compressed configuration, and wherein the mid shaft assembly is configured to retract proximally relative to the inner assembly in order to at least partially expand the expandable implant from the compressed position.

Embodiment 21: The delivery system of Embodiment 3, wherein the mid shaft assembly is configured to move distally relative to the rail assembly together with the outer sheath assembly and the inner assembly.

Embodiment 22: The delivery system of Embodiment 5, wherein the nose cone assembly is configured to move distally relative to the rail assembly together with the outer sheath assembly and the inner assembly.

Embodiment 23: A delivery system for delivering an expandable implant to a body location, the delivery system comprising an outer sheath assembly comprising an outer shaft having an outer lumen and a proximal end and a distal end, wherein the outer sheath assembly comprises an implant retention area configured to retain the expandable implant in a compressed configuration, wherein the outer sheath assembly comprises a capsule at the distal end, the capsule comprising an outer polymer layer, a metal middle layer located on a radially inner surface of the outer polymer layer, and an inner liner located on a radially inner surface of the middle layer.

Embodiment 24: The delivery system of Embodiment 23, wherein the inner liner comprises extruded PTFE.

Embodiment 25: The delivery system of Embodiment 23 or 24, wherein the inner liner wraps around a distal end of the capsule and is in contact with a radially outer surface of the outer polymer layer.

Embodiment 26: The delivery system of any one of Embodiments 23-25, further comprising a fluoroelastomer layer configured to bond the inner liner to the middle layer.

Embodiment 27: The delivery system of any one of Embodiments 23-26, further comprising a fluorinated ethylene polymer layer located between the inner layer and the metal layer.

Embodiment 28: The delivery system of any one of Embodiments 23-27, wherein the metal middle layer is at least partially a metal coil.

Embodiment 29: The delivery system of any one of Embodiments 23-28, wherein the outer polymer layer comprises ePTFE.

Embodiment 30: The delivery system of any one of Embodiments 23-29, wherein the inner liner comprises pre-axially compressed PTFE.

Embodiment 31: A method for delivering an expandable implant to a body location, the method comprising delivering an expandable implant within an outer sheath assembly of a delivery system toward the body location, the expandable implant having a distal end and a proximal end, wherein the expandable implant is in a radially compressed configuration within the outer assembly and is releasably retained in the outer assembly with an inner retention member, activating a pull wire in a rail assembly of the delivery system to steer the delivery system, the rail assembly comprising a rail shaft having a rail lumen and a proximal end and a distal end, wherein activating the pull wire provides at least one bend to the rail shaft, moving the outer sheath assembly and the inner retention member distally together relative to the rail assembly to position the expandable implant at the body location while the expandable implant remains in the radially compressed configuration, and proximally retracting the outer sheath assembly relative to the inner retention member in order to at least partially expand the expandable implant from the radially compressed configuration.

Embodiment 32: The method of Embodiment 31, further comprising activating a second pull wire in the rail assembly to provide a second bend to the rail shaft.

Embodiment 33: The method of Embodiment 31, wherein the inner retention member is located within the rail lumen.

Embodiment 34: The method of any one of Embodiments 31-33, further comprising moving a mid shaft assembly comprising an outer retention member configured to radially restrain at least a portion of the expandable distally together with the outer sheath assembly and the inner retention ring to position the expandable implant at the body location while the expandable implant remains in the radially compressed configuration.

Embodiment 35: The method of Embodiment 34, further comprising proximally retracting the mid shaft assembly relative to the inner retention member in order to at least partially expand the expandable implant.

Embodiment 36: The method of any one of Embodiments 34-35, wherein the rail assembly is located within the mid shaft assembly.

Embodiment 37: The method of any one of Embodiments 31-33, further comprising moving a nose cone assembly comprising a nose cone shaft and a nose cone distally together with the outer sheath assembly and the inner retention member to position the expandable implant at the body location while the expandable implant remains in the radially compressed configuration.

Embodiment 38: The method of any one of Embodiments 31-37, further comprising activating a second pull wire in the rail assembly to form a second bend to the rail shaft.

Embodiment 39: The method of any one of Embodiments 31-38, wherein the moving the outer sheath assembly and the inner retention member comprises activating a first actuator on a handle.

Embodiment 40: The method of any one of Embodiments 39, wherein the proximally retracting the outer sheath assembly comprises activating a second actuator on the handle.

Embodiment 41: The method of any one of Embodiments 31-40, wherein the pull wire passes through a pull wire lumen attached to an inner surface of the rail lumen.

Embodiment 42: The method of any one of Embodiments 31-41, wherein the body location is a native mitral valve, and wherein activating the pull wire provides at least one bend to the rail shaft to steer the delivery system toward the native mitral valve in a trans septal approach.

Embodiment 43: A delivery system for delivering an expandable implant to a body location, the delivery system comprising an outer sheath assembly comprising an outer shaft having an outer lumen and a proximal end and a distal end, wherein the outer sheath assembly comprises an implant retention area configured to retain the expandable implant in a compressed configuration, a rail assembly located within the outer lumen, the rail assembly comprising a rail shaft having a rail lumen and a proximal end and a distal end, wherein the rail assembly comprises one or more pull wires attached on an inner surface of the rail shaft configured to provide an axial force on the rail shaft to steer the rail assembly, and an inner assembly located within the outer lumen, the inner assembly comprising an inner shaft having an inner lumen and a proximal end and a distal end, wherein the inner assembly comprises an inner retention member configured to be releasably attached to the expandable implant, a mid shaft assembly within the outer lumen, the mid shaft assembly comprising a mid shaft having a middle lumen and a proximal end and a distal end, wherein the mid shaft assembly comprises an outer retention member configured to radially restrain at least a portion of the expandable implant, and a nose cone assembly located within the inner lumen, the nose cone assembly comprising a nose cone shaft having a guide wire lumen, a proximal and distal end, and a nose cone on the distal end, wherein the outer sheath assembly, the mid shaft assembly, the inner assembly, and the nose cone assembly are configured to move together distally relative to the rail assembly while the expandable implant remains in the compressed configuration, and wherein the outer sheath assembly and the mid shaft assembly are configured to individually retract proximally relative to the inner assembly in order to at least partially expand the expandable implant from the compressed configuration.

Embodiment 44: The delivery system of Embodiment 3, wherein the outer retention member comprises an inner liner that wraps around a distal end of the outer retention member and is in contact with a radially outer surface of the member.

Embodiment 45: A delivery system for delivering an expandable implant to a body location, the delivery system comprising an outer sheath assembly comprising an outer shaft having an outer lumen and a proximal end and a distal end, wherein the outer sheath assembly comprises an implant retention area configured to retain the expandable implant in a compressed configuration, and a rail assembly located within the outer lumen, the rail assembly comprising a steerable rail shaft that is actuatable into a shape comprising one or more bends, wherein the outer sheath assembly is configured to move distally over the rail assembly when the steerable rail shaft is actuated to position the expandable implant while in the compressed configuration at the body location, the steerable rail shaft being sufficiently rigid to maintain its shape while the outer sheath assembly moves distally over the rail assembly, and wherein the outer sheath assembly at least in the implant retention area is sufficiently flexible to track over at least one of the one or more bends of the steerable rail shaft when the steerable rail shaft is actuated.

Other embodiments of the present disclosure include but are not limited to a delivery system comprising one or more of the features described above or described further below. For example, in one embodiment a delivery system may comprise a capsule having one or more of the features as described herein. In another embodiment, a delivery system may comprise a shaft having one or more of the features described herein. In another embodiment, a delivery system may comprise a guide wire shield having one or more of the features as described herein. In another embodiment, a delivery system may comprise a steerable rail having one or more of the features as described herein. In another embodiment, a delivery system may comprise a prosthesis having one or more of the features as described herein. In another embodiment, a delivery system may comprise an outer retention member having one or more of the features as described herein.

BRIEF DESCRIPTION OF THE DRAWINGS

FIG. 1 shows an embodiment of a delivery system.

FIG. 2A shows a partial cross-sectional view of the distal end of the delivery system of FIG. 1 loaded with the valve prosthesis of FIG. 3A.

FIG. 2B shows a partial cross-sectional view of the distal end of the delivery system of FIG. 1 without the valve prosthesis of FIG. 3A.

FIG. 12B illustrates an embodiment of an outer retention ring.

FIG. 26A shows a partial cross-sectional view of the distal end of the delivery system of FIG. 25 loaded with the valve prosthesis of FIG. 3A.

FIG. 26B shows a partial cross-sectional view of the distal end of the delivery system of FIG. 25 without the valve prosthesis of FIG. 3A.

DETAILED DESCRIPTION

Figure 2C:
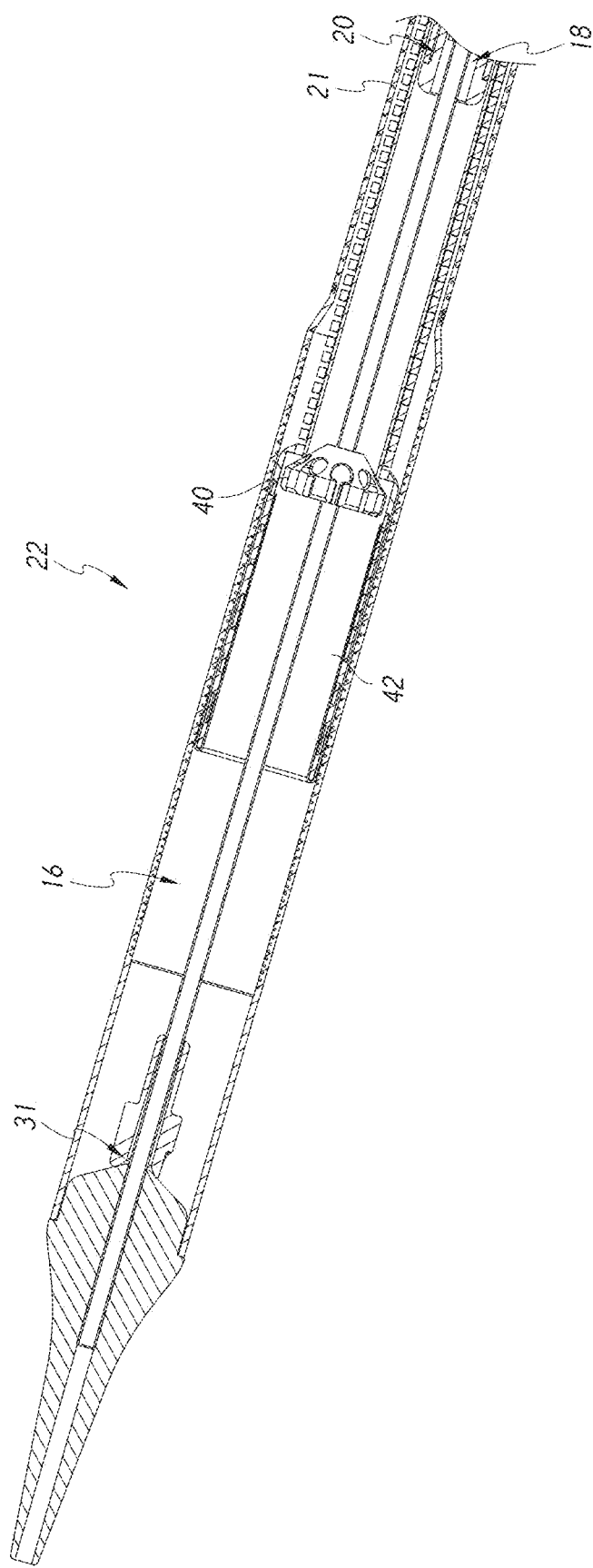
FIG. 2C shows a partial cross-sectional view of the distal end of the delivery system of FIG. 1 without with certain shaft assemblies translated along the rail assembly.

The present specification and drawings provide aspects and features of the disclosure in the context of several embodiments of replacement heart valves, delivery systems and methods that are configured for use in the vasculature of a patient, such as for replacement of natural heart valves in a patient. These embodiments may be discussed in connection with replacing specific valves such as the patient's aortic, tricuspid, or mitral valve. However, it is to be understood that the features and concepts discussed herein can be applied to products other than heart valve implants. For example, the controlled positioning, deployment, and securing features described herein can be applied to medical implants, for example other types of expandable prostheses, for use elsewhere in the body, such as within an artery, a vein, or other body cavities or locations. In addition, particular features of a valve, delivery system, etc. should not be taken as limiting, and features of any one embodiment discussed herein can be combined with features of other embodiments as desired and when appropriate. While certain of the embodiments described herein are described in connection with a transfemoral delivery approach, it should be understood that these embodiments can be used for other delivery approaches such as, for example, transapical or transjugular approaches. Moreover, it should be understood that certain of the features described in connection with some embodiments can be incorporated with other embodiments, including those which are described in connection with different delivery approaches.

Delivery System

FIG. 1 illustrates an embodiment of a delivery device, system, or assembly 10. The delivery system 10 can be used to deploy a prosthesis, such as a replacement heart valve, within the body. In some embodiments, the delivery system 10 can use a dual plane deflection approach to properly delivery the prosthesis. Replacement heart valves can be delivered to a patient's heart mitral valve annulus or other heart valve location in various manners, such as by open surgery, minimally-invasive surgery, and percutaneous or transcatheter delivery through the patient's vasculature. Example transfemoral approaches may be found in U.S. Pat. Pub. No. 2015/0238315, filed Feb. 20, 2015, the entirety of which is hereby incorporated by reference in its entirety. While the delivery system 10 is described in connection with a percutaneous delivery approach, and more specifically a transfemoral delivery approach, it should be understood that features of delivery system 10 can be applied to other delivery system, including delivery systems for a transapical delivery approach.

The delivery system 10 can be used to deploy a prosthesis, such as a replacement heart valve as described elsewhere in this specification, within the body. The delivery system 10 can receive and/or cover portions of the prosthesis such as a first end 301 and second end 303 of the prosthesis 70 illustrated in FIG. 3A below. For example, the delivery system 10 may be used to deliver an expandable implant or prosthesis 70, where the prosthesis 70 includes the first end 301 and the second end 303, and wherein the second 303 end is configured to be deployed or expanded before the first end 301.

FIG. 2A further shows an example of the prosthesis 70 that can be inserted into the delivery system 10, specifically into the implant retention area 16. For ease of understanding, in FIG. 2A, the prosthesis is shown with only the bare metal frame illustrated. The implant or prosthesis 70 can take any number of different forms. A particular example of frame for a prosthesis is shown in FIG. 3A, though it will be understood that other designs can also be used. The prosthesis 70 can include one or more sets of anchors, such as distal (or ventricular) anchors 80 extending proximally when the prosthesis frame is in an expanded configuration and proximal (or atrial) anchors 82 extending distally when the prosthesis frame is in an expanded configuration. The prosthesis can further include struts 72 which may end in mushroom-shaped tabs 74 at the first end 301. Further discussion can be found in U.S. Publication No. 2015/0328000A1, published Nov. 19, 2015, hereby incorporated by reference in its entirety.

Figure 3A:
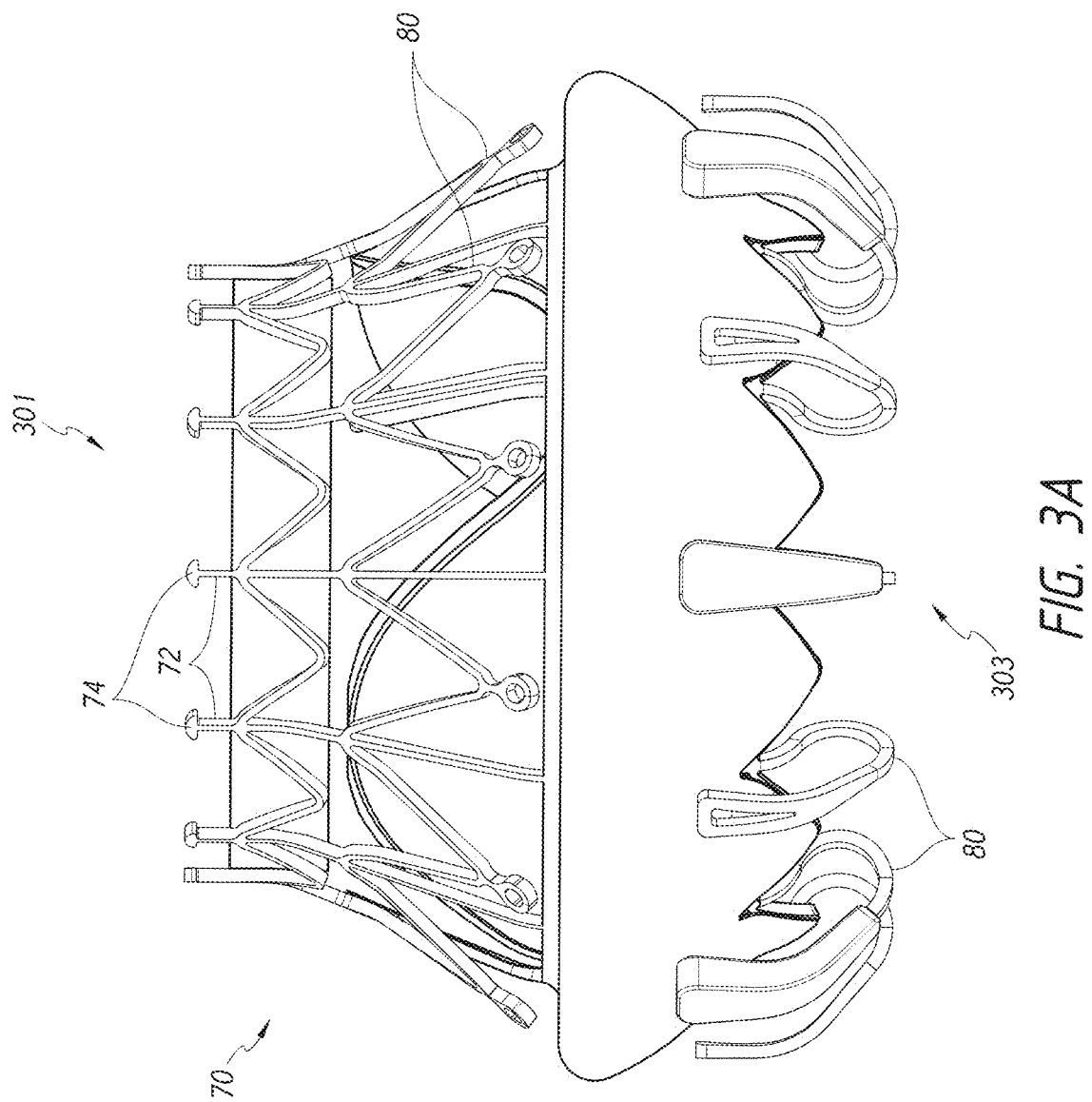
FIG. 3A shows a side view of an embodiment of a valve prosthesis that may be delivered using the delivery systems described herein.
Figure 3B:
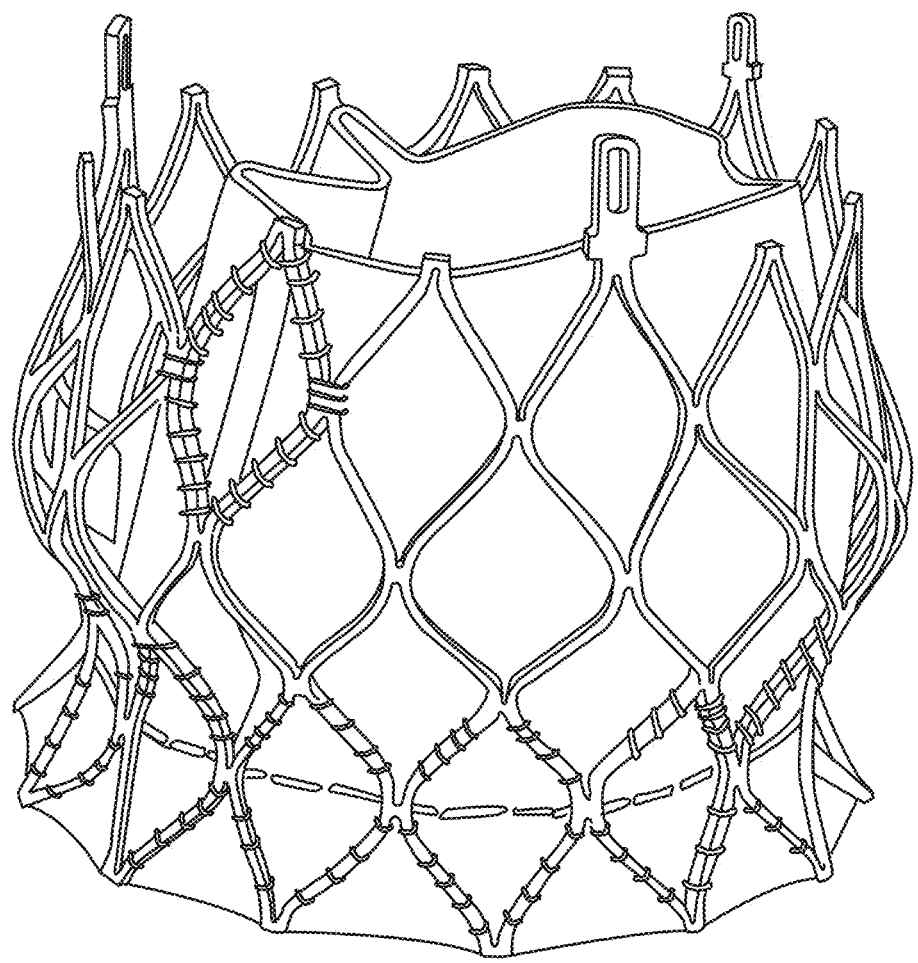
FIG. 3B shows a side view of an embodiment of an aortic valve prosthesis that may be delivered using the delivery systems described herein.

In some embodiments, the delivery system 10 can be used in conjunction with a replacement aortic valve, such as shown in FIG. 3B. In some embodiments the delivery system 10 can be modified to support and delivery the replacement aortic valve. However, the procedures and structures discussed below can similarly be used for a replacement mitral and replacement aortic valve.

Additional details and example designs for a prosthesis are described in U.S. Pat. Nos. 8,403,983, 8,414,644, 8,652,203 and U.S. Patent Publication Nos. 2011/0313515, 2012/0215303, 2014/0277390, 2014/0277422, 2014/0277427, 2018/0021129, and 2018/0055629, the entirety of these patents and publications are hereby incorporated by reference and made a part of this specification. Further details and embodiments of a replacement heart valve or prosthesis and its method of implantation are described in U.S. Publication Nos. 2015/0328000 and 2016/0317301 the entirety of each of which is hereby incorporated by reference and made a part of this specification.

The delivery system 10 can be relatively flexible. In some embodiments, the delivery system 10 is particularly suitable for delivering a replacement heart valve to a mitral valve location through a trans septal approach (e.g., between the right atrium and left atrium via a transseptal puncture).

As shown in FIG. 1, the delivery system 10 can include a shaft assembly 12 comprising a proximal end 11 and a distal end 13, wherein a handle 14 is coupled to the proximal end of the assembly 12. The shaft assembly 12 can be used to hold the prosthesis for advancement of the same through the vasculature to a treatment location. The delivery system 10 can further comprise a relatively rigid live-on (or integrated) sheath 51 surrounding the shaft assembly 12 that can prevent unwanted motion of the shaft assembly 12. The live-on sheath 51 can be attached at a proximal end of the shaft assembly 12 proximal to the handle 14, for example at a sheath hub. The shaft assembly 12 can include an implant retention area 16 (shown in FIGS. 2A-B with FIG. 2A showing the prosthesis 70 and FIG. 2B with the prosthesis 70 removed) at its distal end that can be used for this purpose. In some embodiments, the shaft assembly 12 can hold an expandable prosthesis in a compressed state at implant retention area 16 for advancement of the prosthesis 70 within the body. The shaft assembly 12 may then be used to allow controlled expansion of the prosthesis 70 at the treatment location. In some embodiments, the shaft assembly 12 may be used to allow for sequential controlled expansion of the prosthesis 70 as discussed in detail below. The implant retention area 16 is shown in FIGS. 2A-B at the distal end of the delivery system 10, but may also be at other locations. In some embodiments, the prosthesis 70 may be rotated in the implant retention area 16, such as through the rotation of the inner shaft assembly 18 discussed herein.

As shown in cross-sectional view of FIGS. 2A-B, the distal end of the delivery system 10 can include one or more subassemblies such as an outer sheath assembly 22, a mid shaft assembly 21, a rail assembly 20, an inner shaft assembly 18, and a nose cone assembly 31 as will be described in more detail below. In some embodiments, the delivery system 10 may not have all of the assemblies disclosed herein. For example, in some embodiments a full mid shaft assembly may not be incorporated into the delivery system 10, such as described in the embodiment of FIGS. 25-36 below. In some embodiments, the assemblies disclosed below may be in a different radial order than is discussed.

In particular, embodiments of the disclosed delivery system 10 can utilize a steerable rail in the rail assembly 20 for steering the distal end of the delivery system 10, allowing the implant to be properly located in a patient's body. As discussed in detail below, the steerable rail can be, for example, a rail shaft that extends through the delivery system 10 from the handle 14 generally to the distal end. In some embodiments, the steerable rail has a distal end that ends proximal to the implant retention area 16. A user can manipulate the bending of the distal end of the rail, thereby bending the rail in a particular direction. In preferred embodiments, the rail has more than one bend along its length, thereby providing multiple directions of bending. As the rail is bent, it presses against the other assemblies to bend them as well, and thus the other assemblies of the delivery system 10 can be configured to steer along with the rail as a cooperating single unit, thus providing for full steerability of the distal end of the delivery system.

Once the rail is steered into a particular location in a patient's body, the prosthesis 70 can be advanced along or relative to the rail through the movement of the other sheaths/shafts relative to the rail and released into the body. For example, the rail can be bent into a desired position within the body, such as to direct the prosthesis 70 towards the native mitral valve. The other assemblies (e.g., the outer sheath assembly 22, the mid shaft assembly 21, the inner assembly 18, and the nose cone assembly 31) can passively follow the bends of the rail. Further, the other assemblies (e.g., the outer sheath assembly 22, the mid shaft assembly 21, the inner assembly 18, and the nose cone assembly 31) can be advanced together (e.g., relatively together, sequentially with one actuator, simultaneously, almost simultaneously, at the same time, closely at the same time) relative to the rail while maintaining the prosthesis 70 in the compressed position without releasing or expanding the prosthesis 70 (e.g., within the implant retention area 16). The other assemblies (e.g., the outer sheath assembly 22, the mid shaft assembly 21, the inner assembly 18, and the nose cone assembly 31) can be advanced distally or proximally together relative to the rail. In some embodiments, only the outer sheath assembly 22, mid shaft assembly 21, and inner assembly 18 are advanced together over the rail. Thus, the nose cone assembly 31 may remain in the same position. The assemblies can be individually, sequentially, or simultaneously, translated relative to the inner assembly 18 in order to release the implant 70 from the implant retention area 16.

FIG. 2C illustrates the sheath assemblies, specifically the outer sheath assembly 22, the mid shaft assembly 21, the inner shaft assembly 18, and the nose cone assembly 31 having translated distally together along the rail assembly 20, further details on the assemblies are below. In some embodiments, the outer sheath assembly 22, the mid shaft assembly 21, the inner shaft assembly 18, and the nose cone assembly 31 translate together (e.g., relatively together, sequentially with one actuator, simultaneously, almost simultaneously, at the same time, closely at the same time). This distal translation can occur while the implant 70 remains in a compressed configuration within the implant retention area 16.

As shown in FIGS. 2A-2C and as further shown in FIGS. 4-8, starting with the outermost assembly, the delivery system can include an outer sheath assembly 22 forming a radially outer covering, or sheath, to surround an implant retention area 16 and prevent the implant from radially expanding. Specifically, the outer sheath assembly 22 can prevent radial expansion of the distal end of the implant from radially expanding. Moving radially inward, the mid shaft assembly 21 can be composed of a mid shaft hypotube 43 with its distal end attached to an outer retention member or outer retention ring 42 for radially retaining a portion of the prosthesis in a compacted configuration, such as a proximal end of the prosthesis 70. The mid shaft assembly 21 can be located within a lumen of the outer sheath assembly 22. Moving further inwards, the rail assembly 20 can be configured for steerability, as mentioned above and further described below. The rail assembly 20 can be located within a lumen of the mid shaft assembly 21. Moving further inwards, the inner shaft assembly 18 can be composed of an inner shaft with its distal end attached to inner retention member or inner retention ring 40 (such as a PEEK ring) for axially retaining the prosthesis, for example the proximal end of the prosthesis. The inner shaft assembly 18 can be located within a lumen of the rail assembly 20. Further, the most radially-inward assembly is the nose cone assembly 31 which includes the nose cone shaft 27 having its distal end connected to the nose cone 28. The nose cone 28 can have a tapered tip. The nose cone assembly 31 is preferably located within a lumen of the inner shaft assembly 18. The nose cone assembly 31 can include a lumen for a guide wire to pass therethrough.

The shaft assembly 12, and more specifically the nose cone assembly 31, inner assembly 18, rail assembly 20, mid shaft assembly 21, and outer sheath assembly 22, can be collectively configured to deliver a prosthesis 70 positioned within the implant retention area 16 (shown in FIG. 2A) to a treatment location. One or more of the subassemblies can then be moved to allow the prosthesis 70 to be released at the treatment location. For example, one or more of the subassemblies may be movable with respect to one or more of the other subassemblies. The handle 14 can include various control mechanisms that can be used to control the movement of the various subassemblies as will also be described in more detail below. In this way, the prosthesis 70 can be controllably loaded onto the delivery system 10 and then later deployed within the body. Further, the handle 14 can provide steering to the rail assembly 20, providing for bending/flexing/steering of the distal end of the delivery system 10.

As will be discussed below, the inner retention member 40, the outer retention ring 42, and the outer sheath assembly 22 can cooperate to hold the prosthesis 70 in a compacted configuration. The inner retention member 40 is shown engaging struts 72 at the proximal end 301 of the prosthesis 70 in FIG. 2A. For example, slots located between radially extending teeth on the inner retention member 40 can receive and engage the struts 72 which may end in mushroom-shaped tabs 74 on the proximal end of the prosthesis 70. The mid shaft assembly 21 can be positioned over the inner retention member 40 so that the first end 301 of the prosthesis 70 is trapped between the inner retention member 40 and the outer retention ring 42, thereby securely attaching it to the delivery system 10 between the mid shaft assembly 21 and the inner retention member 40. The outer sheath assembly 22 can be positioned to cover the second end 303 of the prosthesis 70.

The outer retention member 42 may be attached to a distal end of the mid shaft hypotube 43 which can in turn be attached to a proximal tube 44 at a proximal end, which in turn can be attached at a proximal end to the handle 14. The outer retention member 42 can provide further stability to the prosthesis 70 when in the compressed position. The outer retention member 42 can be positioned over the inner retention member 40 so that the proximal end of the prosthesis 70 is trapped therebetween, securely attaching it to the delivery system 10. The outer retention member 42 can encircle a portion of the prosthesis 70, in particular the first end 301, thus preventing the prosthesis 70 from expanding. Further, the mid shaft assembly 21 can be translated proximally with respect to the inner assembly 18 into the outer sheath assembly 22, thus exposing a first end 301 of the prosthesis 70 held within the outer retention member 42. In this way the outer retention member 42 can be used to help secure a prosthesis 70 to or release it from the delivery system 10. The outer retention member 42 can have a cylindrical or elongate tubular shape, and may be referred to as an outer retention ring, though the particular shape is not limiting.

The mid shaft hypotube 43 itself can be made of, for example, high density polyethylene (HDPE), as well as other appropriate materials as described herein. The mid shaft hypotube 43 can be formed of a longitudinally pre-compressed HDPE tube, which can provide certain benefits. For example, the pre-compressed HDPE tube can apply a force distally onto the outer retention member 42, thus preventing accidental, inadvertent, and/or premature release of the prosthesis 70. Specifically, the distal force by the mid shaft hypotube 43 keeps the distal end of the outer retention member 42 distal to the inner retention member 40, thus preventing the outer retention member 42 from moving proximal to the inner retention member 40 before it is desired by a user to release the prosthesis 70. This can remain true even when the delivery system 10 is bent/deflected at a sharp angle. Further disclosure for the outer retention member 42 and mid shaft hypotube 43 can be found in U.S. Pat. Pub. No. 2016/0317301, hereby incorporated by reference in its entirety.

As shown in FIG. 2A, the distal anchors 80 can be located in a delivered configuration where the distal anchors 80 point generally distally (as illustrated, axially away from the main body of the prosthesis frame and away from the handle of the delivery system). The distal anchors 80 can be restrained in this delivered configuration by the outer sheath assembly 22. Accordingly, when the outer sheath 22 is withdrawn proximally, the distal anchors 80 can flip positions (e.g., bend approximately 180 degrees) to a deployed configuration (e.g., pointing generally proximally). FIG. 2A also shows the proximal anchors 82 extending distally in their delivered configuration within the outer sheath assembly 22. In other embodiments, the distal anchors 80 can be held to point generally proximally in the delivered configuration and compressed against the body of the prosthesis frame.

The delivery system 10 may be provided to users with a prosthesis 70 preinstalled. In other embodiments, the prosthesis 70 can be loaded onto the delivery system shortly before use, such as by a physician or nurse.

Delivery System Assemblies

FIGS. 4-8 illustrate further views of delivery system 10 with different assemblies translated proximally and described in detail.

Figure 4:
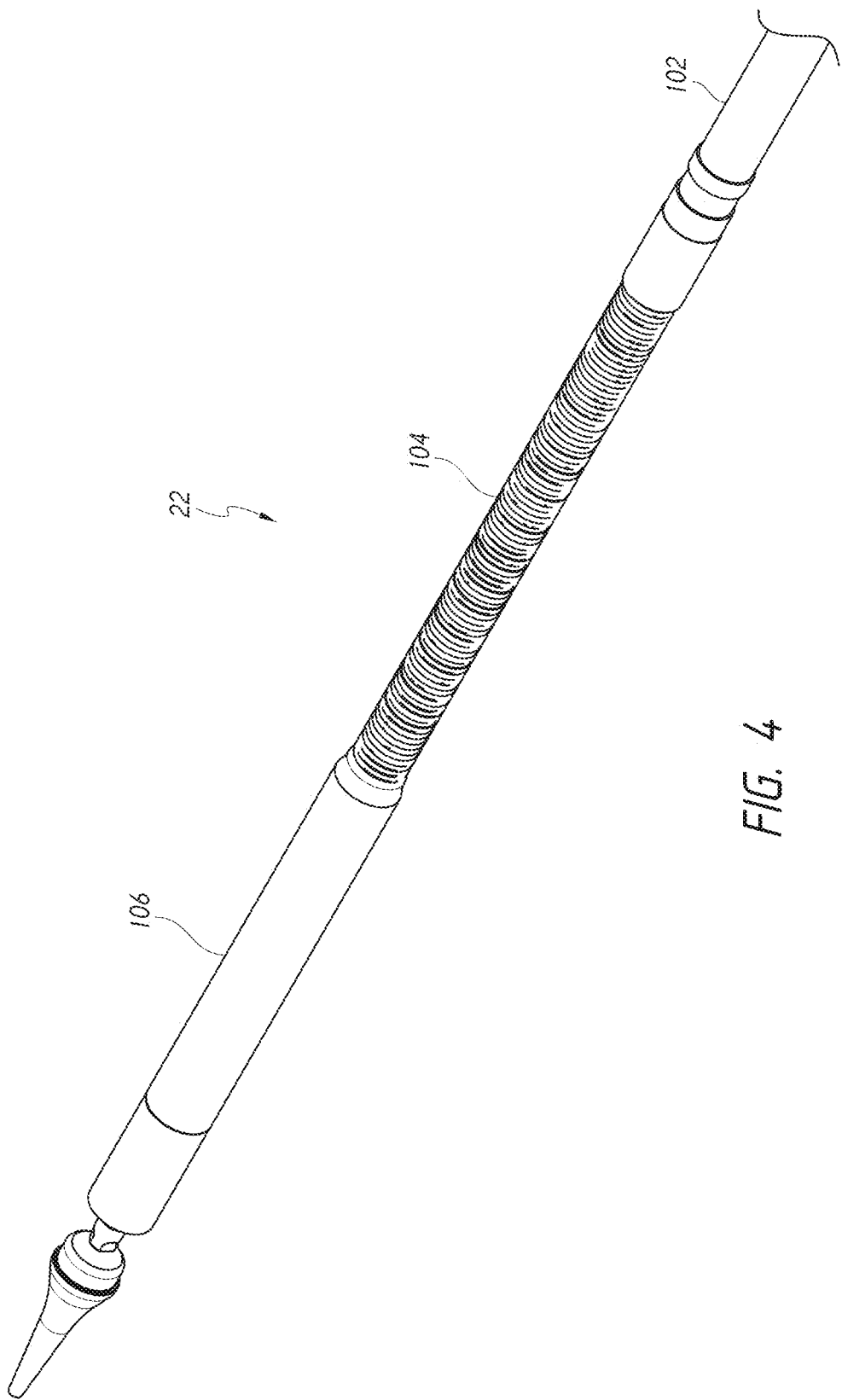
FIG. 4 shows a perspective view of the distal end of the delivery system of FIG. 1.

Starting with the outermost assembly shown in FIG. 4, the outer sheath assembly 22 can include an outer proximal shaft 102 directly attached to the handle 14 at its proximal end and an outer hypotube 104 attached at its distal end. A capsule 106 can then be attached generally at the distal end of the outer hypotube 104. In some embodiments, the capsule 106 can be 28 French or less in size. These components of the outer sheath assembly 22 can form a lumen for the other subassemblies to pass through.

The outer proximal shaft 102 may be a tube and is preferably formed of a plastic, but could also be a metal hypotube or other material. The outer hypotube 104 can be a metal hypotube which in some embodiments may be cut or have slots, as discussed in detail below. The outer hypotube 104 can be covered or encapsulated with a layer of ePTFE, PTFE, or other polymer/material so that the outer surface of the outer hypotube 104 is generally smooth.

A capsule 106 can be located at a distal end of the outer proximal shaft 102. The capsule 106 can be a tube formed of a plastic or metal material. In some embodiments, the capsule 106 is formed of ePTFE or PTFE. In some embodiments, this capsule 106 is relatively thick to prevent tearing and to help maintain a self-expanding implant in a compacted configuration. In some embodiments the material of the capsule 106 is the same material as the coating on the outer hypotube 104. As shown, the capsule 106 can have a diameter larger than the outer hypotube 104, though in some embodiments the capsule 106 may have a similar diameter as the hypotube 104. In some embodiments, the capsule 106 may include a larger diameter distal portion and a smaller diameter proximal portion. In some embodiments, there may be a step or a taper between the two portions. The capsule 106 can be configured to retain the prosthesis 70 in the compressed position within the capsule 106. Further construction details of the capsule 106 are discussed below.

The outer sheath assembly 22 is configured to be individually slidable with respect to the other assemblies. Further, the outer sheath assembly 22 can slide distally and proximally relative to the rail assembly 22 together with the mid shaft assembly 21, inner assembly 18, and nose cone assembly 31.

Figure 5:
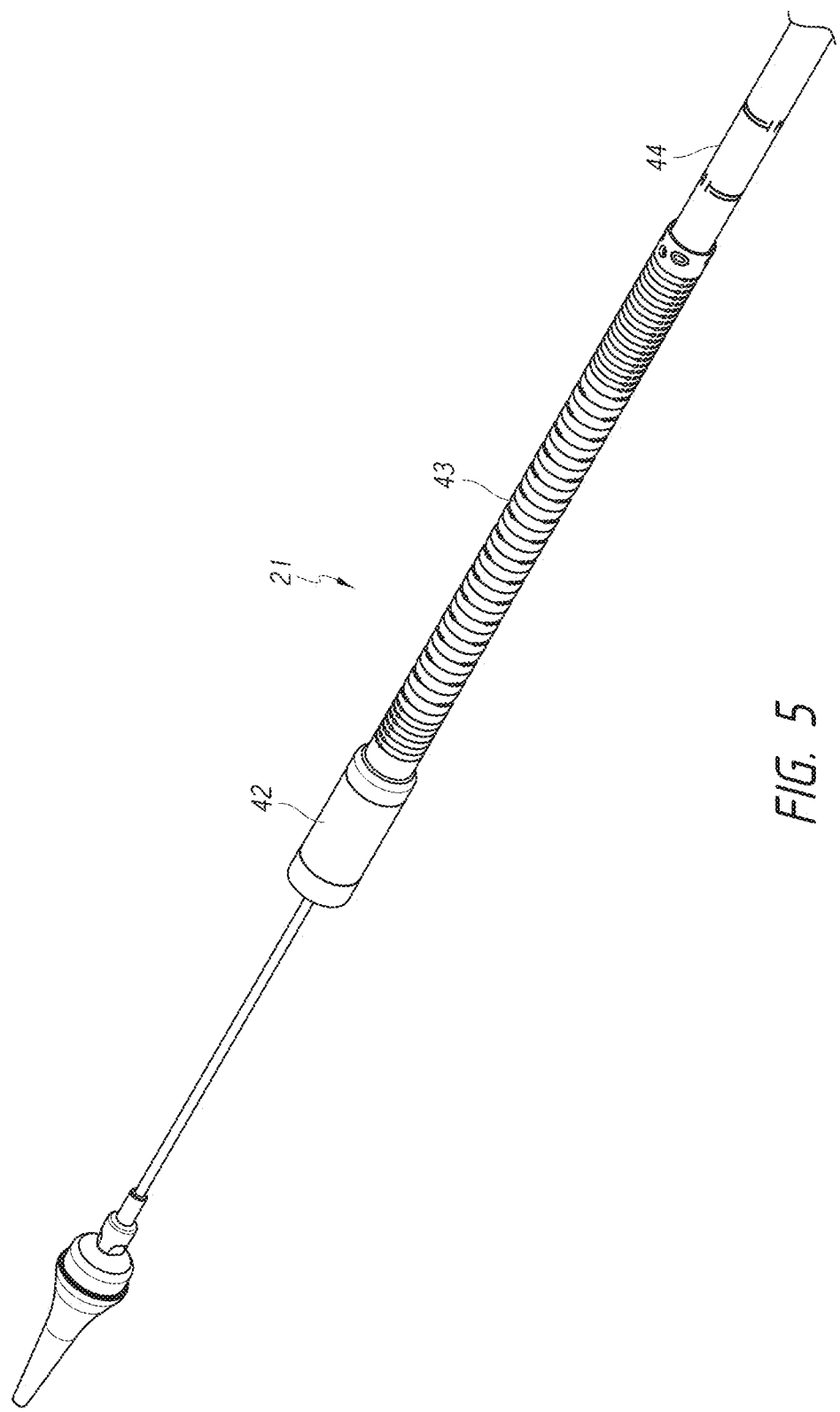
FIG. 5 show components of the delivery system of FIG. 4 with the outer sheath assembly moved proximally and out of view.

Moving radially inwardly, the next assembly is the mid shaft assembly 21. FIG. 5 shows a similar view as FIG. 4, but with the outer sheath assembly 22 removed, thereby exposing the mid shaft assembly 21.

The mid shaft assembly 21 can include a mid shaft hypotube 43 generally attached at its proximal end to a mid shaft proximal tube 44, which in turn can be attached at its proximal end to the handle 14, and an outer retention ring 42 located at the distal end of the mid shaft hypotube 43. Thus, the outer retention ring 42 can be attached generally at the distal end of the mid shaft hypotube 43. These components of the mid shaft assembly 21 can form a lumen for other subassemblies to pass through.

Similar to the other assemblies, the mid shaft hypotube 43 and/or mid shaft proximal tube 44 can comprise a tube, such as a hypodermic tube or hypotube (not shown). The tubes can be made from one of any number of different materials including Nitinol, stainless steel, and medical grade plastics. The tubes can be a single piece tube or multiple pieces connected together. Using a tube made of multiple pieces can allow the tube to provide different characteristics along different sections of the tube, such as rigidity and flexibility. The mid shaft hypotube 43 can be a metal hypotube which in some embodiments may be cut or have slots as discussed in detail below. The mid shaft hypotube 43 can be covered or encapsulated with a layer of ePTFE, PTFE, or other material so that the outer surface of the mid shaft hypotube 43 is generally smooth.

The outer retention ring 42 can be configured as a prosthesis retention mechanism that can be used to engage with the prosthesis 70, as discussed with respect to FIG. 2A. For example, the outer retention ring 42 may be a ring or covering that is configured to radially cover the struts 72 on the prosthesis 70. The outer retention ring 42 can also be considered to be part of the implant retention area 16, and may be at the proximal end of the implant retention area 16. With struts or other parts of a prosthesis 70 engaged with the inner retention member 40, discussed below the outer retention ring 42 can cover both the prosthesis 70 and the inner retention member 40 to secure the prosthesis 70 on the delivery system 10. Thus, the prosthesis 70 can be sandwiched between the inner retention member 40 of the inner shaft assembly 18 and the outer retention ring 42 of the mid shaft assembly 21.

The mid shaft assembly 21 is disposed so as to be individually slidable with respect to the other assemblies. Further, mid shaft assembly 21 can slide distally and proximally relative to the rail assembly 22 together with the outer sheath assembly 22, mid inner assembly 18, and nose cone assembly 31.

Figure 6A:
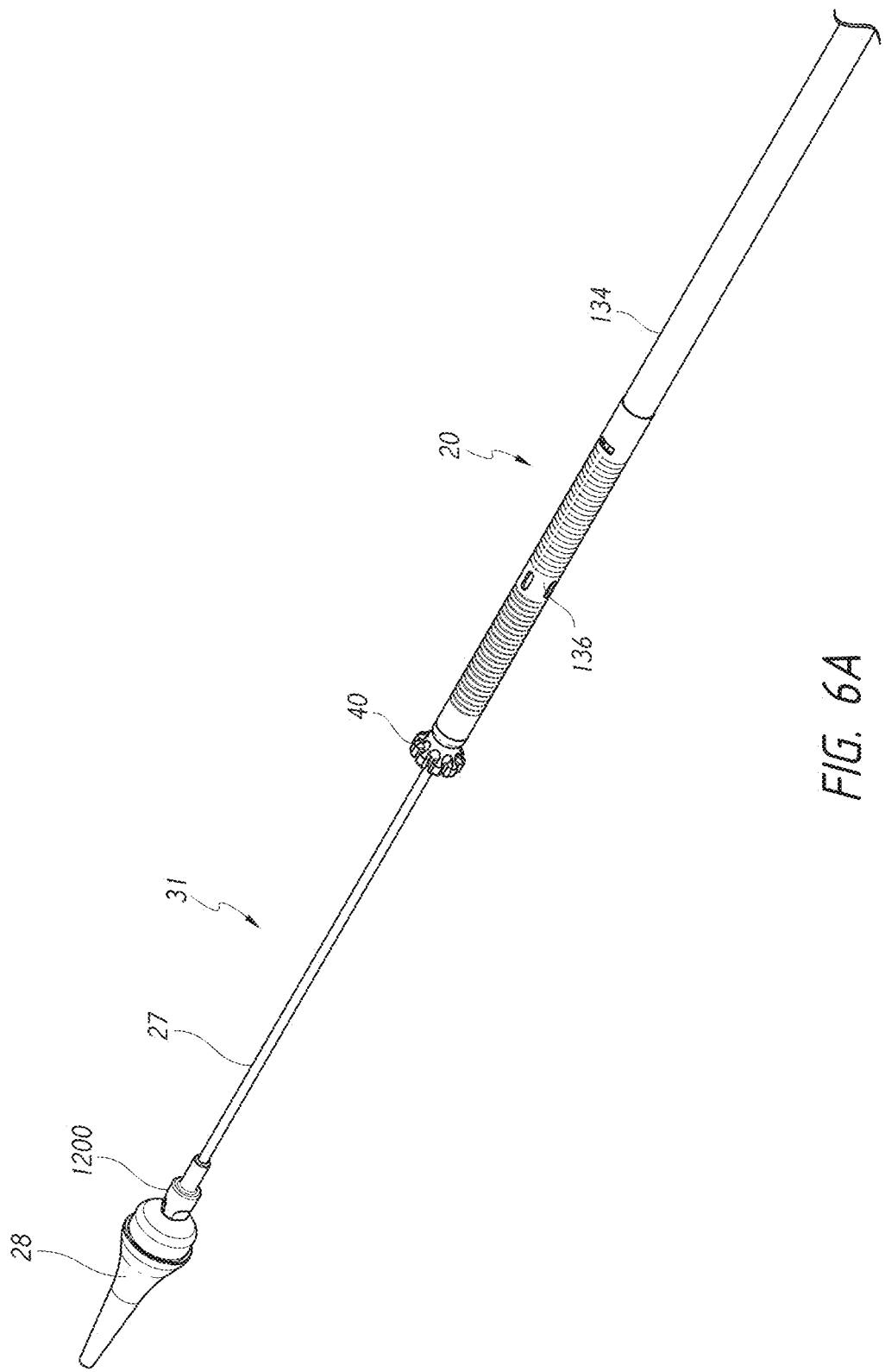
FIG. 6A show components of the delivery system of FIG. 5 with the mid shaft assembly moved proximally and out of view.
Figure 6B:
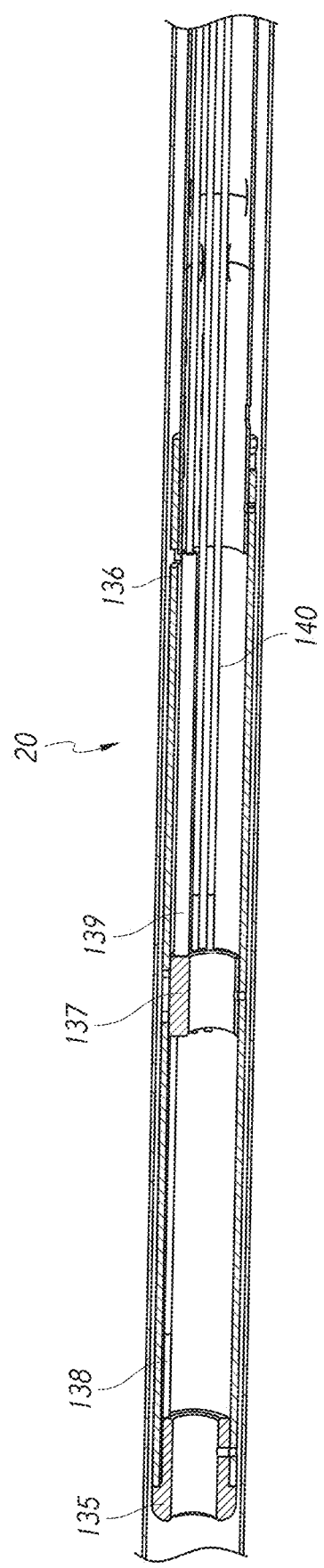
FIG. 6B illustrates a cross-section of the rail assembly.

Next, radially inwardly of the mid shaft assembly 21 is the rail assembly 20. FIG. 6A shows approximately the same view as FIG. 5, but with the mid shaft assembly 21 removed, thereby exposing the rail assembly 20. FIG. 6B further shows a cross-section of the rail assembly 20 to view the pull wires. The rail assembly 20 can include a rail shaft 132 (or rail) generally attached at its proximal end to the handle 14. The rail shaft 132 can be made up of a rail proximal shaft 134 directly attached to the handle at a proximal end and a rail hypotube 136 attached to the distal end of the rail proximal shaft 134. The rail hypotube 136 can further include an atraumatic rail tip at its distal end. Furth, the distal end of the rail hypotube 136 can abut a proximal end of the inner retention member 40, as shown in FIG. 6. In some embodiments, the distal end of the rail hypotube 136 can be spaced away from the inner retention member 40. These components of the rail shaft assembly 20 can form a lumen for the other subassemblies to pass through.

As shown in FIG. 6B, attached to an inner surface of the rail hypotube 136 are one or more pull wires which can be used apply forces to the rail hypotube 136 and steer the rail assembly 20. The pull wires can extend distally from the knobs in the handle 14, discussed below, to the rail hypotube 136. In some embodiments, pull wires can be attached at different longitudinal locations on the rail hypotube 136, thus providing for multiple bending locations in the rail hypotube 136, allowing for multidimensional steering.

In some embodiments, a distal pull wire 138 can extend to a distal section of the rail hypotube 136 and two proximal pull wires 140 can extend to a proximal section of the rail hypotube 136, however, other numbers of pull wires can be used, and the particular amount of pull wires is not limiting. For example, a two pull wires can extend to a distal location and a single pull wire can extend to a proximal location. In some embodiments, ring-like structures attached inside the rail hypotube 136, known as pull wire connectors, can be used as attachment locations for the pull wires, such as proximal ring 137 and distal ring 135. In some embodiments, the rail assembly 20 can include a distal pull wire connector 135 and a proximal pull wire connector 139. In some embodiments, the pull wires can directly connect to an inner surface of the rail hypotube 136.

The distal pull wire 138 can be connected (either on its own or through a connector 135) generally at the distal end of the rail hypotube 136. The proximal pull wires 140 can connect (either on its own or through a connector 137) at a location approximately one quarter, one third, or one half of the length up the rail hypotube 136 from the proximal end. In some embodiments, the distal pull wire 138 can pass through a small diameter pull wire lumen 139 (e.g., tube, hypotube, cylinder) attached on the inside of the rail hypotube 136. This can prevent the wires 138 from pulling on the rail hypotube 136 at a location proximal to the distal connection. Further, the lumen 139 can act as compression coils to strengthen the proximal portion of the rail hypotube 136 and prevent unwanted bending. Thus, in some embodiments the lumen 139 is only located on the proximal half of the rail hypotube 136. In some embodiments, multiple lumens 139, such as spaced longitudinally apart or adjacent, can be used per distal wire 139. In some embodiments, a single lumen 139 is used per distal wire 139. In some embodiments, the lumen 139 can extend into the distal half of the rail hypotube 136. In some embodiments, the lumen 139 is attached on an outer surface of the rail hypotube 136. In some embodiments, the lumen 139 is not used.

For the pair of proximal pull wires 140, the wires can be spaced approximately 180° from one another to allow for steering in both directions. Similarly, if a pair of distal pull wires 138 is used, the wires can be spaced approximately 180° from one another to allow for steering in both directions. In some embodiments, the pair of distal pull wires 138 and the pair of proximal pull wires 140 can be spaced approximately 90° from each other. In some embodiments, the pair of distal pull wires 138 and the pair of proximal pull wires 140 can be spaced approximately 0° from each other. However, other locations for the pull wires can be used as well, and the particular location of the pull wires is not limiting. In some embodiments, the distal pull wire 138 can pass through a lumen 139 attached within the lumen of the rail hypotube 136. This can prevent an axial force on the distal pull wire 138 from creating a bend in a proximal section of the rail hypotube 136.

The rail assembly 20 is disposed so as to be slidable over the inner shaft assembly 18 and the nose cone assembly 31. In some embodiments, the outer sheath assembly 22, the mid shaft assembly 21, the inner shaft assembly 22, and the nose cone assembly 31 can be configured to slide together along or relative to the rail assembly 20, such as proximally and distally with or without any bending of the rail assembly 20. In some embodiments, the outer sheath assembly 22, the mid shaft assembly 21, the inner shaft assembly 22, and the nose cone assembly 31 can be configured to retain the implant 70 in a compressed position when they are simultaneously slid along or relative to the rail assembly 20.

Figure 7:
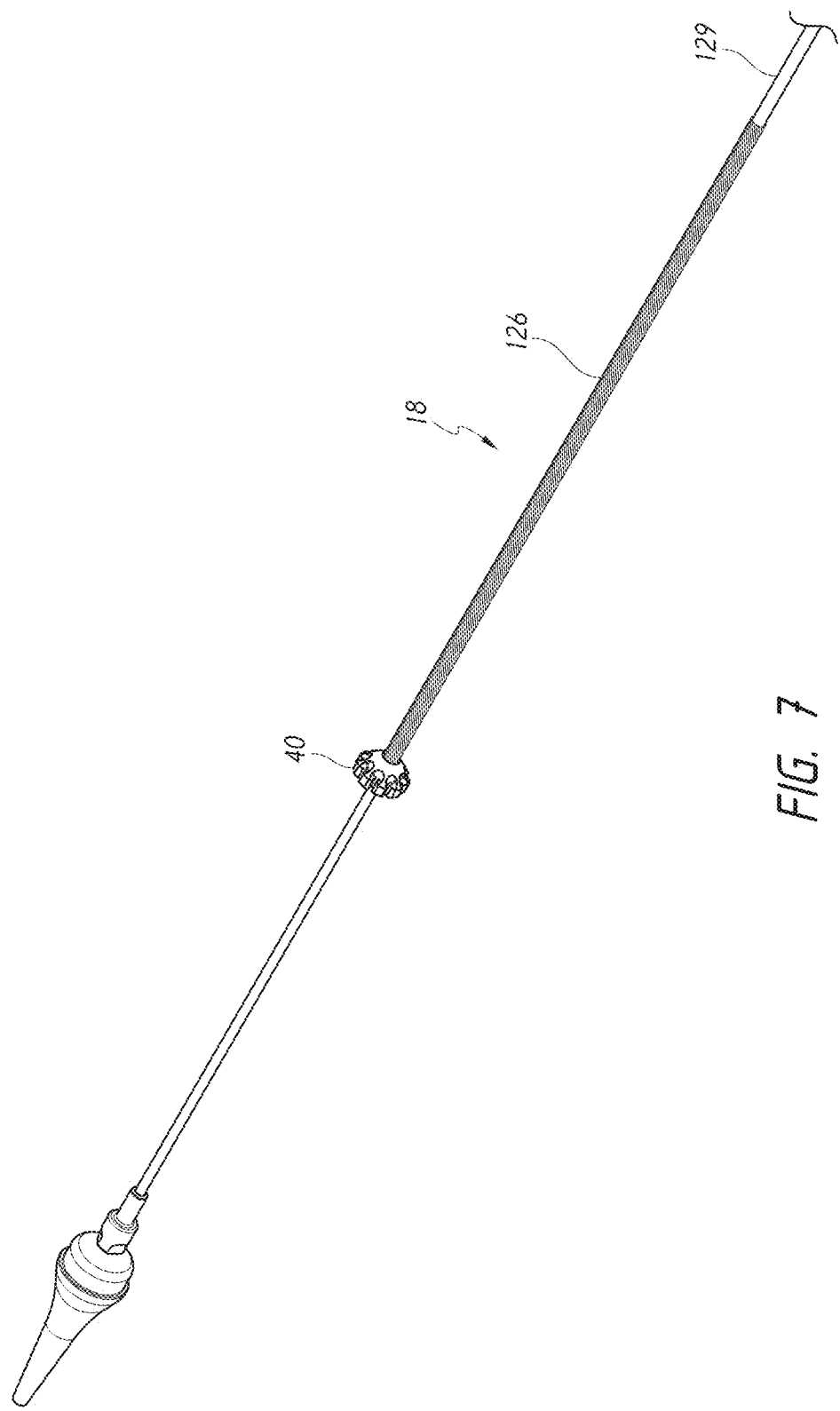
FIG. 7 show components of the delivery system of FIG. 6A with the rail assembly moved proximally and out of view.

Moving radially inwards, the next assembly is the inner shaft assembly 18. FIG. 7 shows approximately the same view as FIG. 6A, but with the rail assembly 20 removed, thereby exposing the inner shaft assembly 18.

The inner shaft assembly 18 can include an inner shaft 122 generally attached at its proximal end to the handle 14, and an inner retention ring 40 located at the distal end of the inner shaft 122. The inner shaft 122 itself can be made up of an inner proximal shaft 124 directly attached to the handle 14 at a proximal end and a distal section 126 attached to the distal end of the inner proximal shaft 124. Thus, the inner retention ring 40 can be attached generally at the distal end of the distal section 126. These components of the inner shaft assembly 18 can form a lumen for the other subassemblies to pass through.

Similar to the other assemblies, the inner proximal shaft 124 can comprise a tube, such as a hypodermic tube or hypotube (not shown). The tube can be made from one of any number of different materials including Nitinol, cobalt chromium, stainless steel, and medical grade plastics. The tube can be a single piece tube or multiple pieces connected together. A tube comprising multiple pieces can provide different characteristics along different sections of the tube, such as rigidity and flexibility. The distal section 126 can be a metal hypotube which in some embodiments may be cut or have slots as discussed in detail below. The distal section 126 can be covered or encapsulated with a layer of ePTFE, PTFE, or other material so that the outer surface of the distal section 126 is generally smooth.

The inner retention member 40 can be configured as a prosthesis retention mechanism that can be used to engage with the prosthesis 70, as discussed with respect to FIG. 2A. For example, the inner retention member 40 may be a ring and can include a plurality of slots configured to engage with struts 72 on the prosthesis 70. The inner retention member 40 can also be considered to be part of the implant retention area 16, and may be at the proximal end of the implant retention area 16. With struts or other parts of a prosthesis 70 engaged with the inner retention member 40, the outer retention ring 42 can cover both the prosthesis and the inner retention member 40 to secure the prosthesis on the delivery system 10. Thus, the prosthesis 70 can be sandwiched between the inner retention member 40 of the inner shaft assembly 18 and the outer retention ring 42 of the mid shaft assembly 21.

The inner shaft assembly 18 is disposed so as to be individually slidable with respect to the other assemblies. Further, the inner assembly 18 can slide distally and proximally relative to the rail assembly 22 together with the outer sheath assembly 22, mid shaft assembly 21, and nose cone assembly 31.

Figure 8:
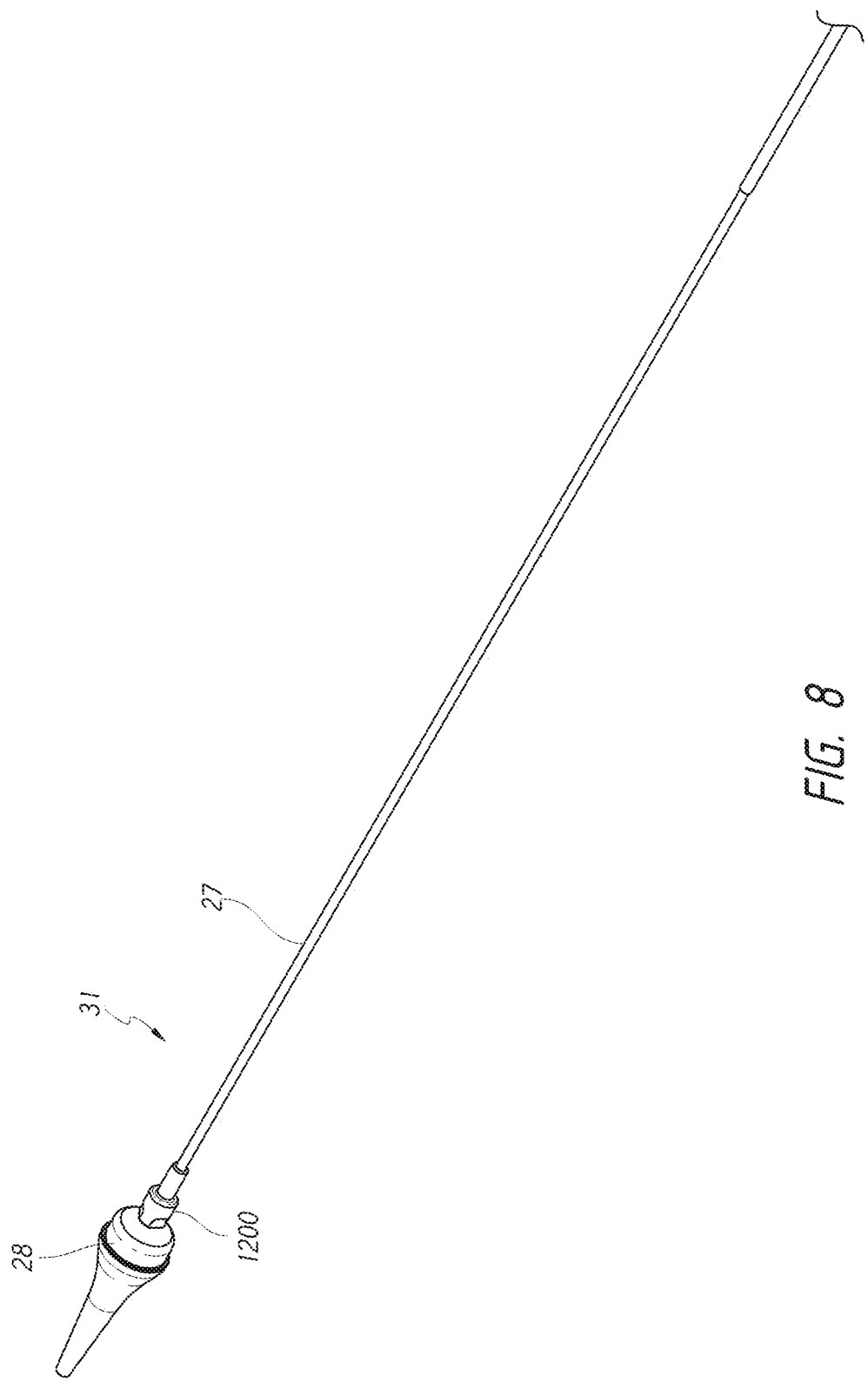
FIG. 8 show components of the delivery system of FIG. 7 with the inner assembly moved proximally and out of view.

Moving further inwardly from the inner shaft assembly 18 is the nose cone assembly 31 also seen in FIG. 8. This may be a nose cone shaft 27, and in some embodiments, may have a nose cone 28 on its distal end. The nose cone 28 can be made of polyurethane for atraumatic entry and to minimize injury to venous vasculature. The nose cone 28 can also be radiopaque to provide for visibility under fluoroscopy.

The nose cone shaft 27 may include a lumen sized and configured to slidably accommodate a guide wire so that the delivery system 10 can be advanced over the guide wire through the vasculature. However, embodiments of the system 10 discussed herein may not use a guide wire and thus the nose cone shaft 27 can be solid. The nose cone shaft 27 may be connected from the nose cone 28 to the handle, or may be formed of different segments such as the other assemblies. Further, the nose cone shaft 27 can be formed of different materials, such as plastic or metal, similar to those described in detail above.

In some embodiments, the nose cone shaft 27 includes a guide wire shield 1200 located on a portion of the nose cone shaft 27. Examples of such a guide wire shield can be found in FIGS. 9A-B. In some embodiments, the guide wire shield 1200 can be proximal to the nose cone 28. In some embodiments, the guide wire shield 1200 can be translatable along the nose cone shaft 27. In some embodiments, the guide wire shield 1200 can be locked in place along the nose cone shaft 27. In some embodiments, the guide wire shield 1200 can be at least partially located within the nose cone 28.

Advantageously, the guide wire shield 1200 can allow for smooth tracking of the guide wire with the implant 70 loaded, and can provide a large axial diameter landing zone for a distal end of the implant so that the distal end of the implant 70 may spread out properly and be arranged in a uniform radial arrangement. This uniformity allows for proper expansion. Furthermore, the guide wire shield 1200 can prevent kinking or damaging of the nose cone shaft 27 during compression/crimping of the prosthesis 70, which can exert a large compressive force on the nose cone shaft 27. As the prosthesis 70 can be crimped onto the guide wire shield 1200 instead of directly on the nose cone shaft 27, the guide wire shield 1200 can provide a protective surface.

Figure 9A:
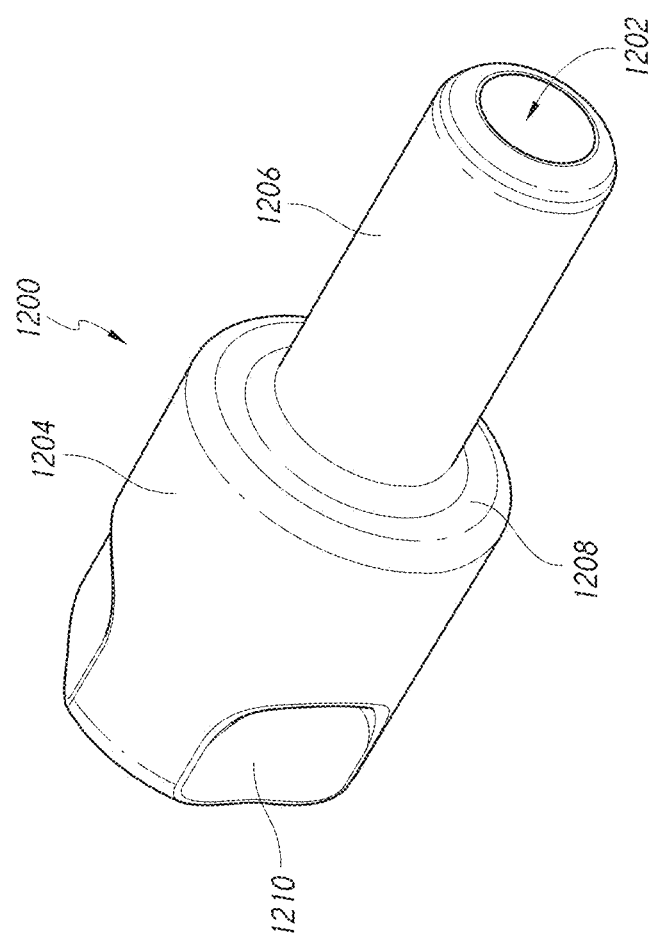
FIGS. 9A and 9B illustrate embodiments of a guide wire shield.

As shown, the guide wire shield 1200 can include a lumen 1202 configured to surround the nose cone shaft 27. The guide wire shield 1200 can include a larger diameter distal end 1204 and a smaller diameter proximal end 1206. In some embodiments, the dimension change between the two ends can be tapered, or can be a step 1208 such as shown in FIG. 9A. The distal end 1204 can include a number of indents 1210 for easier gripping by a user, but may not be included in all embodiments. The proximal end 1206 and the distal end 1204 can both be generally cylindrical, but the particular shape of the guide wire shield 1200 is not limiting.

The distal end of the prosthesis 70 can be crimped so that it is radially in contact with the proximal end 1206 of the guide wire shield 1200. This can allow the prosthesis 70 to be properly spread out around an outer circumference of the proximal end 1206 of the guide wire shield 1200. In some embodiments, the distal end of the prosthesis 70 can longitudinally abut against the proximal end of the distal end 1204 (e.g., at the step 1208), thus providing a longitudinal stop.

Figure 9B:
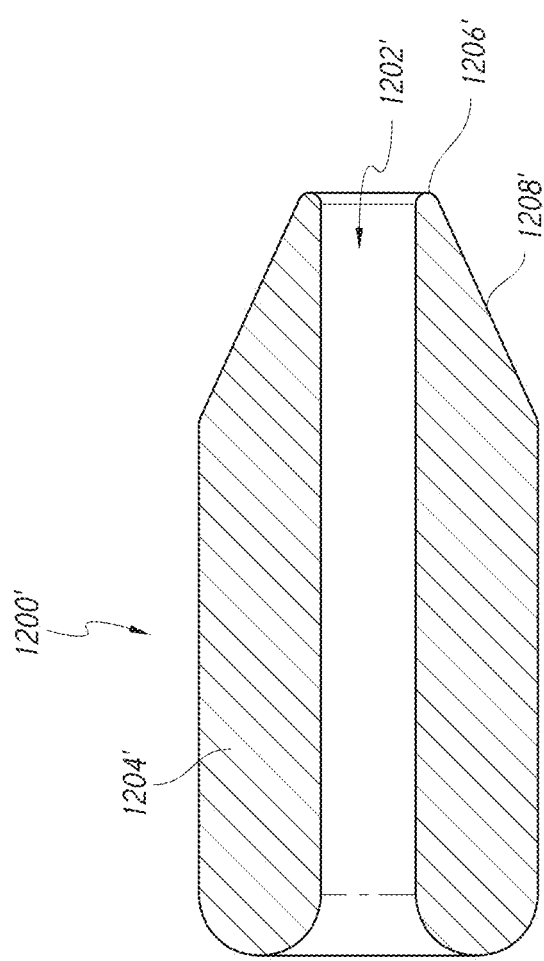

FIG. 9B shows an alternate embodiment of a guide wire shield 1200' having a more tapered configuration. As shown, the proximal end 1206' of the guide wire shield 1200' can be a single radially outward taper 1208' to the distal end 1204' of the guide wire shield 1200', which can be generally cylindrical. The guide wire shield 1200' can also include a lumen 1202' for receiving the nose cone shaft 27.

The nose cone assembly 31 is disposed so as to be individually slidable with respect to the other assemblies. Further, the nose cone assembly 31 can slide distally and proximally relative to the rail assembly 22 together with the outer sheath assembly 22, mid shaft assembly 21, and inner assembly 18.

In some embodiments, one or more spacer sleeves (not shown) can be used between different assemblies of the delivery system 10. For example, a spacer sleeve can be located concentrically between the mid shaft assembly and the rail assembly 20, generally between the mid 43 and rail hypotubes 136. In some embodiments, the spacer sleeve can be generally embedded in the hypotube 43 of the mid shaft assembly 21, such as on an inner surface of the mid shaft assembly 21. In some embodiments, a spacer sleeve can be located concentrically between the rail assembly 20 and the inner assembly 18, generally within the rail hypotube 136. In some embodiments, a spacer sleeve can be used between the outer sheath assembly 22 and the mid shaft assembly 21. In some embodiments, a spacer sleeve can be used between the inner assembly 18 and the nose cone assembly 31. In some embodiments, 4, 3, 2, or 1 of the above-mentioned spacer sleeves can be used. The spacer sleeves can be used in any of the above positions.

The spacer sleeve can be made of a polymer material such as braided Pebax® and can be lined, for example with PTFE, on the inner diameter, though the particular material is not limiting. The spacer sleeve can advantageously reduce friction between the steerable rail assembly 20 and its surrounding assemblies. Thus, the spacer sleeves can act as a buffer between the rail assembly 20 and the inner/nose cone assembly 18/30. Further, the spacer sleeve can take up any gap in radius between the assemblies, preventing compressing or snaking of the assemblies during steering. In some embodiments, the spacer sleeve may include cuts or slots to facilitate bending of the spacer sleeve. In some embodiments, the spacer sleeve may not include any slots, and may be a smooth cylindrical feature.

The spacer sleeve can be mechanically contained by the other lumens and components, and is thus not physically attached to any of the other components, allowing the spacer sleeve to be "floating" in that area. The floating aspect of the spacer sleeve allows it to move where needed during deflection and provide a support and/or lubricious bear surface/surfaces. Accordingly, the floating aspect allows the delivery system 10 to maintain flex forces. However, in some embodiments, the spacer sleeve can be connected to other components.

Hypotube/Shaft Construction

As discussed above, the outer sheath assembly 22, the mid shaft assembly 21, the inner assembly 18, and the rail assembly 20 can contain an outer hypotube 104, a mid shaft hypotube, a distal section 126, and a rail hypotube 136, respectively. Each of these hypotubes/sections/shafts can be laser cut to include a number of slots, thereby creating a bending pathway for the delivery system to follow. While different slot assemblies are discussed below, it will be understood that any of the hypotubes can have any of the slot configurations discussed below. FIGS. 10-14 show the different hypotubes in isolated format.

Figure 10:
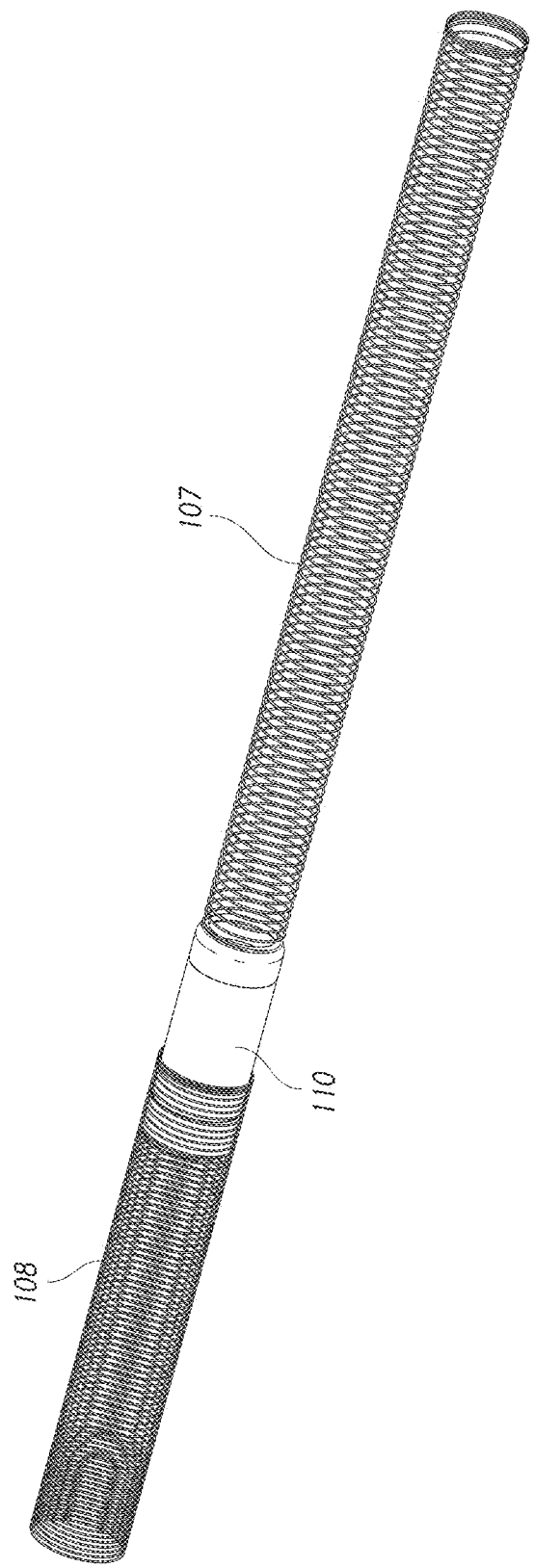
FIG. 10 illustrates an embodiment of an outer hypotube.

The outer hypotube 104, shown in FIG. 10, can be generally formed of a metal coil or a plurality of metal coils. In some embodiments, the outer hypotube 104 can be formed of a proximal metal coil 107 and a distal metal coil 108. The proximal metal coil 107 and the distal metal coil 108 can be longitudinally separated by a tube portion 110, such as shown in FIG. 10. However, in some embodiments the proximal metal coil 107 and the distal metal coil 108 connect. The proximal metal coil 107 and the distal metal coil 108 can be connected to an outer surface of the tube portion 110, for example at the distal end of the proximal metal coil 107 and a proximal end of the distal metal coil 108, in order to form the full outer hypotube 104. In some embodiments, the proximal metal coil 107 and the distal metal coil 108 are generally the same. In some embodiments, the proximal metal coil 107 and the distal metal coil 110 are different, for example in spacing between coils, curvature, diameter, etc. In some embodiments, the distal metal coil 108 has a larger diameter than the proximal metal coil 107, such as when the distal metal coil 108 forms the large diameter of the capsule 106. In some embodiments, they have the same diameter. In some embodiments, one or both of the metal coils 108/107 can form the capsule 106. The coils can be coated by polymer layers, such as described in detail below regarding the capsule construction. The coil construction can allow the outer hypotube 104 to follow the rail in any desired direction.

Figure 11:
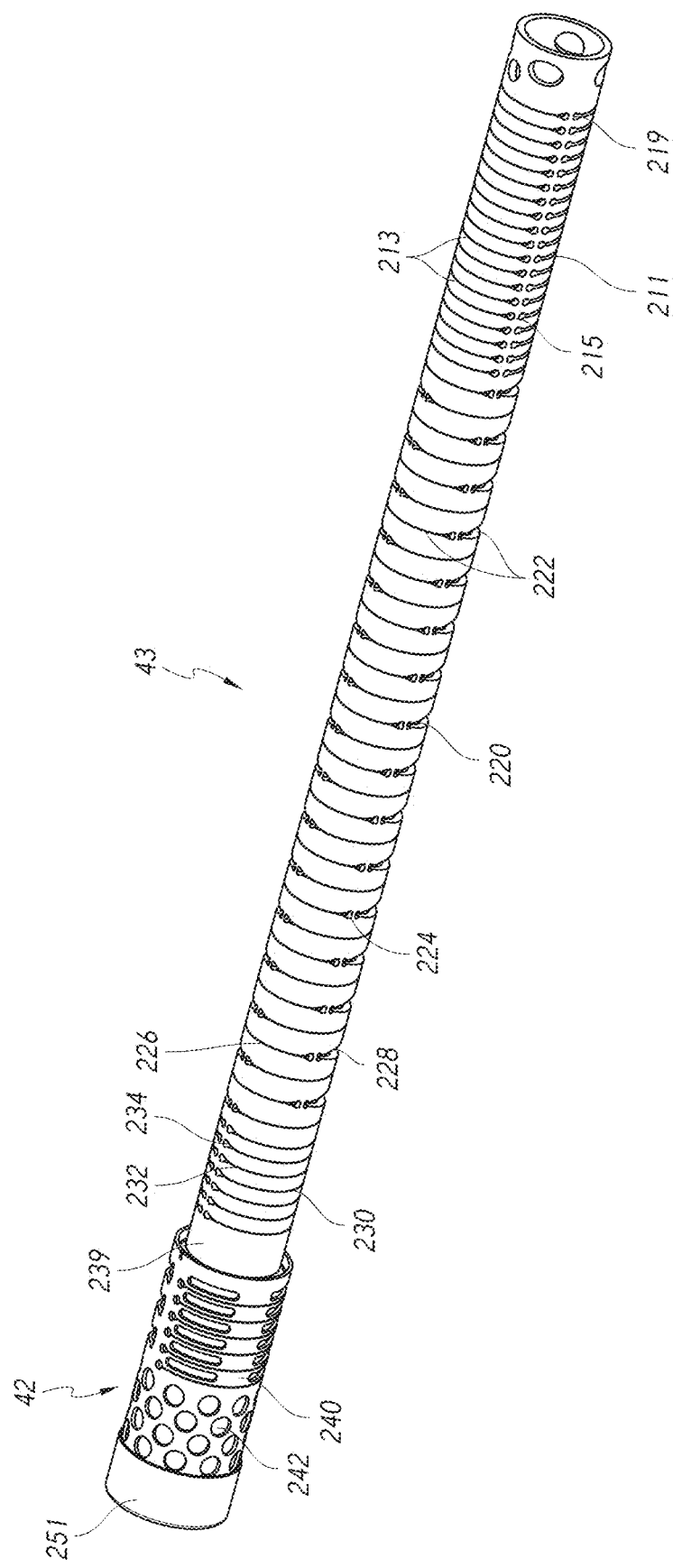
FIG. 11 illustrates an embodiment of a mid shaft hypotube.
Figure 12A:
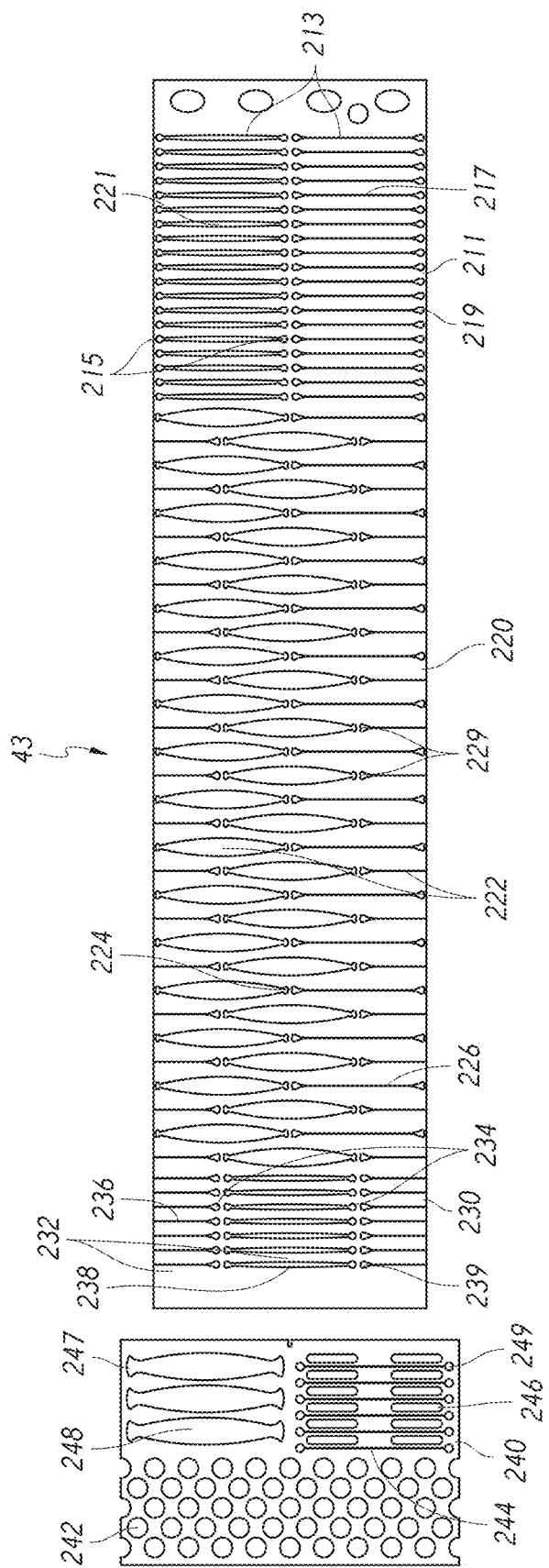
FIG. 12A illustrates an embodiment of the mid shaft hypotube of FIG. 11 as a flat pattern.

Moving radially inwardly, FIGS. 11-12B shows that the mid shaft hypotube 43 can be a metal laser cut hypotube, such as a lasercut Nitinol hypotube. FIG. 12A illustrates a flat pattern of FIG. 11. As shown in the figures, the hypotube 43 can have a number of slots/apertures cut into the hypotube. In some embodiments, the cut pattern can be the same throughout. In some embodiments, the mid shaft hypotube 43 can have different sections having different cut patterns.

For example, the proximal end of the mid shaft hypotube 43 can be a first section 210 having a plurality circumferentially extending slot pairs 213 spaced longitudinally along the first section 211. Generally, two slots are cut around each circumferential location forming almost half of the circumference. Accordingly, two backbones 215 are formed between the slots 213 extending up the length of the first section 211. The slot pairs 213 can be composed of a first thin slot 217. A second slot 221 of each of the slot pairs 213 can be thicker than the first slot 217, such as 1, 2, 3, 4, or 5 times thicker. In some embodiments, the second slot 217 can be generally the same longitudinal thickness throughout the slot. Each of the slots of the slot pair 213 can end in a teardrop shape 219 in some embodiments to facilitate bending.

Moving distally, the mid shaft hypotube 43 can include a second section 220 having a number of slot pairs 222. Similar to the first section 211, the second section 220 can have a plurality of circumferentially extending slots spaced longitudinally along the second section 220. Generally, two slots (e.g., one slot pair 222) are cut around each circumferential location, forming almost half of a circumference. Accordingly, "backbones" 224 can be formed between the slots extending up the length of the second section 220. Each slot pair 222 can include a first slot 226 that is generally thin and has no particular shape (e.g., it can look the same as the slots 213 in the first section 211), and a second slot 228 that is significantly longitudinally thicker than the first slot 226. The second slot 228 can be narrower at its ends and longitudinally thicker in its middle portion, thereby forming a curved slot. Moving longitudinally along the second section 220, each slot pair 222 can be offset approximately 45 or 90 degrees as compared to longitudinally adjacent slot pairs 222. In some embodiments, a second slot pair 222 is offset 90 degrees from an adjacent first slot pair 222, and a third slot pair 222 adjacent the second slot pair 222 can have the same configuration of the first slot pair 222. This repeating pattern can extend along a length of the second section 220, thereby providing a particular bending direction induced by the second slot 228 of the slot pairs 222. Accordingly, the "backbone" 224 shifts circumferential position due to the offsetting of adjacent shifting slot pairs 222. Each of the slots of the slot pair 222 can end in a teardrop shape 229 in some embodiments to facilitate bending.

Moving distally, the mid shaft hypotube 43 can have a third section 230 having a number of slots. The outer retention ring 240 can be attached to a distal end of the third section 230. The third section 230 can have circumferentially extending slot pairs 232, each slot on the slot pair extending about half way along the circumference to form the two backbones 234. The slot pairs 232 can be composed of a first thin slot 236, similar to the slots 213 discussed in the first section 211. A second slot 238 of each of the slot pairs 232 can be thicker than the first slot 236, such as 1, 2, 3, 4, or 5 times thicker. In some embodiments, the second slot 238 can be generally the same longitudinal thickness throughout the slot, unlike the second slot 228 of the second section 220. The first slots 236 and the second slots 238 can be circumferentially aligned along a length of the third section 230 so that all of the first slots 236 are in the same circumferential position and all of the second slots 238 are in the same circumferential position. The second slots 238 can be aligned with one of the circumferential positions of the second slots 228 of the second section 220. Each of the slots of the slot pair 232 can end in a teardrop shape 239 in some embodiments to facilitate bending.

In some embodiments, an outer retention ring strengthener 240 which can partially or fully circumferentially surround the outer retention member 40 can have a number of slots/holes/apertures as well, such as shown in FIGS. 11-12. This can allow it to bend over curves, especially tight curves. In some embodiments, the distal end of the strengthener 240 includes a number of generally circular/elliptical holes 242. This can last for approximately half of the length of the strengthener 240. On the proximal half, one circumferential half of the strengthener 240 can include repeating thin slots 244 spaced by elongate ovoid holes 246. For example, two circumferentially spaced apart elongate ovoid holes 246 can be between each thin slot 244. Each of the slots 244 can end in a teardrop shape 249 in some embodiments to facilitate bending. On the other circumferential half of the proximal section, the strengthener 240 can include a number of large slots 248, for example 1, 2, 3, 4, or 5 large slots 248 spaced longitudinally apart. The large slots 248 can be larger in the middle and narrow towards each circumferential end. The large slots 248 may include ending expansions 247 to facilitate flexibility.

Additionally, the outer retention strengthener 240 can provide strength to lower deployment forces, protect the prosthesis 70 from any metal layers, and can add strength. In some embodiments, the liner can 240 be a polymer, such as PTFE, though the type of polymer or material is not limiting. In some embodiments, the strengthener 240 can be a metal. In some embodiments, the strengthener 240 can further include an outer polymer layer/jacket, such as a Pebax® jacket. This prevents the strengthener 240 from catching on the outer sheath assembly 22.

In certain embodiments, the outer retention ring 42 can further include an inner liner for smoothly transitioning over the prosthesis 70. The inner liner can be PTFE or etched PTFE, though the particular material is not limiting and other reduced friction polymers can be used. As shown in FIG. 12B, to prevent delamination during loading of the implant 70, the liner 251 may not be flush at the distal end of the outer retention ring 42. Instead, the liner 251 can be extended and inverted at the distal end in order to cover the distal end of the outer retention ring 42. In some embodiments, the liner 251 can cover an outer surface of the strengthener 240 as well. This can create a seamless rolled reinforced tip of the liner 251. The liner 251 can fully or partially cover an outer surface of the outer retention ring 42, for example ¼, ⅓, ½, ⅔, ¾ (or greater than ¼, ⅓, ½, ¾), or all of the outer retention ring 42. This solution is advantageous over previously known methods, such as disclosed in U.S. Pat. No. 6,622,367, incorporated by reference in its entirety, as PTFE lined applications do not adhere particularly well to reinforcements or the outer jacket. By inverting the liner 251 and fusing it to the outer retention ring 42 and/or the strengthener 240 and/or an outer polymer jacket on the strengthener 240/outer retention ring 42, this creates a seamless reinforced tip that can mitigate delamination. Delamination is a serious concern because the delaminated liner can tear and embolize during deployment, and the delaminated layer can cause extremely high loading and deployment forces. Delaminated layers can also cause lumen translation problems by locking up shafts thereby adding translational force requirements.

Figure 13:
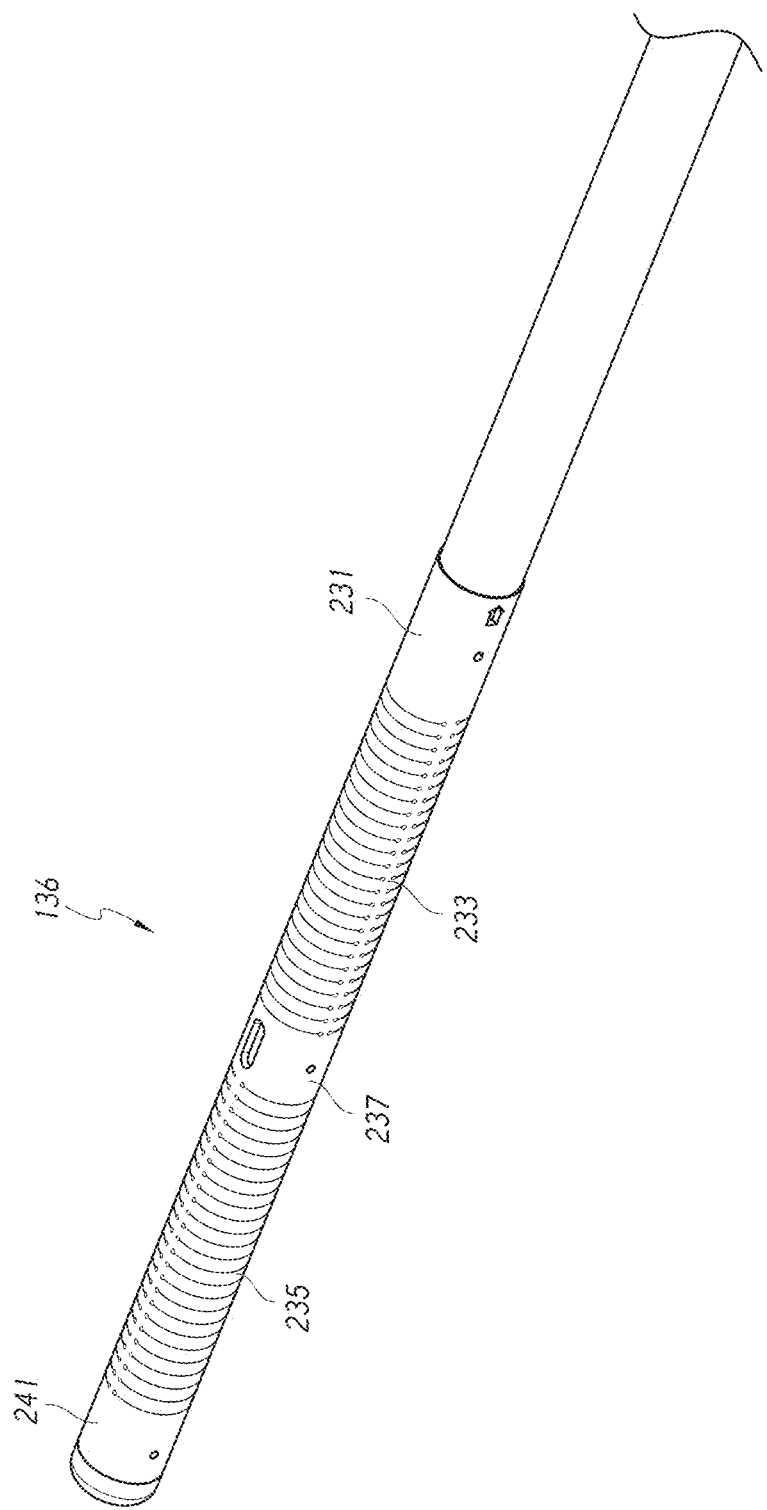
FIG. 13 illustrates an embodiment of a rail assembly.

Next, again moving radially inward, FIG. 13 shows an embodiment of the rail hypotube 136 (distal end towards the right). The rail hypotube 136 can also contain a number of circumferential slots. The rail hypotube 136 can generally be broken into a number of different sections. At the most proximal end is an uncut (or unslotted) hypotube section 231. Moving distally, the next section is the proximal slotted hypotube section 133. This section includes a number of circumferential slots cut into the rail hypotube 136. Generally, two slots are cut around each circumferential location forming almost half of the circumference. Accordingly, two backbones are formed between the slots extending up the length of the hypotube 136. This is the section that can be guided by the proximal pull wires 140. Moving further distally is the location 237 where the proximal pull wires 140 connect, and thus slots can be avoided. Thus section is just distal of the proximally slotted section.

Distally following the proximal pull wire connection area is the distal slotted hypotube section 235. This section is similar to the proximal slotted hypotube section 233, but has significantly more slots cut out in an equivalent length. Thus, the distally slotted hypotube section 235 provides easier bending than the proximally slotted hypotube section 233. In some embodiments, the proximal slotted section 233 can be configured to experience a bend of approximately 90 degrees with a half inch radius whereas the distal slotted section 135 can bend at approximately 180 degrees within a half inch. Further, as shown in FIG. 13, the spines of the distally slotted hypotube section 235 are offset from the spines of the proximally slotted hypotube section 233. Accordingly, the two sections will achieve different bend patterns, allowing for three-dimensional steering of the rail assembly 20. In some embodiments, the spines can be offset 30, 45, or 90 degrees, though the particular offset is not limiting. In some embodiments, the proximally slotted hypotube section 233 can include compression coils. This allows for the proximally slotted hypotube section 233 to retain rigidity for specific bending of the distally slotted hypotube section 235.

At the distalmost end of the distal slotted hypotube section 235 is the distal pull wire connection area 241 which is again a non-slotted section of the rail hypotube 136.

Figure 14:
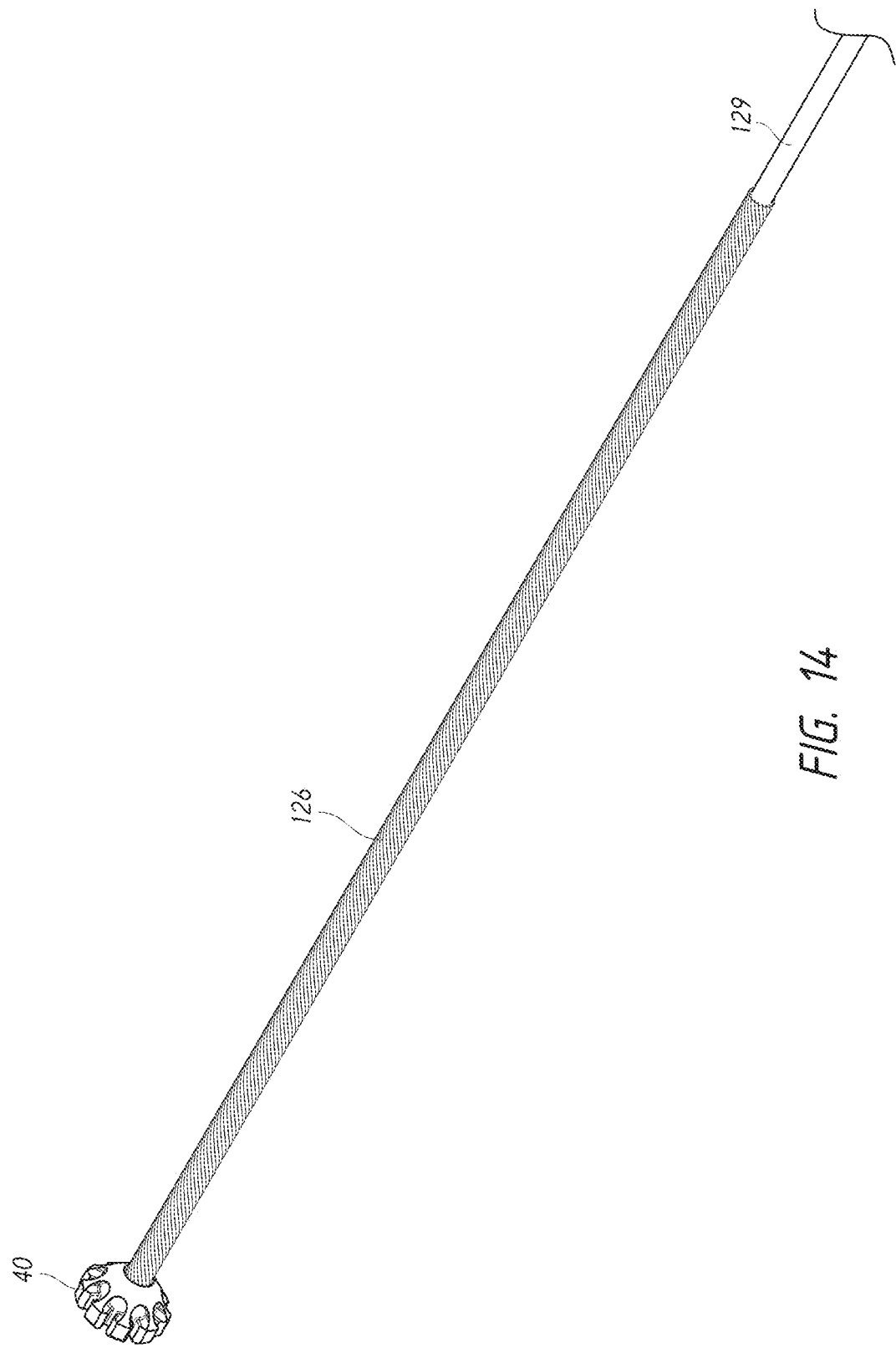
FIG. 14 illustrates an embodiment of an inner assembly.

Moving radially inwardly in FIG. 14, the inner assembly 18 is composed generally of two sections. The proximal section is a hypotube 129, either slotted or non-slotted. The distal section 126, which at least partially overlaps an outer surface of the proximal hypotube 129, can be designed to be particularly flexible. For example, the distal section 126 can be more flexible than any of the other shafts discussed herein. In some embodiments, the distal section 126 can be more flexible than any shaft discussed herein other than the nose cone shaft 27. In some embodiments, the distal section 126 can be a flexible tube or hypotube. In some embodiments, the distal section 126 can be a cable, such as a flexible cable. For example, the cable can several strands of wire, such as metal, plastic, polymer, ceramic, etc., wound together to form a rope or cable. Because the cable is so flexible, it can more easily bend with the rail assembly 20. Further, the cable can be smooth, which allows the rail assembly 20 to track over a smooth surface, eliminating the need for any inner liner on the rail assembly 20.

Capsule Construction

The capsule 106 can be formed from one or more materials, such as PTFE, ePTFE, polyether block amide (Pebax®), polyetherimide (Ultem®), PEEK, urethane, Nitinol, stainless steel, and/or any other biocompatible material. The capsule is preferably compliant and flexible while still maintaining a sufficient degree of radial strength to maintain a replacement valve within the capsule 106 without substantial radial deformation, which could increase friction between the capsule 106 and a replacement valve 70 contained therein. The capsule 106 also preferably has sufficient column strength to resist buckling of the capsule, and sufficient tear resistance to reduce or eliminate the possibility of replacement valve tearing and/or damaging the capsule 106. Flexibility of the capsule 106 can be advantageous, particularly for a transseptal approach. For example, while being retracted along a curved member, for example while tracking over a rail assembly as described herein, the capsule 106 can flex to follow the curved member without applying significant forces upon the curved member, which may cause the curved member to decrease in radius. More specifically, the capsule 106 can bend and/or kink as it is being retracted along such a curved member such that the radius of the curved member is substantially unaffected.

Figure 15:
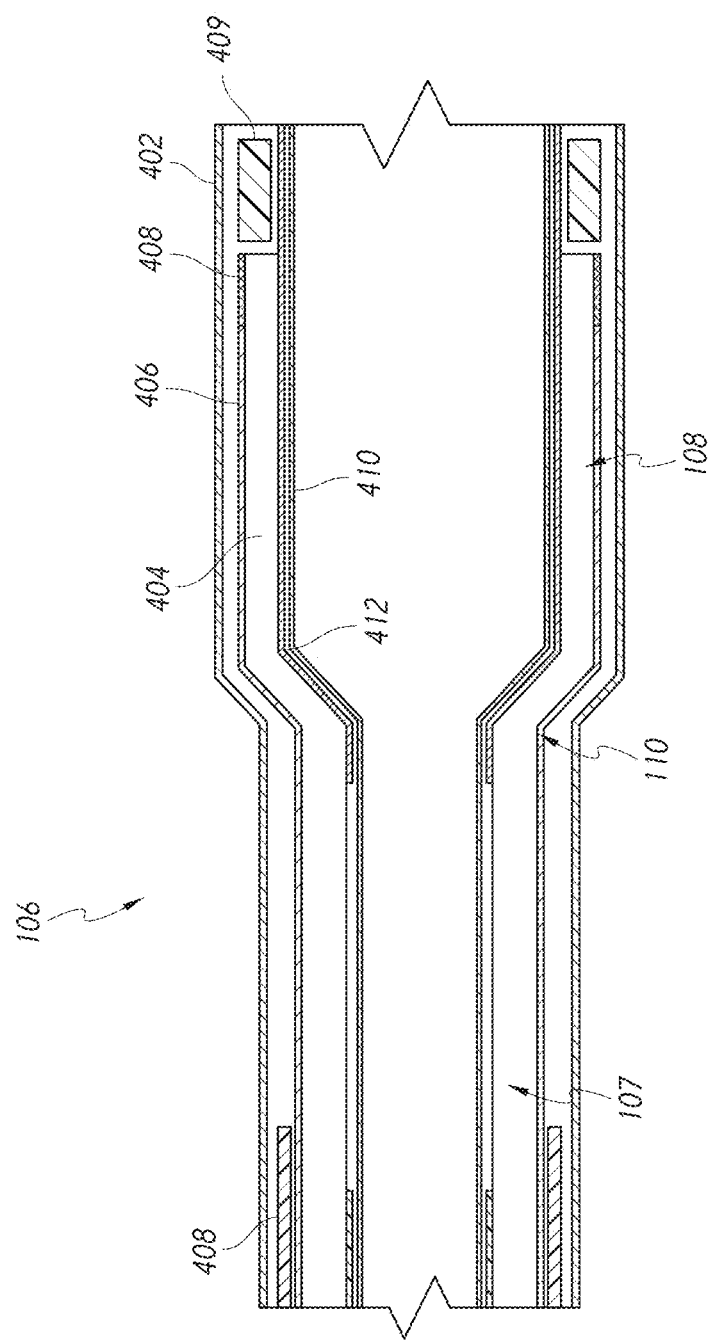
FIG. 15 illustrates a cross-section of a capsule.

FIG. 15 shows embodiments of a capsule 106 that can be used with embodiments of the delivery system 10. The capsule 106 may include any of the materials and properties discussed above. With many implant capsules, compression resistance and flexibility are typically balanced together, as improved flexibility can lead to worse compression resistance. Thus, there tends to be a choice made between compression resistance and flexibility. However, disclosed are embodiments of a capsule 106 that can achieve both high compression resistance as well as high flexibility. Specifically, the capsule 106 can bend in multiple directions.

In particular, a metal hypotube can provide radial strength and compression resistance, while specific slots/cuts in the hypotube can enable the flexibility of the capsule 106. In some embodiments, a thin liner and a jacket can surround the capsule 106, such as a polymer layer, to prevent any negative interactions between the implant 70 and the capsule 106.

In some embodiments, the capsule 106 can have a particular construction to allow for it to achieve advantageous properties, as shown in FIG. 15. The capsule 106 can be made of several different layers to provide such properties.

In some embodiments, the capsule 106 can be formed of a metal layer 402, which gives the capsule 106 its structure. This metal layer can include the coils discussed with respect to FIG. 10, or could be one or more hypotubes. The capsule 106 is then covered on an outer surface by a polymer layer and on an inner surface by a liner. All of these features are discussed in detail below.

As mentioned, the metal layer 404 can be, for example, a metal hypotube or laser cut hypotube. In some embodiments, the metal layer 404 can be a metal coil or helix, as discussed in detail above with respect to FIG. 10. Though not limiting, the metal layer 404 can have a thickness of 0.007 inches (or about 0.007 inches).

If a metal coil, such as shown in FIG. 10, is used, the coil dimensions can stay the same throughout a length of the metal layer 404. However, in some embodiments the coil dimensions can vary along a length of the metal layer 404. For example, the coils can vary between coils having a 0.014-inch gap with a 0.021-inch pitch (e.g., small coils), coils having a 0.020 inch-gap with a 0.02-inch pitch (e.g., large coils), and coils having a 0.020-inch gap with a 0.027-inch pitch (e.g., spaced large coils). However, these particular dimensions are merely examples, and other designs can be used as well.

The distalmost end of the metal layer 404 can be formed out of the small coils. Moving proximally, the metal layer 404 may then transition to a section of large coils, followed again by a section of small coils, and then finally the proximalmost section can be the spaced large coils. As an example set of lengths, though not limiting, the distalmost small coil section may have a length of 10 mm (or about 10 mm). Moving proximally, the adjacent large coil section may extend 40 mm (or about 40 mm) to 60 mm (or about 60 mm) in length. These two sections would be found in the distal metal coil 108 shown in FIG. 10. Moving to the proximal metal coil 107 shown in FIG. 10, the small coil section can have a length of 10 mm (or about 10 mm). The remaining portion of the proximal metal coil 107 can be the spaced large coil section. The spaced large coil section can have a length of 40 mm (or about 40 mm) to 60 mm (or about 60 mm) or greater.

As mentioned, the metal layer 404 (either coil or hypotube) can be covered by an outer polymer layer or jacket 402. In some embodiments, the outer polymer 402 layer is an elastomer, though the particular material is not limiting. In some embodiments, the outer polymer layer 402 can comprise polytetrafluoroethylene (PTFE) or expanded polytetrafluoroethylene (ePTFE). The ePTFE can have very different mechanical properties that PTFE. For example, ePTFE can be much more flexible while still maintaining good tensile/elongation properties. In some embodiments, the outer polymer layer 402 can comprise a thermoplastic elastomer, such as PEBAX®. In some embodiments, the outer polymer layer 402 can be pre-axially stressed before applying to the capsule. The outer polymer layer 402 can be approximately 0.006 to 0.008 inches in thickness, but the particular thickness is not limiting.

The outer polymer layer 402 can be applied to the metal layer 404 to form an outer jacket, such as by reflowing the polymer. In some embodiments, the outer polymer layer 402 can be directly applied to the metal layer 404. In some embodiments, an adhesive layer 406 can be disposed between the metal layer 404 and the outer polymer layer 402 to promote attachment of the outer polymer layer to the metal layer. For example, a fluoropolymer, or other soft durometer fluoroelastomer, can be applied between the metal layer 404 and the outer layer 402 in order to attach the two layers together and prevent delamination. In some embodiments, the adhesive layer 406 is not used.

In some implementations, other materials can be included between the metal layer 404 and the outer polymer layer 402 in order to improve properties. For example, fluorinated ethylene propylene (FEP) sections 408 can improve radial strength, in particular when the implant is under compression. While an FEP layer 408 is discussed as a particular material, other high strength polymers, metals, or ceramics can be used as well, and the particular material is not limiting. The FEP layer 408 can also act as an adhesive in some instances.

FEP sections 408 can be included at the distal and proximal ends of the capsule 106. The FEP sections 408 can either overlap the adhesive layer 406. Thus, FEP sections 408 can be located between the adhesive layer 406 and the metal layer 404 or between the adhesive layer 406 and the outer polymer layer 402. In some embodiments, the FEP sections 408 may be located in sections of the capsule 106 that do not include an adhesive layer 406.

The FEP section 408 located at the distal end of the capsule 106 can have a length of 10 mm (or about 10 mm), though the particular length is not limiting. In some embodiments, the FEP section 408 is approximately 0.003 inches in thickness, but the thickness may vary and is not limited by this disclosure. In some embodiments, different FEP sections 408 (e.g., a proximal section and a distal section) can have different thicknesses. In some embodiments, all FEP 408 layers have the same thickness. Example thicknesses can be 0.006 inches or 0.003 inches.

Moving to the inside of the metal layer 404, a liner 410 can be included on its radially inner surface. The liner 410 can be formed of a low friction and/or high lubricity material that allows for the capsule 106 to be translated over the prosthesis 70 without catching or damaging portions of the prosthesis 70. In some embodiments, the liner 410 can be PTFE, which can resist radial expansion and decrease friction with the prosthesis 70.

In some embodiments, the liner 410 is made from ePTFE. However, it can be difficult to reflow a standard ePTFE liner 410 on the inner layer of the capsule 106. Accordingly, the ePTFE liner layer 410 can be pre-compressed before applying onto the inner layer of the capsule 106. In some embodiments, portions of the outer polymer layer 402 and the liner 410 can be in contact with one another. Thus, prior to bonding the two layers together, the ePTFE liner 410 and/or outer polymer layer 402 can be axially compressed. Then, the layers can be bonded together with reflow techniques during manufacturing. For example, the ePTFE liner 410 can be axially compressed, such as over a mandrel, while the outer polymer layer 402 can be placed over it. These two layers can then be reflowed (e.g., melting under pressure) to connect. The combined layers can be slid into and/or around the metal layer 404 discussed herein, and can be melted under pressure again to form the final capsule 106.

This technique can allow for the capsule 106 to maintain flexibility and prevent breakage/tearing.

As mentioned above, the inner liner 410 can be ePTFE in some embodiments. The surface friction of ePTFE can be about 15% less than standard PTFE, and can be about 40% less than standard extruded thermoplastics that are used in the art.

In certain embodiments, the liner layer 410 can extend only along an inner surface of the capsule 106 and terminate at a distal end. However, to prevent delamination during loading of the implant 70, the liner 410 may not be flush at the distal end of the capsule 106. Instead, the liner 410 can be extended and inverted at the distal end in order to cover the distal end of the capsule 106 as well as an outer diameter of a portion of the outer polymer layer 402. This can create a seamless rolled reinforced tip of the liner 410. This solution is advantageous over previously known methods, such as disclosed in U.S. Pat. No. 6,622,367, incorporated by reference in its entirety, as PTFE lined applications do not adhere particularly well to reinforcements or the outer jacket. By inverting the liner 410 and fusing it with the outer polymer layer 402, this creates a seamless reinforced capsule tip that can mitigate delamination. Delamination is a serious concern because the delaminated liner can tear and embolize during deployment, and the delaminated layer can cause extremely high loading and deployment forces. Delaminated layers can also cause lumen translation problems by locking up shafts thereby adding translational force requirements.

In some embodiments, another FEP section 412 can be included between the liner 410 and the metal layer 404. The FEP section 412 can be located on distal metal coil 108, as well as the tube 110 transitioning between the distal metal coil 108 and the proximal metal coil 107. In some embodiments, the FEP section 412 may continue partially or fully into the proximal metal coil 107.

In some embodiments, an FEP section 412 can be included in the proximalmost portion of the proximal metal coil 107. This FEP section 412 be approximately 0.5 inches in length. In some embodiments, there is a longitudinal gap between the proximalmost FEP section 412 and the FEP section 412 that extends over the distal metal coil 108. In some embodiments, the previously mentioned FEP sections 412 are continuous.

As shown in FIG. 15, the metal layer 404 may stop proximal to the edges of the outer polymer layer 402, liner 410, and FEP section 412. If so, a thicker portion of an adhesive layer 409 can be applied at the distal end of the metal layer 404 to match the distal end of the other layers. However, this section can be removed during manufacture, so the distal end of the metal layer 404 is the distal end of the capsule 106, which can then be covered by the liner 410. In some embodiments, the extended sections distal to the metal layer 404 are not used.

Handle

Figure 16:
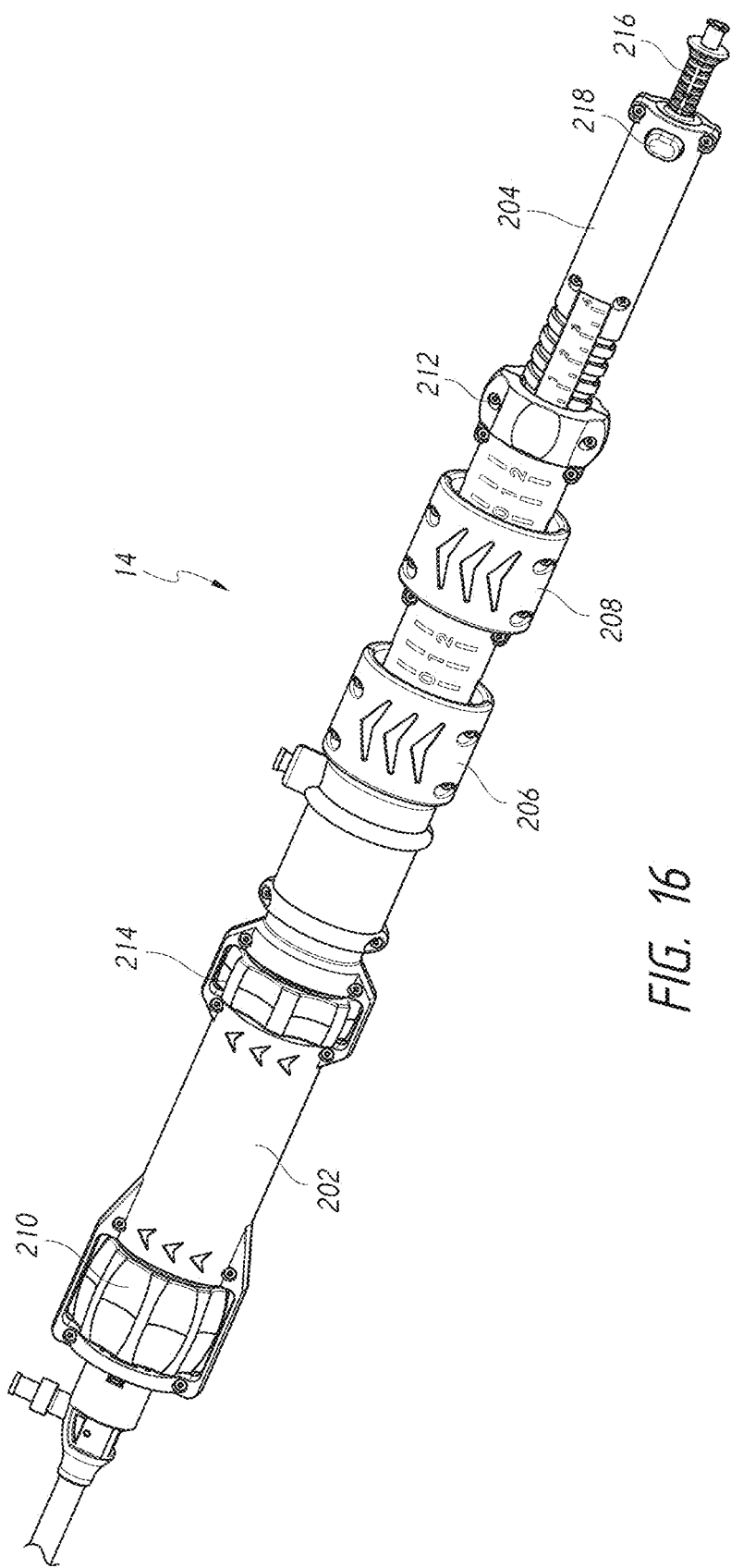
FIG. 16 illustrates an embodiment of a delivery system handle.
Figure 17:
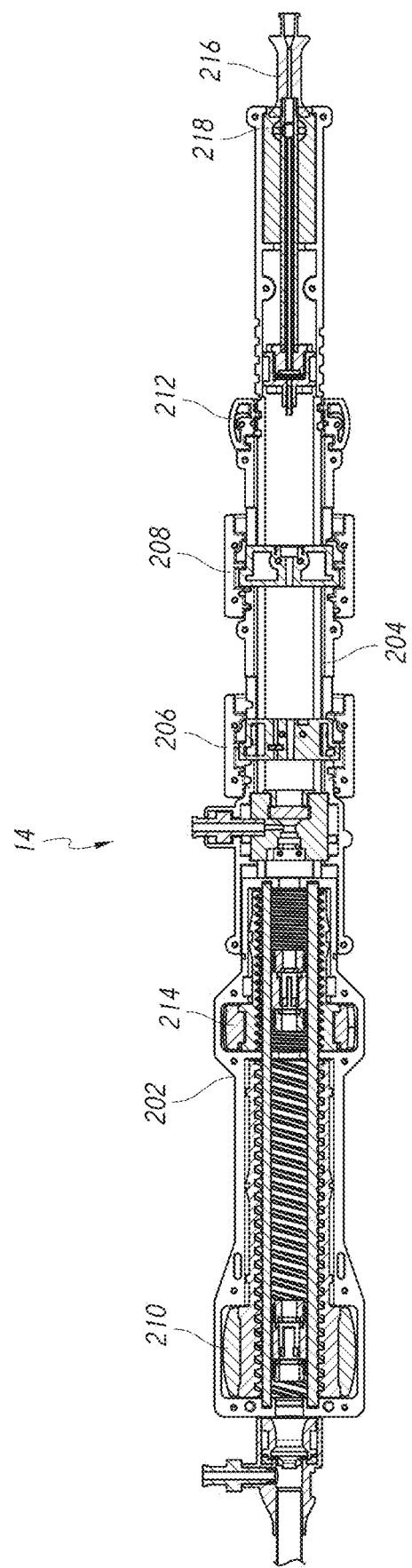
FIG. 17 illustrates a cross-section of the delivery system handle of FIG. 16.

The handle 14 is located at the proximal end of the delivery system 10 and is shown in FIG. 16. A cross-section of the handle 14 is shown in FIG. 17. The handle 14 can include a number of actuators, such as rotatable knobs, that can manipulate different components of the delivery system 10. The operation of the handle 10 is described with reference to delivery of a replacement mitral valve prosthesis 70, though the handle 10 and delivery system 10 can be used to deliver other devices as well.

The handle 14 is generally composed of two housings, a rail housing 202 and a delivery housing 204, the rail housing 202 being circumferentially disposed around the delivery housing 204. The inner surface of the rail housing 202 can include a screwable section configured to mate with an outer surface of the delivery housing 204. Thus, the delivery housing 204 is configured to slide (e.g., screw) within the rail housing 202, as detailed below. The rail housing 202 generally surrounds about one half the length of the delivery housing 204, and thus the delivery housing 204 extends both proximally and distally outside of the rail housing 202.

The rail housing 202 can contain two rotatable knobs, a distal pull wire knob 206 and a proximal pull wire knob 208. However, the number of rotatable knobs on the rail housing 202 can vary depending on the number of pull wires used. Rotation of the distal pull wire knob 206 can provide a proximal force, thereby providing axial tension on the distal pull wires 138 and causing the distal slotted section 135 of the rail hypotube 136 to bend. The distal pull wire knob 206 can be rotated in either direction, allowing for bending in either direction, which can control anterior-posterior angles. Rotation of the proximal pull wire knob 208 can provide a proximal force, and thus axial tension, on the proximal pull wires 140, thereby causing the proximal slotted section 133 of the rail hypotube 136 to bend, which can control the medial-lateral angle. The proximal pull wire knob 108 can be rotated in either direction, allowing for bending in either direction. Thus, when both knobs are actuated, there can be two bends in the rail hypotube 136, thereby allowing for three-dimensional steering of the rail shaft 132, and thus the distal end of the delivery system 10. Further, the proximal end of the rail shaft 132 is connected on an internal surface of the rail housing 202.

The bending of the rail shaft 132 can be used to position the system, in particular the distal end, at the desired patient location, such as at the native mitral valve. In some embodiments, rotation of the pull wire knobs 206/208 can help steer the distal end of the delivery system 10 through the septum and left atrium and into the left ventricle so that the prosthesis 70 is located at the native mitral valve.

Moving to the delivery housing 204, the proximal ends of the inner shaft assembly 19, outer sheath assembly 22, mid shaft assembly 21, and nose cone shaft assembly 30 can be connected to an inner surface of the delivery housing 204 of the handle 14. Thus, they can move axially relative to the rail assembly 20 and rail housing 202.

A rotatable outer sheath knob 210 can be located on the distal end of the delivery housing 204, being distal to the rail housing 202. Rotation of the outer sheath knob 210 will pull the outer sheath assembly 22 in an axial direction proximally, thus pulling the capsule 106 away from the implant 70 and releasing the distal end 301 of implant 70. Thus the outer sheath assembly 22 is individually translated with respect to the other shafts in the delivery system 10. The distal end 303 of the implant 70 can be released first, while the proximal end 301 of the implant 70 can remain radially compressed between the inner retention member 40 and the outer retention member 42.

A rotatable mid shaft knob 214 can be located on the delivery housing 204, in some embodiments proximal to the rotatable outer sheath knob 210, being distal to the rail housing 202. Rotation of the mid shaft knob 212 will pull the mid shaft assembly 21 in an axial direction proximally, thus pulling the outer retention ring 42 away from the implant 70 and uncovering the inner retention member 40 and the proximal end 301 of the implant 70, thereby releasing the implant 70. Thus, the mid shaft assembly 21 is individually translated with respect to the other shafts in the delivery system 10.

Located on the proximal end of the delivery housing 204, and thus proximal to the rail housing 202, can be a rotatable depth knob 212. As the depth knob 212 is rotated, the entirety of the delivery housing 204 moves distally or proximally with respect to the rail housing 202 which will remain in the same location. Thus, at the distal end of the delivery system 10, the inner shaft assembly 18, outer sheath assembly 22, mid shaft assembly 21, and nose cone shaft assembly 31 together (e.g., simultaneously) move proximally or distally with respect to the rail assembly 20 while the implant 70 remains in the compressed configuration. In some embodiments, actuation of the depth knob 212 can sequentially move the inner shaft assembly 18, outer sheath assembly 22, mid shaft assembly 21, and nose cone shaft assembly 31 relative to the rail assembly 20. In some embodiments, actuation of the depth knob 212 can together move the inner shaft assembly 18, outer sheath assembly 22, and mid shaft assembly 21 relative to the rail assembly 20. Accordingly, the rail shaft 132 can be aligned at a particular direction, and the other assemblies can move distally or proximally with respect to the rail shaft 132 for final positioning while not releasing the implant 70. The components can be advanced approximately 1, 2, 3, 5, 6, 7, 8, 9, or 10 cm along the rail shaft 132. The components can be advanced more than approximately 1, 2, 3, 5, 6, 7, 8, 9, or 10 cm along the rail shaft 132. An example of this is shown in FIG. 2C. The capsule 106 and outer retention ring 42 can then be individually withdrawn with respect to the inner assembly 18 as discussed above, in some embodiments sequentially, releasing the implant 70. The assemblies other than the rail assembly 20 can then be withdrawn back over the rail shaft 132 by rotating the depth knob 212 in the opposite direction.

The handle 14 can further include a mechanism (knob, button, handle) 216 for moving the nose cone shaft 27, and thus the nose cone 28. For example, a knob 216 can be a portion of the nose cone assembly 31 that extends from a proximal end of the handle 14. Thus, a user can pull or push on the knob 216 to translate the nose cone shaft 27 distally or proximally individually with respect to the other shafts. This can be advantageous for proximally translating the nose cone 28 into the outer sheath assembly 22/capsule 106, thus facilitating withdraw of the delivery system 10 from the patient.

In some embodiments, the handle 14 can provide a lock 218, such as a spring lock, for preventing translation of the nose cone shaft 27 by the knob 216 discussed above. In some embodiments, the lock 218 can be always active, and thus the nose cone shaft 27 will not move without a user disengaging the lock 218. The lock can be, for example, a spring lock that is always engaged until a button 218 on the handle 14 is pressed, thereby releasing the spring lock and allowing the nose cone shaft 27 to translate proximally/distally. In some embodiments, the spring lock 218 allows one-way motion, either proximal or distal motion, of the nose cone shaft 27 but prevents motion in the opposite direction.

The handle 14 can further include a communicative flush port for flushing out different lumens of the delivery system 10. In some embodiments, a single flush port on the handle 14 can provide fluid connection to multiple assemblies. In some embodiments, the flush port can provide fluid connection to the outer sheath assembly 22. In some embodiments, the flush port can provide fluid connection to the outer sheath assembly 22 and the mid shaft assembly 21. In some embodiments, the flush port can provide fluid connection to the outer sheath assembly 22, the mid shaft assembly 21, and the rail assembly 20. In some embodiments, the flush port can provide fluid connection to the outer sheath assembly 22, the mid shaft assembly 21, the rail assembly 20, and the inner assembly 18. Thus, in some embodiments, the rail shaft 132, the outer retention ring 42, and the capsule 406 can all be flushed by a single flush port.

Valve Delivery Positioning

Methods of using the delivery system 10 in connection with a replacement mitral valve will now be described. In particular, the delivery system 10 can be used in a method for percutaneous delivery of a replacement mitral valve to treat patients with moderate to severe mitral regurgitation. The below methods are merely examples of the how the delivery system may be used. It will be understood that the delivery systems described herein can be used as part of other methods as well.

Figure 18:
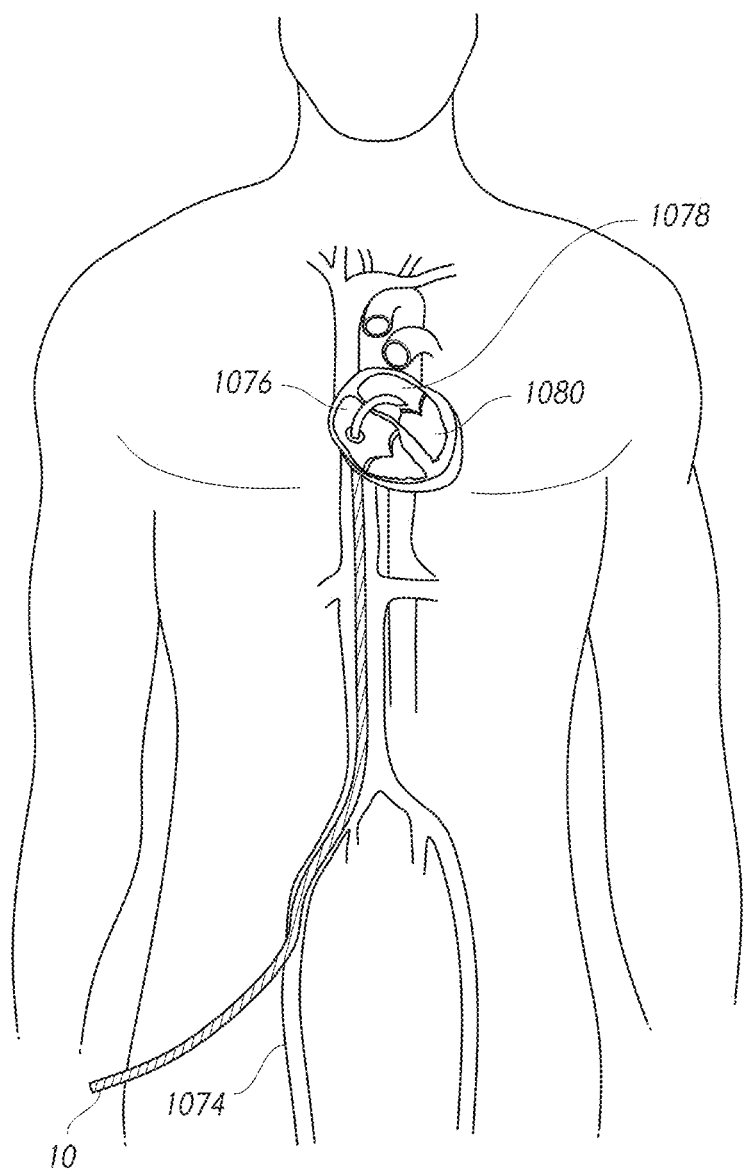
FIG. 18 illustrates a schematic representation of a transseptal delivery approach.

As shown in FIG. 18, in one embodiment the delivery system 10 can be placed in the ipsilateral femoral vein 1074 and advanced toward the right atrium 1076. A transseptal puncture using known techniques can then be performed to obtain access to the left atrium 1078. The delivery system 10 can then be advanced in to the left atrium 1078 and then to the left ventricle 1080. FIG. 18 shows the delivery system 10 extending from the ipsilateral femoral vein 1074 to the left atrium 1078. In embodiments of the disclosure, a guide wire is not necessary to position the delivery system 10 in the proper position, although in other embodiments, one or more guide wires may be used.

Accordingly, it can be advantageous for a user to be able to steer the delivery system 10 through the complex areas of the heart in order to position a replacement mitral valve in line with the native mitral valve. This task can be performed with or without the use of a guide wire with the above disclosed system. The distal end of the delivery system can be advanced into the left atrium 1078. A user can then manipulate the rail assembly 20 to target the distal end of the delivery system 10 to the appropriate area. A user can then continue to pass the bent delivery system 10 through the transseptal puncture and into the left atrium 1078. A user can then further manipulate the delivery system 10 to create an even greater bend in the rail assembly 20. Further, a user can torque the entire delivery system 10 to further manipulate and control the position of the delivery system 10. In the fully bent configuration, a user can then place the replacement mitral valve in the proper location. This can advantageously allow delivery of a replacement valve to an in-situ implantation site, such as a native mitral valve, via a wider variety of approaches, such as a transseptal approach.

The rail assembly 20 can be particularly advantageous for entering into the native mitral valve. As discussed above, the rail assembly 20 can form two bends, both of which can be located in the left atrium 1078. The bends in the rail assembly 20 can position the prosthesis 70, located in the implant retention area 16, so that it is coaxial with the native mitral valve. Once the prosthesis 70 is coaxial, the outer sheath assembly 22, mid shaft assembly 21, inner assembly 18, and nose cone assembly 31 can together be advanced (e.g., using the depth knob 212 of the handle 14) distally relative to the rail assembly 20. These assemblies advance straight off of the rail assembly 20, thus advancing them coaxial with the native mitral valve until the prosthesis 70 is to be released while maintain the prosthesis 70 in the compressed configuration, as discussed below. Thus, the rail assembly 20 provides the ability for a user to lock the angular position in place, so that the user then has to just longitudinally advance the other assemblies over the rail assembly 20 while not needed to make any angular changes, greatly simplifying the procedure. The rail assembly 20 acts as an independent steering assembly, where all the assembly does is provide steerability and no further prosthesis release functionality. Further, the construction of the rail assembly 20 as described above is sufficiently rigid so that when the rail assembly is actuated to its bent shape, movement of the other components, e.g., the outer sheath assembly 22, mid shaft assembly 21, inner assembly 18, and/or nose cone assembly 31, the rail assembly 20 maintains its shape. Thus, the rail assembly 20 can remain in the desired bent position during the sliding of the other assemblies relative to the rail assembly 20, and the rail assembly 20 can help direct the other assemblies to the final position. The proximal/distal translation of the other assemblies over the rail assembly 20 allows for ventricular-atrial motion. In addition, once the distal anchors 80 of the prosthesis 70 have been released in the left ventricle 1080, but prior to full release, the other assemblies can be proximally retracted over the rail assembly 20 to capture any leaflets or chordae.

Figure 19:
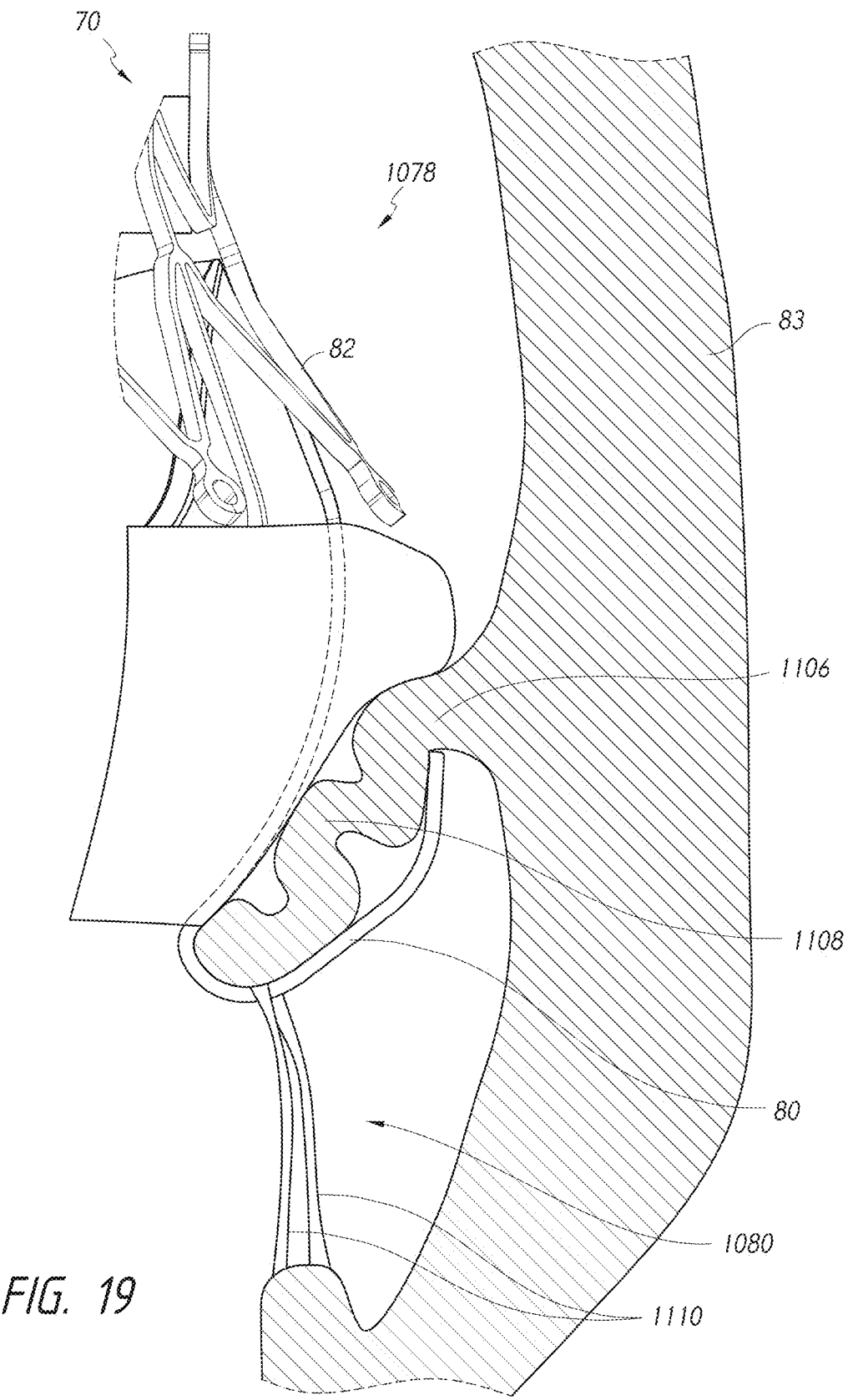
FIG. 19 illustrates a schematic representation of a valve prosthesis positioned within a native mitral valve.

Reference is now made to FIG. 19 which illustrates a schematic representation of a portion of an embodiment of a replacement heart valve (prosthesis 70) positioned within a native mitral valve of a heart 83. Further details regarding how the prosthesis 70 may be positioned at the native mitral valve are described in U.S. Publication No. 2015/0328000A1, the entirety of which is hereby incorporated by reference, including but not limited to FIGS. 13A-15 and paragraphs [0036]-[0045]. A portion of the native mitral valve is shown schematically and represents typical anatomy, including a left atrium 1078 positioned above an annulus 1106 and a left ventricle 1080 positioned below the annulus 1106. The left atrium 1078 and left ventricle 1080 communicate with one another through a mitral annulus 1106. Also shown schematically in FIG. 19 is a native mitral leaflet 1108 having chordae tendineae 1110 that connect a downstream end of the mitral leaflet 1108 to the papillary muscle of the left ventricle 1080. The portion of the prosthesis 70 disposed upstream of the annulus 1106 (toward the left atrium 1078) can be referred to as being positioned supra-annularly. The portion generally within the annulus 1106 is referred to as positioned intra-annularly. The portion downstream of the annulus 1106 is referred to as being positioned sub-annularly (toward the left ventricle 1080).

As shown in FIG. 19, the replacement heart valve (e.g., prosthesis 70) can be positioned so that the mitral annulus 1106 is located the distal anchors 80 and the proximal anchors 82. In some situations, the prosthesis 70 can be positioned such that ends or tips of the distal anchors 80 contact the annulus 1106 as shown, for example, in FIG. 19. In some situations, the prosthesis 70 can be positioned such that ends or tips of the distal anchors 80 do not contact the annulus 1106. In some situations, the prosthesis 70 can be positioned such that the distal anchors 80 do not extend around the leaflet 1108.

As illustrated in FIG. 19, the replacement heart valve 70 can be positioned so that the ends or tips of the distal anchors 80 are on a ventricular side of the mitral annulus 1106 and the ends or tips of the proximal anchors 82 are on an atrial side of the mitral annulus 1106. The distal anchors 80 can be positioned such that the ends or tips of the distal anchors 80 are on a ventricular side of the native leaflets beyond a location where chordae tendineae 1110 connect to free ends of the native leaflets. The distal anchors 80 may extend between at least some of the chordae tendineae 1110 and, in some situations such as those shown in FIG. 19, can contact or engage a ventricular side of the annulus 1106. It is also contemplated that in some situations, the distal anchors 80 may not contact the annulus 1106, though the distal anchors 80 may still contact the native leaflet 1108. In some situations, the distal anchors 80 can contact tissue of the left ventricle 104 beyond the annulus 1106 and/or a ventricular side of the leaflets.

During delivery, the distal anchors 80 (along with the frame) can be moved toward the ventricular side of the annulus 1106, such as by translating the other assemblies (e.g., outer sheath assembly 22, mid shaft assembly 21, inner assembly 18, and nose cone assembly 31) proximally with respect to the rail assembly 20, with the distal anchors 80 extending between at least some of the chordae tendineae 1110 to provide tension on the chordae tendineae 1110. The degree of tension provided on the chordae tendineae 1110 can differ. For example, little to no tension may be present in the chordae tendineae 1110 where the leaflet 1108 is shorter than or similar in size to the distal anchors 80. A greater degree of tension may be present in the chordae tendineae 1110 where the leaflet 1108 is longer than the distal anchors 80 and, as such, takes on a compacted form and is pulled proximally. An even greater degree of tension may be present in the chordae tendineae 1110 where the leaflets 1108 are even longer relative to the distal anchors 80. The leaflet 1108 can be sufficiently long such that the distal anchors 80 do not contact the annulus 1106.

Figure 20:
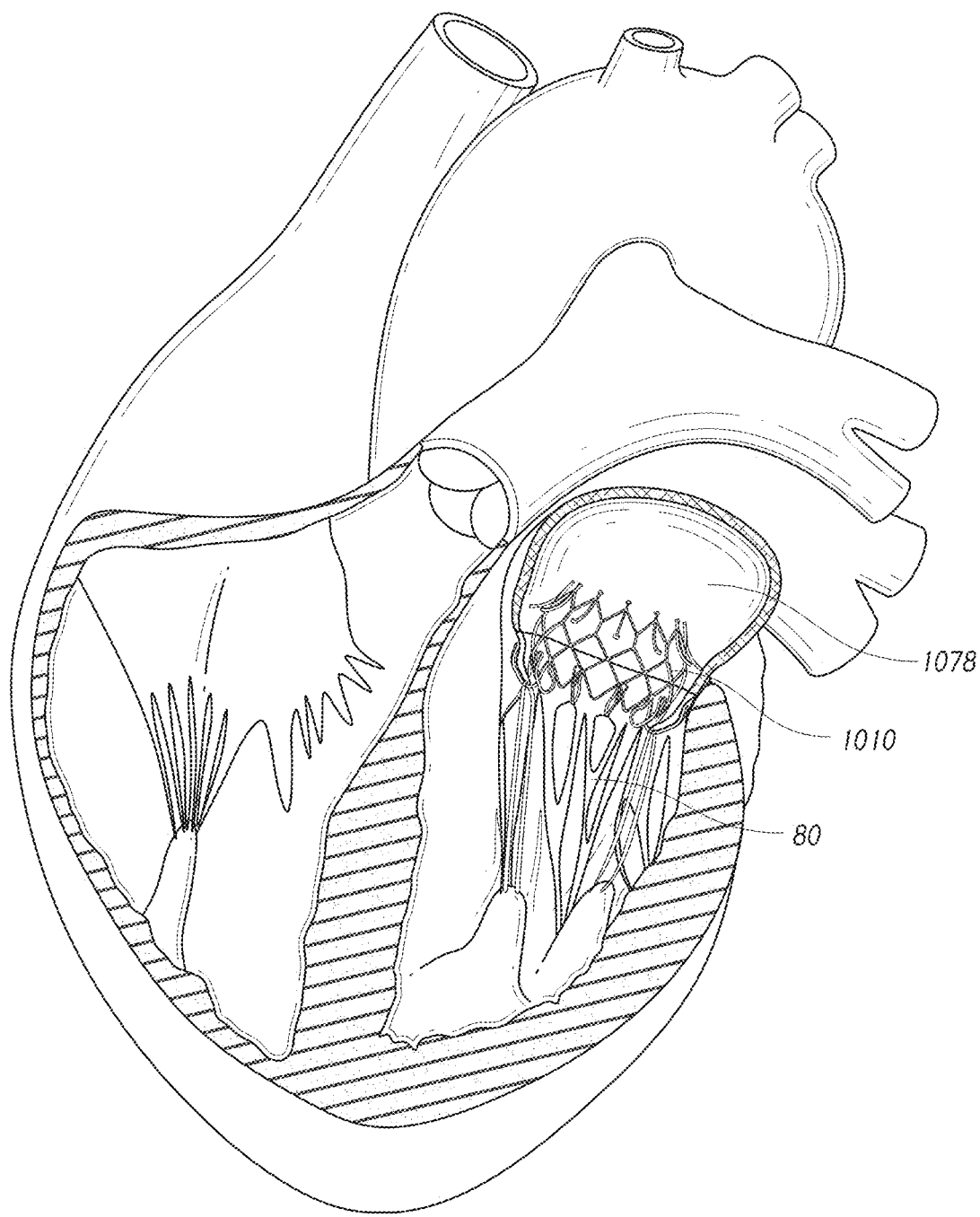
FIG. 20 shows the valve prosthesis frame located within a heart.

The proximal anchors 82, if present, can be positioned such that the ends or tips of the proximal anchors 82 are adjacent the atrial side of the annulus 1106 and/or tissue of the left atrium 1078 beyond the annulus 1106. In some situations, some or all of the proximal anchors 82 may only occasionally contact or engage atrial side of the annulus 1106 and/or tissue of the left atrium 1078 beyond the annulus 1106. For example, as illustrate in FIG. 19, the proximal anchors 82 may be spaced from the atrial side of the annulus 1106 and/or tissue of the left atrium 1078 beyond the annulus 1106. The proximal anchors 82 could provide axial stability for the prosthesis 70. It is also contemplated that some or all of the proximal anchors 82 may contact the atrial side of the annulus 1106 and/or tissue of the left atrium 1078 beyond the annulus 1106. FIG. 20 illustrates the prosthesis 70 implanted in the heart. Although the illustrated replacement heart valve includes both proximal and distal anchors, it will be appreciated that proximal and distal anchors are not required in all cases. For example, a replacement heart valve with only distal anchors may be capable of securely maintaining the replacement heart valve in the annulus. This is because the largest forces on the replacement heart valve are directed toward the left atrium during systole. As such, the distal anchors are most important for anchoring the replacement heart valve in the annulus and preventing migration.

Delivery Method

Figure 21:
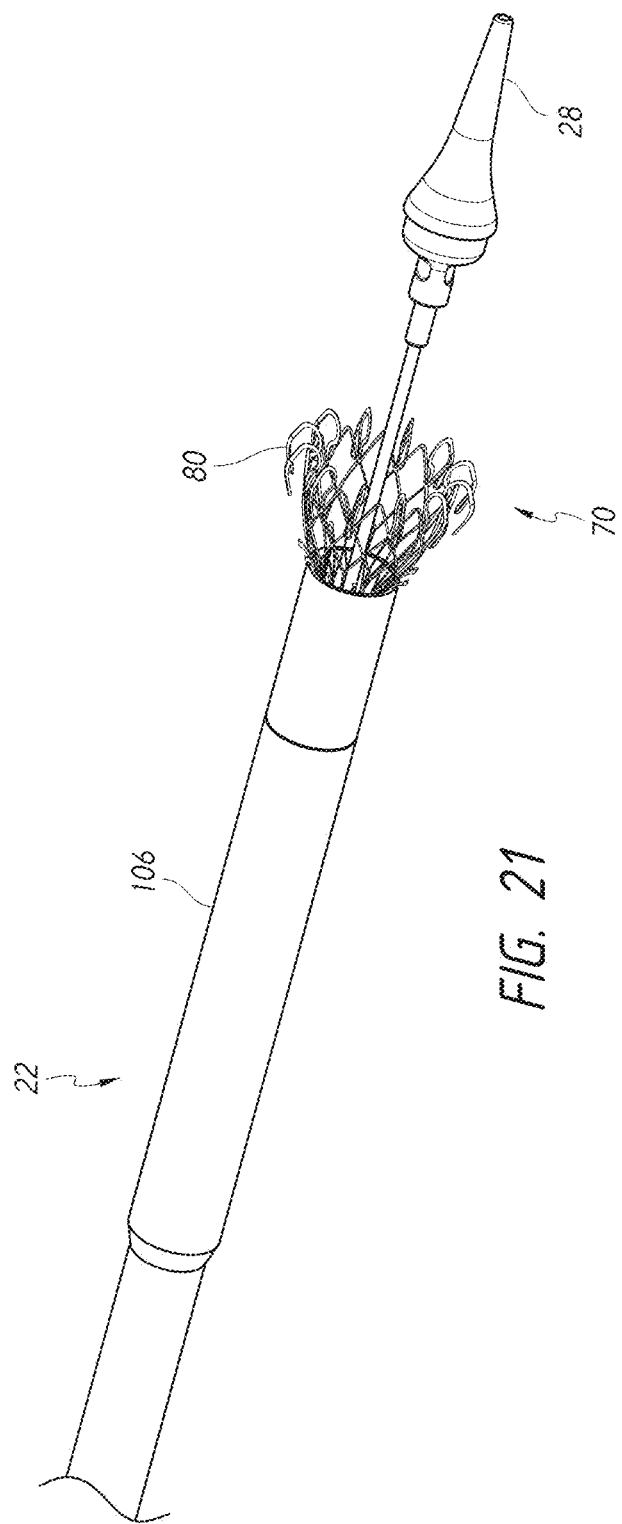
FIGS. 21-23 show steps of a method for delivery of the valve prosthesis to an anatomical location.
Figure 22:
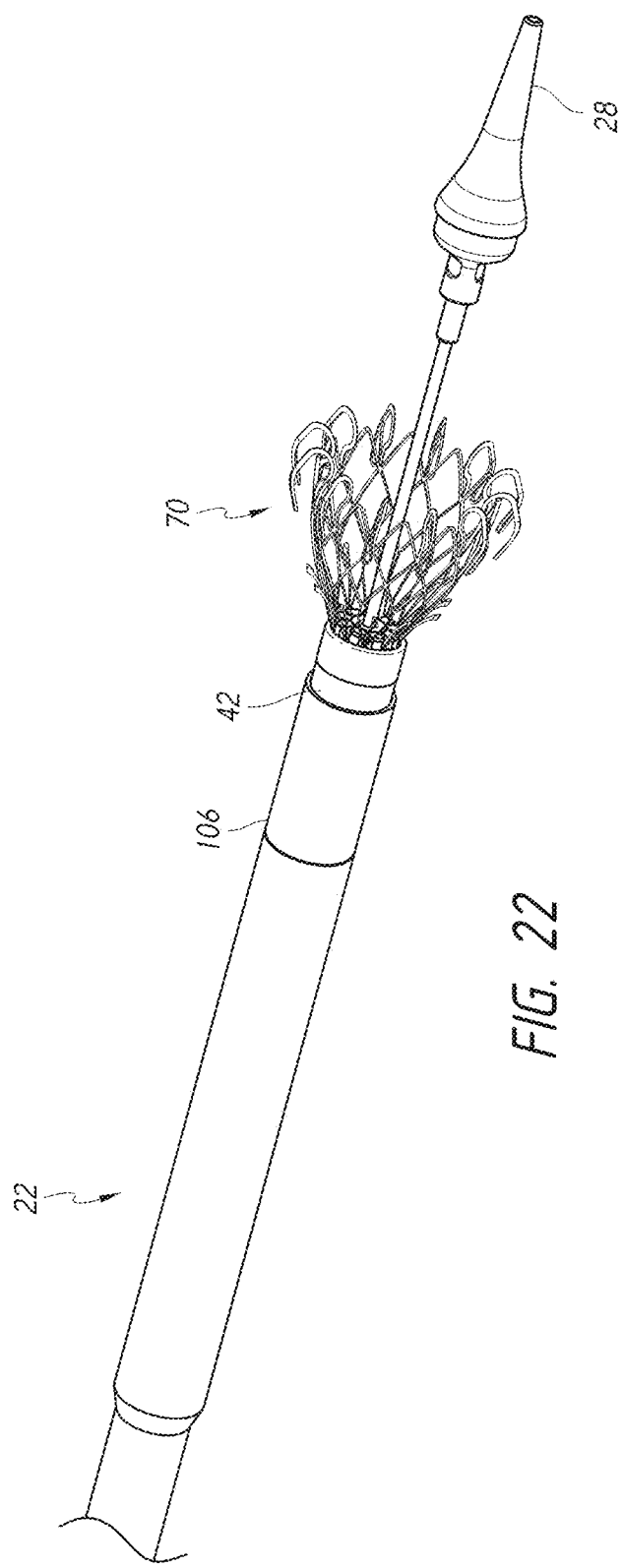
Figure 23:
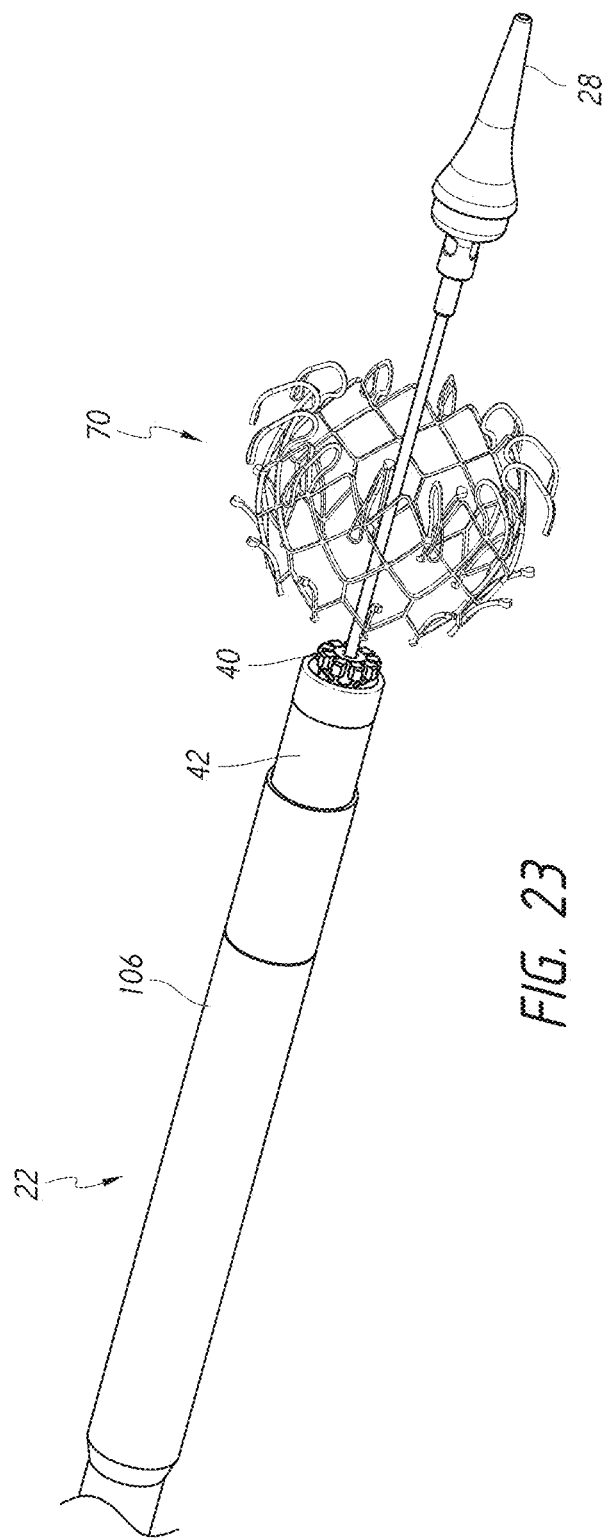

FIGS. 21-23 illustrate the release mechanism of the delivery system 10. During the initial insertion of the prosthesis 70 and the delivery system 10 into the body, the prosthesis 70 can be located within the system 10, similar to as shown in FIG. 2A. The distal end 303 of the prosthesis 70, and specifically the distal anchors 80, are restrained within the capsule 106 of the outer sheath assembly 22, thus preventing expansion of the prosthesis 70. Similar to what is shown in FIG. 2A, the distal anchors 80 can extend distally when positioned in the capsule. The proximal end 301 of the prosthesis 70 is restrained within the capsule 106 and within a portion of the inner retention member 40 and thus is generally constrained between the capsule 106 and the inner retention member 40.

The system 10 can first be positioned to a particular location in a patient's body, such as at the native mitral valve, through the use of the steering mechanisms discussed herein or other techniques.

Once the prosthesis 70 is loaded into the delivery system 10, a user can thread a guide wire into a patient to the desired location. The guide wire passes through the lumen of the nose cone assembly 31, and thus the delivery system 10 can be generally advanced through the patient's body following the guide wire. The delivery system 10 can be advanced by the user manually moving the handle 14 in an axial direction. In some embodiments, the delivery system 10 can be placed into a stand while operating the handle 14 controls.

Once generally in heart, the user can begin the steering operation of the rail assembly 20 using the distal pull wire knob 206 and/or the proximal pull wire knob 208. By turning either of the knobs, the user can provide flexing/bending of the rail assembly 20 (either on the distal end or the proximal end), thus bending the distal end of the delivery system 10 in one, two, or more locations into the desired configuration. As discussed above, the user can provide multiple bends in the rail assembly 20 to direct the delivery system 10 towards the mitral valve. In particular, the bends of the rail assembly 20 can direct a distal end of the delivery system 10, and thus the capsule 106, along the center axis passing through the native mitral valve. Thus, when the outer sheath assembly 22, mid shaft assembly 21, inner assembly 18, and nose cone assembly 31 are together advanced over the rail assembly 20 with the compressed prosthesis 70, the capsule 106 proceed directly in line with the axis for proper release of the prosthesis 70.

The user can also rotate and/or move the handle 14 itself in a stand for further fine tuning of the distal end of the delivery system 10. The user can continually turn the proximal and/or distal pull wire knobs 208/206, as well as moving the handle 14 itself, to orient the delivery system 10 for release of the prosthesis 70 in the body. The user can also further move the other assemblies relative to the rail assembly 20, such as proximally or distally.

In a next step, the user can rotate the depth knob 212. As discussed, rotation of this knob 212 together advances the inner shaft assembly 18, mid shaft assembly 21, outer sheath assembly 22, and nose cone assembly 31 over/through the rail assembly 20 while the prosthesis 70 remains in the compressed configuration within the implant retention area 16. Due to the rigidity of, for example, either the inner shaft assembly 18, the mid shaft assembly 21, and/or the outer sheath assembly 22, these assemblies proceed straight forward in the direction aligned by the rail assembly 20.

Once in the release position, the user can rotate the outer sheath knob 210, which individually translates the outer sheath assembly 22 (and thus the capsule 106) with respect to the other assemblies, in particular the inner assembly 18, in a proximal direction towards the handle 14 as shown in FIG. 21. By doing so, the distal end 303 of prosthesis 70 is uncovered in the body, allowing for the beginning of expansion. At this point, the distal anchors 80 can flip proximally and the distal end 303 begins to expand radially outwardly. For example, if the system 10 has been delivered to a native mitral valve location through a transseptal approach, the nose cone is positioned in the left ventricle, preferably aligning the prosthesis 70 such that it is generally perpendicular to the plane of the mitral annulus. The distal anchors 80 expand radially outwardly within the left ventricle. The distal anchors 80 can be located above the papillary heads, but below the mitral annulus and mitral leaflets. In some embodiments, the distal anchors 80 may contact and/or extend between the chordae in the left ventricle, as well as contact the leaflets, as they expand radially. In some embodiments, the distal anchors 80 may not contact and/or extend between the chordae or contact the leaflets. Depending on the position of the prosthesis 70, the distal ends of the distal anchors 80 may be at or below where the chordae connect to the free edge of the native leaflets.

As shown in the illustrated embodiment, the distal end 303 of the prosthesis 70 is expanded outwardly. It should be noted that the proximal end 301 of the prosthesis 70 can remain covered by the outer retention ring during this step such that the proximal end 301 remains in a radially compacted state. At this time, the system 10 may be withdrawn proximally so that the distal anchors 80 capture and engage the leaflets of the mitral valve, or may be moved proximally to reposition the prosthesis 70. For example, the assemblies may be proximally moved relative to the rail assembly 20. Further, the system 10 may be torqued, which may cause the distal anchors 80 to put tension on the chordae through which at least some of the distal anchors may extend between. However, in some embodiments the distal anchors 80 may not put tension on the chordae. In some embodiments, the distal anchors 80 may capture the native leaflet and be between the chordae without any further movement of the system 10 after withdrawing the outer sheath assembly 22.

During this step, the system 10 may be moved proximally or distally to cause the distal or ventricular anchors 80 to properly capture the native mitral valve leaflets. This can be done by moving the outer sheath assembly 22, mid shaft assembly 21, inner assembly 18, and nose cone assembly 31 with respect to the rail assembly 20. In particular, the tips of the ventricular anchors 80 may be moved proximally to engage a ventricular side of the native annulus, so that the native leaflets are positioned between the anchors 80 and the body of the prosthesis 70. When the prosthesis 70 is in its final position, there may or may not be tension on the chordae, though the distal anchors 80 can be located between at least some of the chordae.

The proximal end 301 of the prosthesis 70 will remain in the outer retention ring 42 after retraction of the capsule 106. As shown in FIG. 22, once the distal end 303 of the prosthesis 70 is fully expanded (or as fully expanded as possible at this point), the outer retention ring 42 can be individually withdrawn proximally with respect to the other assemblies, in particular relative to the inner assembly 18, to expose the inner retention member 40, thus beginning the expansion of the proximal end 301 of the prosthesis 70. For example, in a mitral valve replacement procedure, after the distal or ventricular anchors 80 are positioned between at least some of the chordae tendineae and/or engage the native mitral valve annulus, the proximal end 301 of the prosthesis 70 may be expanded within the left atrium.

The outer retention ring 42 can be moved proximally such that the proximal end 310 of the prosthesis 70 can radially expand to its fully expanded configuration as shown in FIG. 23. After expansion and release of the prosthesis 70, the inner assembly 18, nose cone assembly 31, mid shaft assembly 21, and outer sheath assembly 22 can be simultaneously withdrawn proximally along or relative to the rail assembly 20 back to their original position. In some embodiments, they are not withdrawn relative to the rail assembly 20 and remain in the extended position. Further, the nose cone 28 can be withdrawn through the center of the expanded prosthesis 70 and into the outer sheath assembly 22, such as by proximally translating the knob 216. The system 10 can then be removed from the patient.

Figure 24A:
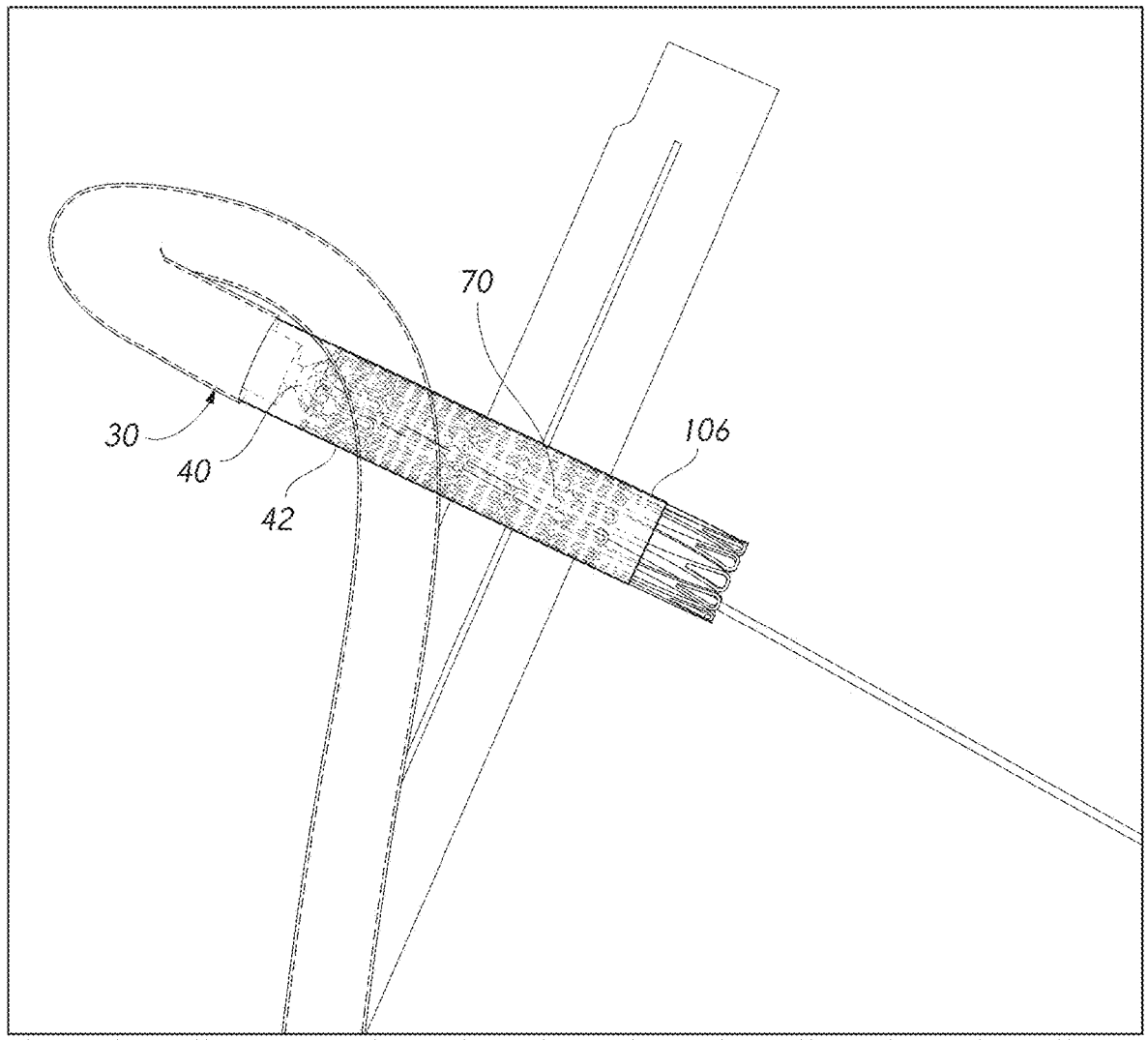
FIGS. 24A-B illustrate the methodology of the rail delivery system.
Figure 24B:
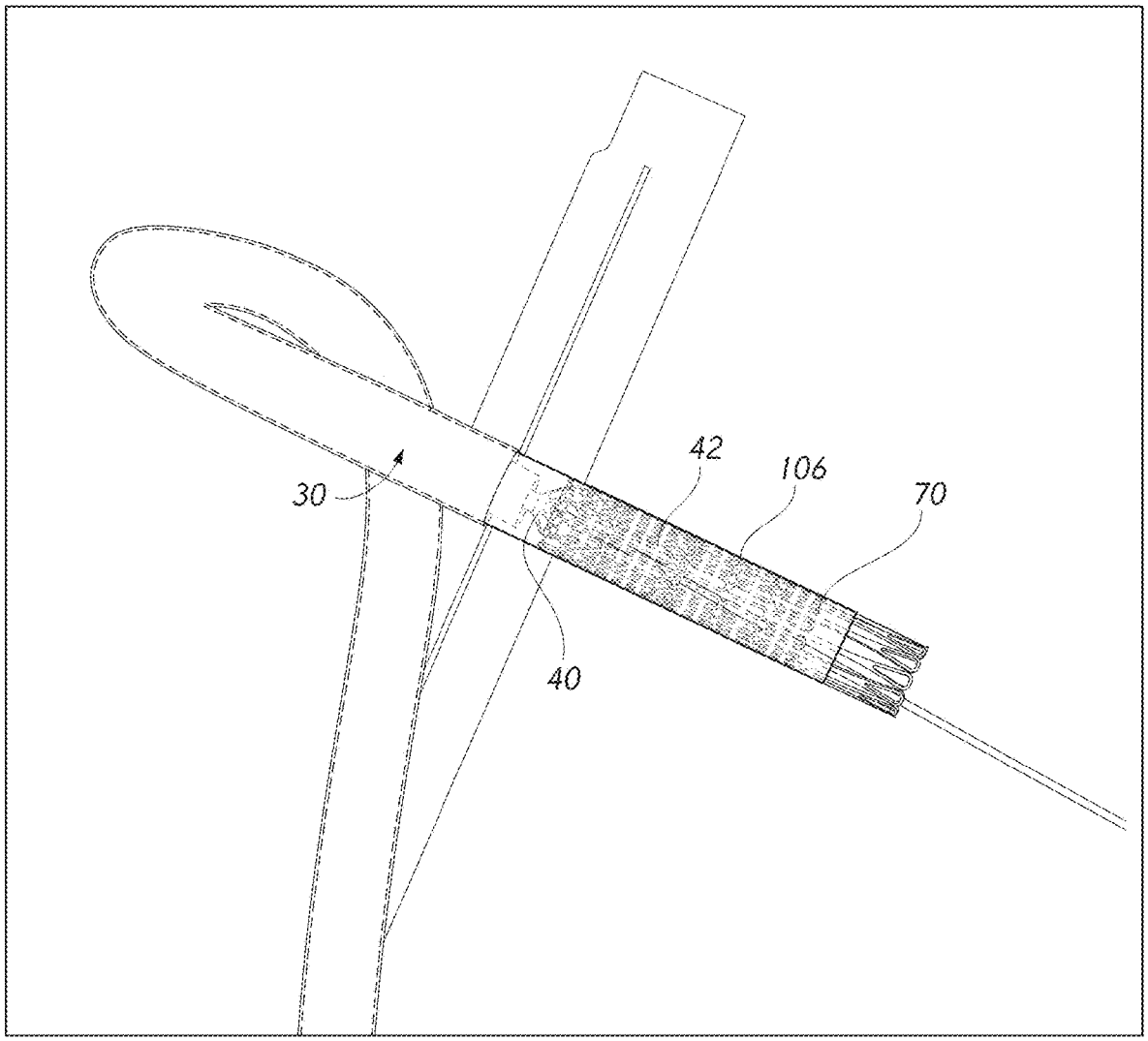

FIGS. 24A-B illustrate the advancement of the different assemblies over the rail assembly 20. FIG. 24A illustrates the assemblies in their proximalmost position over the rail assembly 20. FIG. 24B illustrates the assemblies in their distalmost position as compared to the rail assembly 20, such as shown in FIG. 2C. Thus, the assemblies snake along the rail assembly 20 and extend distally away.

In some embodiments, the prosthesis 70 can be delivered under fluoroscopy so that a user can view certain reference points for proper positioning of the prosthesis 70. Further, echocardiography can be used for proper positioning of the prosthesis 70.

Following is a discussion of an alternative implantation method for delivering a replacement mitral valve to a mitral valve location. Elements of the below can be incorporated into the above discussion and vice versa. Prior to insertion of the delivery system 10, the access site into the patient can be dilated. Further, a dilator can be flushed with, for example, heparinized saline prior to use. The delivery system 10 can then be inserted over a guide wire. In some embodiments, any flush ports on the delivery system 10 can be pointed vertically. Further, if an introducer tube is used, integrated or otherwise, this can be stabilized. The delivery system 10 can be advanced through the septum until a distal end of the delivery system 10 is positioned across the septum into the left atrium 1078. Thus, the distal end of the delivery system 10 can be located in the left atrium 1078. In some embodiments, the delivery system 10 can be rotated, such as under fluoroscopy, into a desired position. The rail can be flex so that direct a distal end of the delivery system 10 towards the septum and mitral valve. The position of the delivery system 10, and the prosthesis 70 inside, can be verified using echocardiography and fluoroscopic guidance.

In some embodiments, the prosthesis 70 can be located, prior to release, above the mitral annulus 1106, in line with the mitral annulus 1106, or below the mitral annulus 1106. In some embodiments, the prosthesis 70 can be located, prior to expansion, fully above the mitral annulus 1106, in line with the mitral annulus 1106, just below the mitral annulus 1106, or fully below the mitral annulus 1106. In some embodiments, the prosthesis 70 can be located, prior to expansion, partially above the mitral annulus 1106, in line with the mitral annulus 1106, or partially below the mitral annulus 1106. In some embodiments, a pigtail catheter can be introduced into the heart to perform a ventriculogram for proper viewing.

In some embodiments, the position of the mitral plane and the height of any papillary muscles on the fluoroscopy monitor can be marked to indicate an example target landing zone. If needed, the delivery system 10 can be unflexed, reduced in rotation, and retracted to reduce tension on the delivery system 10 as well as reduce contact with the left ventricular wall, the left atrial wall, and/or the mitral annulus 1106.

Further, the delivery system 10 can be positioned to be coaxial to the mitral annulus 1106, or at least as much as possible, while still reducing contact with the left ventricular wall, the left atrial wall, and/or the mitral annulus 1106 and reducing delivery system tension. An echo probe can be positioned to view the anterior mitral leaflet (AML), the posterior mitral leaflet (PML) (leaflets 1108), mitral annulus 1106, and outflow tract. Using fluoroscopy and echo imaging, the prosthesis 1010 can be confirmed to be positioned at a particular depth and coaxiality with the mitral annulus 1106.

Afterwards, the outer sheath assembly 22 can be retracted to expose the ventricular anchors 80, thereby releasing them.

In some embodiments, once exposed, the outer sheath assembly 22 can be reversed in direction to relieve tension on the outer sheath assembly 22. In some embodiments, reversing the direction could also serve to partially or fully capture the prosthesis 70.

The distal anchors 80 can be released in the left atrium 1078. Further, the proximal anchors 82, if included in the prosthesis 70, are not yet exposed. Moreover, the body of the prosthesis 70 has not undergone any expansion at this point. However, in some embodiments, one or more of the distal anchors 80 can be released in either the left atrium 1078 (e.g., super-annular release) or generally aligned with the mitral valve annulus 1106 (e.g., intra-annular release), or just below the mitral valve annulus 1106 (e.g., sub-annular release). In some embodiments, all of the distal anchors 80 can be released together. In other embodiments, a subset of the distal anchors 80 can be released while at a first position and another subset of the distal anchors 80 can be released while at a second position. For example, some of the distal anchors 80 can be released in the left atrium 1078 and some of the distal anchors 80 can be released while generally aligned with the mitral valve annulus 1106 or just below the mitral valve annulus 1106.

If the distal anchors 80 are released "just below" the mitral valve annulus 1106, the may be released at 1 inch, ¾ inch, ½ inch, ¼ inch, ⅛ inch, ¹⁄₁₀ inch or ¹⁄₂₀ inch below the mitral valve annulus 1106. In some embodiments, the distal anchors 80 the may be released at less than 1 inch, ¾ inch, ½ inch, ¼ inch, ⅛ inch, ¹⁄₁₀ inch or ¹⁄₂₀ inch below the mitral valve annulus 1106. This may allow the distal anchors 80 to snake through the chordae upon release. This can advantageously allow the prosthesis 70 to slightly contract when making the sharp turn down toward the mitral valve. In some embodiments, this may eliminate the need for a guide wire assisting to cross the mitral valve. In some embodiments, the guide wire may be withdrawn into the delivery system 10 before or following release of the distal anchors 80.

In some embodiments, the distal anchors 80 can be released immediately after crossing the septum, and then the final trajectory of the delivery system 10 can be determined. Thus, the delivery system 10 can cross the septum, release the ventricular anchors 80, establish a trajectory, and move into the left ventricle to capture the leaflets.

As discussed in detail above, upon release from the delivery system 10, the distal anchors 80 can flip from extending distally to extending proximally. This flip can be approximately 180°. Accordingly, in some embodiments, the distal anchors 80 can be flipped in either the left atrium 1078 (e.g., super-annular flip), generally aligned with the mitral valve annulus 1106 (e.g., intra-annular flip), or just below the mitral valve annulus 1106 (e.g., sub-annular flip). The proximal anchors 82, if any, can remain within the delivery system 10. In some embodiments, all of the distal anchors 80 can be flipped together. In other embodiments, a subset of the distal anchors 80 can be flipped while at a first position and another subset of the distal anchors 80 can be released while at a second position. For example, some of the distal anchors 80 can be flipped in the left atrium 1078 and some of the distal anchors 80 can be flipped while generally aligned with the mitral valve annulus 1106 or just below the mitral valve annulus 1106.

In some embodiments, the distal anchors 80 may be positioned in line with the annulus 1106 or just below the annulus 1106 in the non-flipped position. In some embodiments, the distal anchors 80 may be position in line with the annulus 1106 or just below the annulus 1106 in the flipped position. In some embodiments, prior to flipping the distalmost portion of the prosthesis 70 can be located within or below the mitral valve annulus 1106, such as just below the mitral valve annulus 1106. However, flipping the anchors can cause, without any other movement of the delivery system 10, the distalmost portion of the prosthesis 70/anchors 80 to move upwards, moving it into the left atrium 1078 or moving it in line with the mitral annulus 1106. Thus, in some embodiments the distal anchors 80 can begin flipping at the annulus 1106 but be fully within the left atrium 1078 upon flipping. In some embodiments the distal anchors 80 can begin flipping below the annulus 1106 but be fully within the annulus 1106 upon flipping.

In some embodiments, the distal anchors 80 can be proximal (e.g., toward the left atrium 1078) of a free edge of the mitral leaflets 1108 upon release and flipping. In some embodiments, the distal anchors 80 can be aligned with (e.g., toward the left atrium 1078) a free edge of the mitral leaflets 1108 upon release and flipping. In some embodiments, the distal anchors 80 can be proximal (e.g., toward the left atrium 1078) of a free edge of the mitral valve annulus 1106 upon release and flipping. In some embodiments, the distal anchors 80 can be aligned with (e.g., toward the left atrium 1078) a free edge of the mitral valve annulus 1106 upon release and flipping.

Thus, in some embodiments the distal anchors 80 can be released/flipped above where the chordae 1110 attach to the free edge of the native leaflets 1108. In some embodiments the distal anchors 80 can be released/flipped above where some the chordae 1110 attach to the free edge of the native leaflets 1108. In some embodiments the distal anchors 80 can be released/flipped above where all the chordae 1110 attach to the free edge of the native leaflets 1108. In some embodiments, the distal anchors 80 can be released/flipped above the mitral valve annulus 1106. In some embodiments, the distal anchors 80 can be released/flipped above the mitral valve leaflets 1108. In some embodiments, the distal anchors 80 can be released/flipped generally in line with the mitral valve annulus 1106. In some embodiments, the distal anchors 80 can be released/flipped generally in line with the mitral valve leaflets 1108. In some embodiments, the tips of the distal anchors 80 can be released/flipped generally in line with the mitral valve annulus 1106. In some embodiments, the tips of the distal anchors 80 can be released/flipped generally in line with the mitral valve leaflets 1108. In some embodiments the distal anchors 80 can be released/flipped below where some the chordae 1110 attach to the free edge of the native leaflets 1108. In some embodiments the distal anchors 80 can be released/flipped below where all the chordae 1110 attach to the free edge of the native leaflets 1108. In some embodiments, the distal anchors 80 can be released/flipped below the mitral valve annulus 1106. In some embodiments, the distal anchors 1024 can be released/flipped below the mitral valve leaflets 1108.

Once the distal anchors 80 are released and flipped, the delivery system 10 can be translated towards the left ventricle 1080 through the mitral valve annulus 1106 so that the distal anchors 80 enter the left ventricle 1080. In some embodiments, the distal anchors 80 can compress when passing through the mitral valve annulus 1106. In some embodiments, the prosthesis 70 can compress when passing through the mitral valve annulus 1106. In some embodiments, the prosthesis 70 does not compress when it passes through the mitral annulus 1106. The distal anchors 80 can be delivered anywhere in the left ventricle 1080 between the leaflets 1108 and the papillary heads.

In some embodiments, the distal anchors 80 are fully expanded prior to passing through the mitral valve annulus 1106. In some embodiments, the distal anchors 80 are partially expanded prior to passing through the mitral valve annulus 1106 and continued operation of the delivery system 10 can fully expand the distal anchors 80 in the left ventricle 1080.

When the distal anchors 80 enter the left ventricle 1080, the distal anchors 80 can pass through the chordae 1110 and move behind the mitral valve leaflets 1108, thereby capturing the leaflets 1108. In some embodiments, the distal anchors 80 and/or other parts of the prosthesis 1010 can push the chordae 1110 and/or the mitral valve leaflets 1108 outwards.

Thus, after release of the distal anchors 80, the delivery system 10 can then be repositioned as needed so that the ends of the left distal anchors 80 are at the same level of the free edge of the native mitral valve leaflets 1108. The delivery system 10 can also be positioned to be coaxial to the mitral annulus 1106 if possible while still reducing contact with the left ventricular wall, the left atrial wall, and/or the annulus 1106.

In some embodiments, only the distal anchors 80 are released in the left atrium 1078 before the prosthesis 70 is move to a position within, or below, the annulus. In some alternate embodiments, the distal end of the prosthesis 70 can be further expanded in the left atrium 1078. Thus, instead of the distal anchors 80 flipping and no portion of the prosthesis 70 body expanding, a portion of the prosthesis 70 can be exposed and allowed to expand in the left atrium 1078. This partially exposed prosthesis 1010 can then be passed through the annulus 1106 into the left ventricle 1080. Further, the proximal anchors, if any, can be exposed. In some embodiments, the entirety of the prosthesis 70 can be expanded within the left atrium 1078.

To facilitate passage through the annulus 1106, the delivery system 10 can include a leader element (not shown) which passes through the annulus 1106 prior to the prosthesis 70 passing through the annulus 1106. For example, the leader element can include an expandable member, such as an expandable balloon, which can help maintain the shape, or expand, the annulus 1106. The leader element can have a tapered or rounded shape (e.g., conical, frustoconical, semispherical) to facilitate positioning through and expansion of the annulus 1106. In some embodiments, the delivery system 10 can include an engagement element (not shown) which can apply a force on the prosthesis 70 to force the prosthesis 70 through the annulus 1106. For example, the engagement element can include an expandable member, such as an expandable balloon, positioned within or above the prosthesis 70.

In some embodiments, to facilitate passage through the annulus 1106, a user can re-orient the prosthesis 70 prior to passing the prosthesis 70 through the annulus 1106. For example, a user can re-orient the prosthesis 70 such that it passes through the annulus 1106 sideways.

However, if only the distal anchors 80 are flipped, and no other expansion occurs, the prosthesis can be partially expanded in the ventricle 1080. Thus, when the prosthesis 70 is in the proper location, the distal end can be allowed to expand to capture the leaflets 1108. If the distal end is already expanded, no more expansion may take place or the distal end can be further expanded.

Further, the PML and AML 1106 can be captured, for example by adjusting the depth and angle of the prosthesis 70. If a larger prosthesis diameter is needed to capture the leaflets 1106, the outer sheath assembly 22 can be retracted until the desired diameter of the prosthesis 70 is achieved. Capture of the leaflets 1106 can be confirmed through echo imaging. In some embodiments, a user can confirm that the prosthesis 70 is still in the appropriate depth and has not advanced into the left ventricle 1080. The position can be adjusted as needed.

In some embodiments, once the distal anchors 80 enter the left ventricle 1080 the system 10 can be pulled backwards (e.g., towards the left atrium 1078) to fully capture the leaflets 1108. In some embodiments, the system 10 does not need to be pulled backwards to capture the leaflets 1108. In some embodiments, systolic pressure can push the leaflets 1108 upwards to be captured by the distal anchors 80. In some embodiments, systolic pressure can push the entire prosthesis 70 up towards the mitral annulus 1106 after the leaflets 1108 are captured and the prosthesis 70 is fully or partially released. In some embodiments, a user can rotate the delivery system 10 and/or prosthesis 70 prior to and/or while pulling the delivery system 10 backwards. In some instances, this can beneficially engage a greater number of chordae tendineae.

The outer sheath assembly 22 can be further retracted to fully expand the prosthesis. Once the prosthesis 70 is fully exposed, the delivery system 10 can be maneuvered to be coaxial and height relative to the mitral annulus 1106, such as by flexing, translating, or rotating the delivery system 10. As needed, the prosthesis 70 can be repositioned to capture the free edge of the native mitral valve leaflets 1108. Once full engagement of the leaflets 1108 is confirmed, the prosthesis 70 can be set perpendicular (or generally perpendicular) to the mitral annular plane.

Following, the mid shaft assembly 21 can be withdrawn. The mid shaft assembly 21 can then be reversed in direction to relieve any tension on the delivery system 10.

Below is a discussion of proximal anchors 82, though some embodiments of the prosthesis 70 may not include them. In some embodiments, proximal anchors 82 may not be released from the system 10 until the distal anchors 80 have captured the leaflets 1108. In some embodiments, proximal anchors 82 may be released from the system 10 prior to the distal anchors 80 capturing the leaflets 1108. In some embodiments, the proximal anchors 82 can be released when the distal anchors 80 are super or intra annular and the expanded prosthesis 70 (either partially or fully expanded) can be translated through the mitral annulus 1106. In some embodiments, the proximal anchors 82 could be released when the distal anchors 80 are sub-annular and the entire prosthesis 70 can be pulled up into the left atrium 1078 such that the proximal anchors 82 are supra-annular prior to release. In some embodiments, the proximal anchors 82 could be intra-annular prior to release and the systolic pressure could push the prosthesis 70 atrially such that the proximal anchors 82 end up supra-annular.

After, the leaflet capture and positioning of the prosthesis 70 can be confirmed, along with the relatively perpendicular position with respect to the mitral annular plane. In some embodiments, the nosecone 28 can then be withdrawn until it is within the prosthesis 70. The mid shaft assembly 21 can be further retracted until the prosthesis 70 is released from the delivery system 10. Proper positioning of the prosthesis 70 can be confirmed using TEE and fluoroscopic imaging.

Following, the delivery system 10 can be centralized within the prosthesis 70. The nosecone 28 and delivery system 10 can then be retracted into the left atrium 1078 and removed.

This intra-super annulus release can have a number of advantages. For example, this allows the distal anchors 82 to be properly aligned when contacting the chordae 1110. If the distal anchors 82 were released in the left ventricle 1080, this could cause misalignment or damage to heart tissue, such as the leaflets 1108 or chordae 1110.

In an alternate delivery approach, the delivery system 10 can be translated into the left ventricle 1080 prior to release of the prosthesis 70. Thus, the distal end of the prosthesis 70, and thus the distal anchors 82, can be released and flipped partially, or fully within the left ventricle 1080. Accordingly, in some embodiments the anchors 70 can be released/flipped below the mitral annulus 1106, just below the mitral annulus 1106, and/or below the free edges of the leaflets 1108. Further, the anchors 70 can be released above the papillary heads. Similar methodology as discussed above can then be used to properly position the prosthesis 70 and remove the delivery system 10 to deliver the prosthesis 1010. Further, in some embodiments the distal anchors 82 can be released without expanding the prosthesis initially in the ventricle 1080.

Alternative Delivery System

Figure 25:
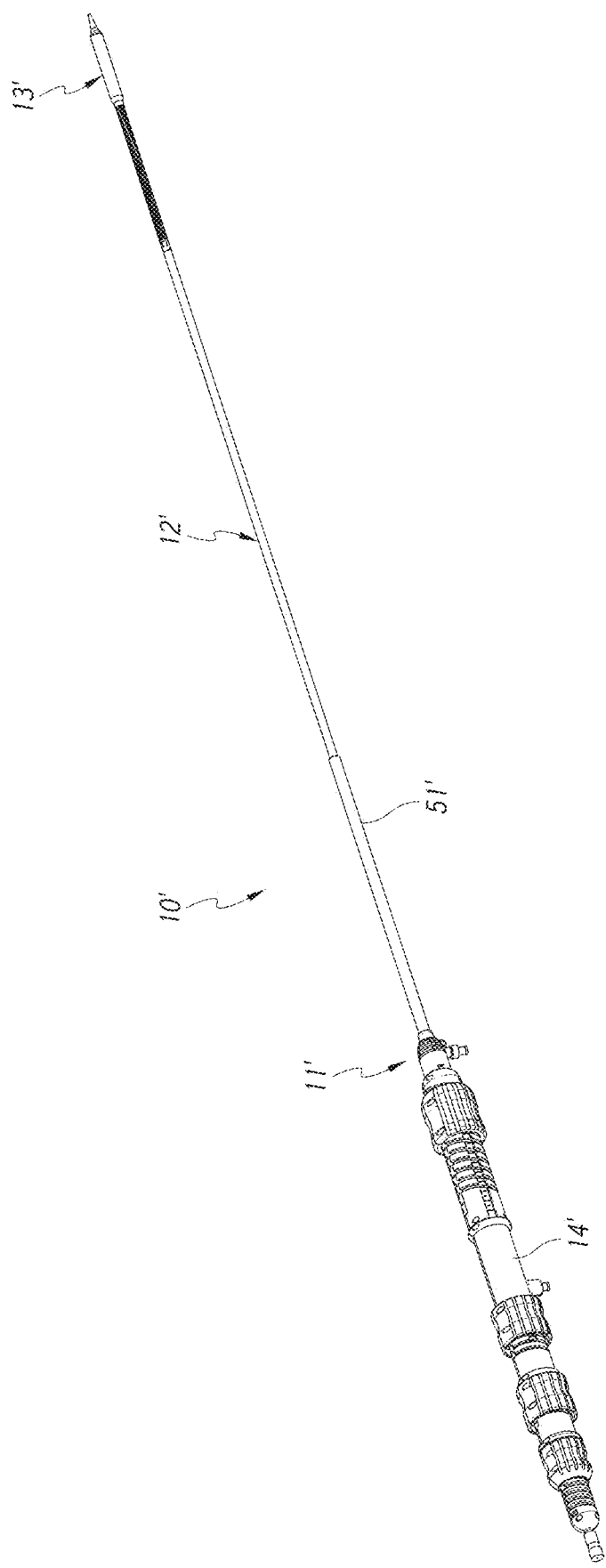
FIG. 25 shows an alternate embodiment of a delivery system.

FIG. 25 illustrates an embodiment of an alternate delivery device, system, or assembly 10. This delivery system 10' can include any or all of the components discussed above with respect to delivery system 10. Further, delivery system 10 can include any or all of the components discussed below with respect to delivery system 10'.

Similar to the embodiment of FIG. 1 described above, as shown in FIG. 25, the delivery system 10' can include a shaft assembly 12' comprising a proximal end 11' and a distal end 13', wherein a handle 14' is coupled to the proximal end of the assembly 12'. The shaft assembly 12' can be used to hold a prosthesis as described elsewhere herein for advancement of the same through the vasculature to a treatment location. The delivery system 10' can further comprise a relatively rigid live-on (or integrated) sheath 51' surrounding the shaft assembly 12' that can prevent unwanted motion of the shaft assembly 12'. The shaft assembly 12' can include an implant retention area 16' (shown in FIGS. 26A-B with FIG. 26A showing the prosthesis 70 and FIG. 26B with the prosthesis 70 removed) at its distal end that can be used for this purpose. In some embodiments, the shaft assembly 12' can hold an expandable prosthesis in a compressed state at implant retention area 16' for advancement of the prosthesis 70 within the body. The shaft assembly 12' may then be used to allow controlled expansion of the prosthesis 70 at the treatment location. The implant retention area 16' is shown in FIGS. 26A-B at the distal end of the delivery system, but may also be at other locations. In some embodiments, the prosthesis 70 may be rotated in the implant retention area 16', such as through the rotation of the inner shaft assembly 18' discussed herein.

As shown in cross-sectional view of FIGS. 26A-B, the distal end of the delivery system 10' can include one or more subassemblies such as an outer shaft assembly 12', inner shaft assembly 18', a rail assembly 20', and nose cone assembly 31' as will be described in more detail below.

In particular, embodiments of the disclosed delivery system can utilize a steerable rail in the rail assembly 20' for steering the distal end of the delivery system 10', allowing the implant to be properly located in a patient's body. Similar to the rail assembly described above, the steerable rail can be, for example, a rail shaft that extends through the delivery system 10' from the handle generally to the distal end. A user can manipulate the bending of the distal end of the rail, thereby bending the rail in a particular direction. In some embodiments, the rail can have more than one bend along its length, providing multiple directions of bending. As the rail is bent, it can press against the other assemblies to bend them as well, and thus the other assemblies of the delivery system 10' can be configured to steer along with the rail as, thus providing for full steerability of the distal end of the delivery system. Once the rail is steered into a particular location in a patient's body, the prosthesis 70 can be advanced along the rail and released into the body.

Starting with the outermost assembly, the delivery system can include an outer sheath assembly 22' forming a radially outer covering, or sheath, to surround an implant retention area 16' and prevent the implant from radially expanding. Moving radially inward, the inner shaft assembly 18' can be composed an inner shaft with its distal end attached to inner retention member or inner retention ring 40' for axially retaining the prosthesis. The inner shaft assembly 18' can be located within a lumen of the outer sheath assembly 22'. Moving further inwards, the rail assembly 20' can be configured for steerability, as mentioned above and further described below. The rail assembly 20' can be located within a lumen of the inner shaft assembly 18'. Further, the most radially-inward assembly is the nose cone assembly 31' which includes the nose cone shaft 27' having its distal end connected to the nose cone 28'. The nose cone assembly 31' can be located within a lumen of the rail shaft assembly 20'. The nose cone assembly 31' can include a lumen for a guide wire to pass through.

The shaft assembly 12', and more specifically the nose cone assembly 31', inner assembly 18', rail assembly 20', and outer sheath assembly 22', can be collectively configured to deliver a prosthesis 70 positioned within the implant retention area 16' (shown in FIG. 26A) to a treatment location. One or more of the subassemblies can then be moved to allow the prosthesis 70 to be released at the treatment location. For example, one or more of the subassemblies may be movable with respect to one or more of the other subassemblies. The handle 14' can include various control mechanisms that can be used to control the movement of the various subassemblies as will also be described in more detail below. In this way, the prosthesis 70 can be controllably loaded onto the delivery system 10' and then later deployed within the body. Further, the handle 14' can provide steering to the rail assembly 20', providing for bending/flexing/steering of the distal end of the delivery system 10'.

As will be discussed below, the inner retention member 40' and the outer sheath assembly 22' can cooperate to hold the prosthesis 70 in a compacted configuration. The inner retention member 40' is shown engaging struts 72 at the proximal end 301 of the prosthesis 70 in FIG. 26A. For example, slots located between radially extending teeth on the inner retention member 40' can receive and engage the struts 72 which may end in mushroom-shaped tabs 74 on the proximal end of the prosthesis 70. The outer sheath assembly 22' can be positioned over the inner retention member 40' so that the first end 301 of the prosthesis 70 is trapped there between, securely attaching it to the delivery system 10' between the outer sheath assembly 22' and the inner retention member 40'.

As shown in FIG. 26A, the distal anchors 80 can be located in a delivered configuration where the distal anchors 80 point generally distally (as illustrated, axially away from the main body of the prosthesis frame and away from the handle of the delivery system). The distal anchors 80 can be restrained in this delivered configuration by the outer sheath assembly 22'. Accordingly, when the outer sheath 22' is withdrawn proximally, the distal anchors 80 can flip positions to a deployed configuration (e.g., pointing generally proximally). FIG. 26A also shows the proximal anchors 82 extending distally in their delivered configuration within the outer sheath assembly 22'. In other embodiments, the distal anchors 80 can be held to point generally proximally in the delivered configuration and compressed against the body of the prosthesis frame.

The delivery system 10' may be provided to users with a prosthesis 70 preinstalled. In other embodiments, the prosthesis 70 can be loaded onto the delivery system shortly before use, such as by a physician or nurse.

As shown in FIG. 26B, there may not be an additional layer/shaft/member located between the inner retention member 40' and the outer sheath assembly 22'. By not having such a shaft, the overall diameter of the delivery system 10' can be reduced.

Figure 26C:
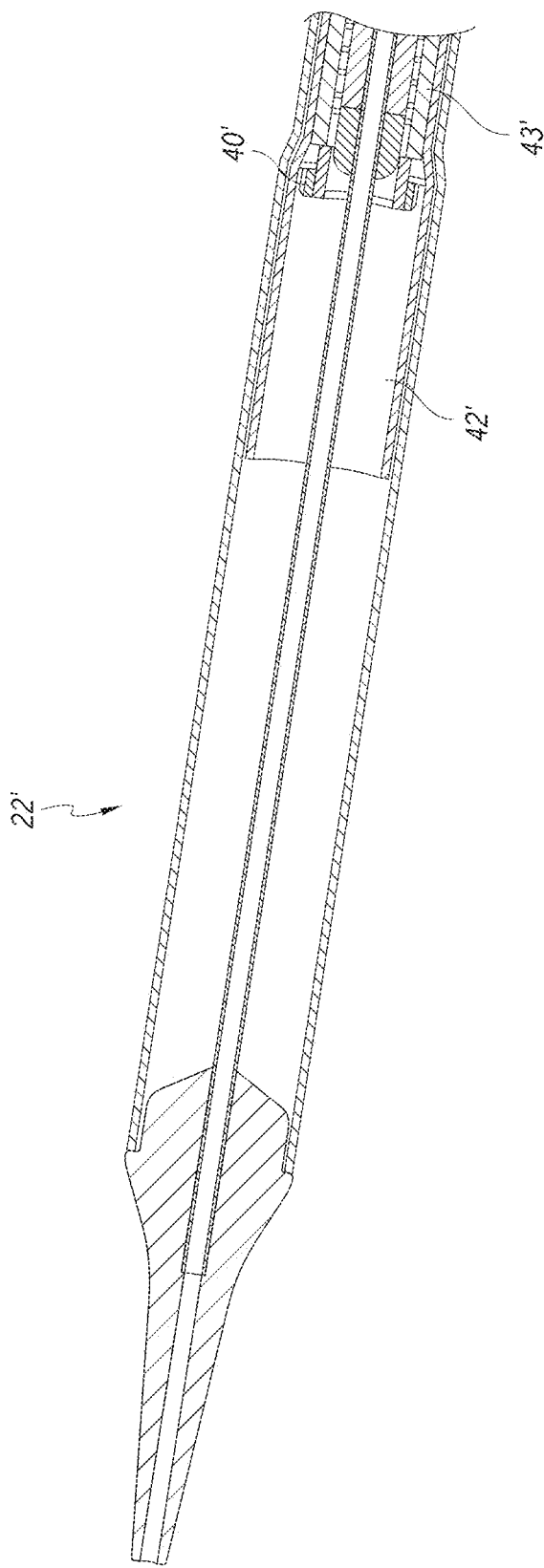
FIG. 26C shows a partial cross-sectional view of the distal end of a delivery system with a mid shaft assembly without the valve prosthesis of FIG. 3A.

However, in some embodiments, an outer retention member (or ring) 42' may be incorporated into the delivery system 10', as shown in FIG. 26C. The outer retention member 42' may be attached to a mid shaft 43' which can be attached at a proximal end to the handle 14'. The outer retention member 42' can provide further stability to the prosthesis 70 when in the compressed position. The outer retention member 42' can be positioned over the inner retention member 40' so that the proximal end of the prosthesis 70 is trapped therebetween, securely attaching it to the delivery system 10.

The outer retention member 42' can encircle a portion of the prosthesis 70, in particular the first end 301', thus preventing the prosthesis 70 from expanding. Further, the mid shaft 43 can be translated proximally with regards to the inner assembly 18' into the outer sheath assembly 22', thus exposing a first end 301' of the prosthesis 70 held within the outer retention member 42'. In this way the outer retention member 42' can be used to help secure a prosthesis 70 to or release it from the delivery system 10'. The outer retention member 42' can have a cylindrical or elongate tubular shape, and may sometimes be referred to as an outer retention ring.

Delivery System Assemblies

Figure 27:
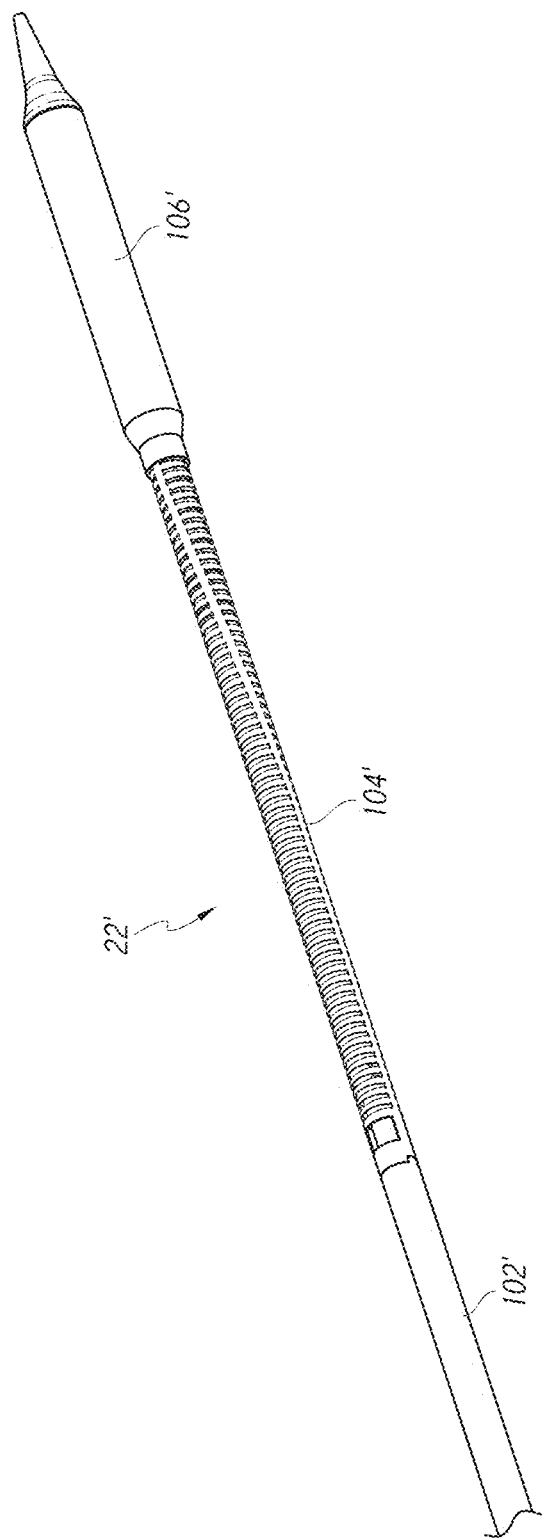
FIG. 27 shows a perspective view of the distal end of the delivery system of FIG. 25.
Figure 28:
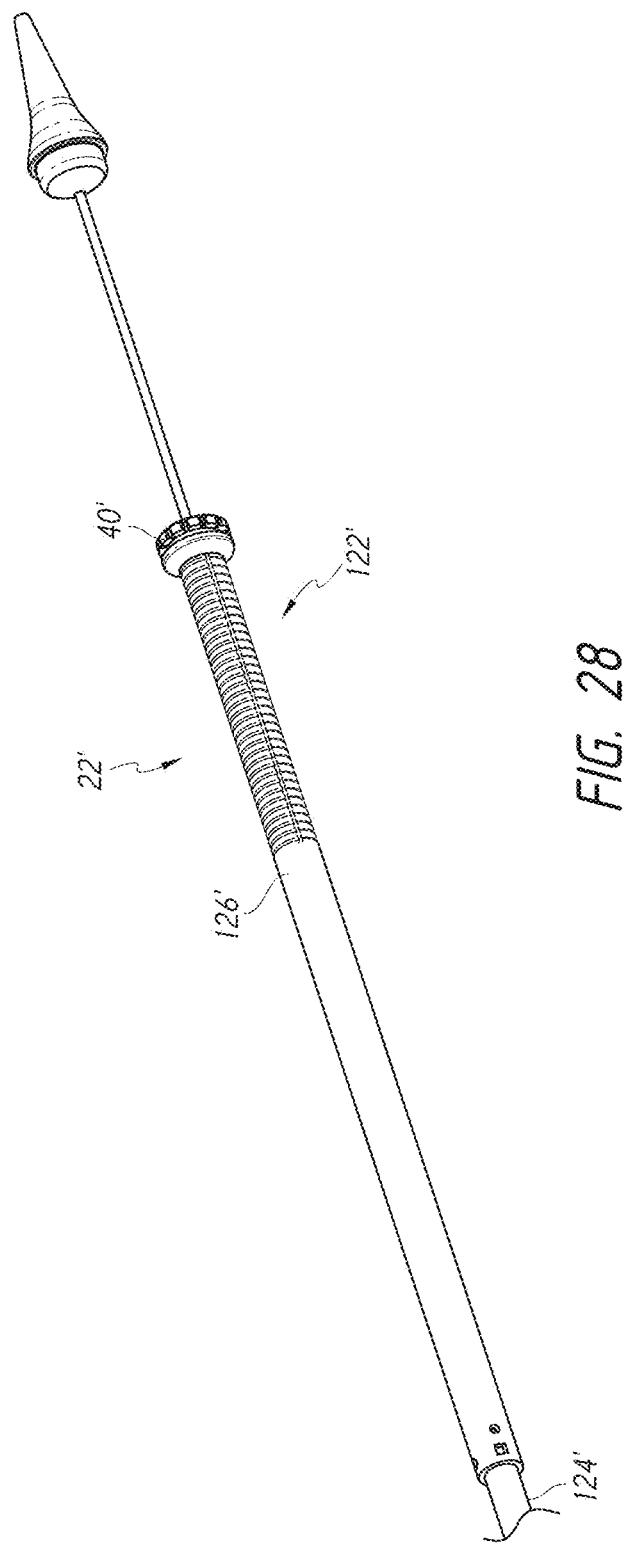
FIG. 28 show components of the delivery system of FIG. 27 with the outer sheath assembly moved proximally and out of view.
Figure 29:
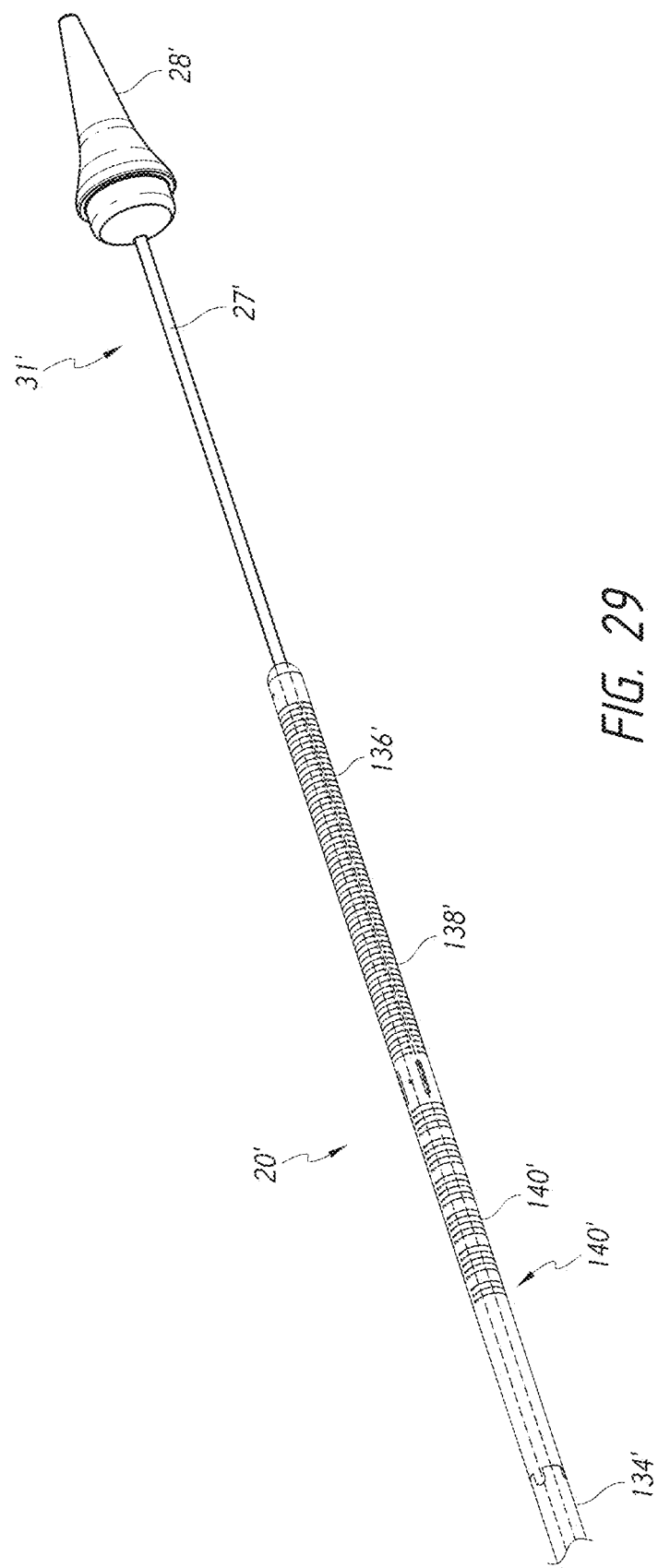
FIG. 29 show components of the delivery system of FIG. 28 with the inner assembly moved proximally and out of view.

FIGS. 27-29 illustrate further views of delivery system 10' with different assemblies translated proximally and described in detail.

Starting with the outermost assembly shown in FIG. 27, the outer sheath assembly 22' can include an outer proximal shaft 102' directly attached to the handle 14' at its proximal end and an outer hypotube 104' attached at its distal end. A capsule 106' can then be attached generally at the distal end of the outer hypotube 104'. These components of the outer sheath assembly 22' can form a lumen for the other subassemblies to pass through.

The outer proximal shaft 102' may be a tube and is preferably formed plastic, but could also be a metal hypotube or other material. The outer hypotube 104' can be a metal hypotube which in some embodiments may be cut or have slots, as discussed in detail below. The outer hypotube 104' can be covered or encapsulated with a layer of ePTFE, PTFE, or other material so that the outer surface of the outer hypotube 104' is generally smooth.

The capsule 106' can be a tube formed of a plastic or metal material. In some embodiments, the capsule 106' is formed of ePTFE or PTFE. In some embodiments this capsule 106' can be relatively thick to prevent tearing and to help maintain a self-expanding implant in a compacted configuration. In some embodiments the material of the capsule 106' is the same material as the coating on the outer hypotube 104'. As shown, the capsule 106' can have a diameter larger than the outer hypotube 104', though in some embodiments the capsule 106' may have a similar diameter as the hypotube 104'. The capsule 106' can be configured to retain the prosthesis 70 in the compressed position within the capsule 106'.

The outer sheath assembly 22' is disposed so as to be slidable over the inner assembly 18', the rail assembly 20', and the nose cone assembly 31'.

Moving radially inwards, the next assembly is the inner shaft assembly 18'. FIG. 28 shows approximately the same view as FIG. 27, but with the outer sheath assembly 22' removed, thereby exposing the inner shaft assembly 18'. As may be noted, there is no additional outer retention mechanism or shaft, such as an outer retention ring, between the inner shaft assembly 18' and the outer sheath assembly 22'.

The inner shaft assembly 18' can include an inner shaft 122' generally attached at its proximal end to the handle 14', and an inner retention ring 40' located at the distal end of the inner shaft 122'. The inner shaft 122' itself can be made up of an inner proximal shaft 124' directly attached to the handle 14' at a proximal end and an inner hypotube 126' attached to the distal end of the inner proximal shaft 124'. Thus, the inner retention ring 40' can be attached generally at the distal end of the inner hypotube 126'. These components of the inner shaft assembly 18' can form a lumen for the other subassemblies to pass through.

Similar to the other assemblies, the inner proximal shaft 124' can comprise a tube, such as a hypodermic tube or hypotube (not shown). The tube can be made from one of any number of different materials including Nitinol, stainless steel, and medical grade plastics. The tube can be a single piece tube or multiple pieces connected together. Using a tube made of multiple pieces can allow the tube to provide different characteristics along different sections of the tube, such as rigidity and flexibility. The inner hypotube 126' can be a metal hypotube which in some embodiments may be cut or have slots as discussed in detail below. The tube 126' can be covered or encapsulated with a layer of ePTFE, PTFE, or other material so that the outer surface of the inner hypotube 126' is generally smooth.

The inner retention member 40' can be configured as a prosthesis retention mechanism that can be used to engage with the prosthesis, as discussed with respect to FIG. 26A. For example, the inner retention member 40' may be a ring and can include a plurality of slots configured to engage with struts 72 on the prosthesis 70. The inner retention member 40' can also be considered to be part of the implant retention area 16', and may be at the proximal end of the implant retention area 16'. With struts or other parts of a prosthesis 70 engaged with the inner retention member 40', the capsule can cover both the prosthesis and the inner retention member 40' to secure the prosthesis on the delivery system 10'. Thus, the prosthesis 70 can be sandwiched between the inner retention member 40' of the inner shaft assembly 18' and the capsule 106' of the outer sheath assembly 22'.

The inner shaft assembly 18' is disposed so as to be slidable over the rail assembly 20' and the nose cone assembly 31'.

Next, radially inwards of the inner shaft assembly 18' is the rail assembly 20' as shown in FIG. 29. The rail assembly can include a rail shaft 132' (or rail) generally attached at its proximal end to the handle 14'. The rail shaft 132' can be made up of a rail proximal shaft 134' directly attached to the handle at a proximal end and a rail hypotube 136' attached to the distal end of the rail proximal shaft 134'. The rail hypotube 136' can further include an atraumatic rail tip at its distal end. These components of the rail shaft assembly 20' can form a lumen for the other subassemblies to pass through.

Attached to an inner surface of the rail hypotube 136' are one or more pull wires which can be used apply forces to the rail hypotube 136' and steer the rail assembly 20'. The pull wires can extend distally from the knobs in the handle 14', discussed below, to the rail hypotube 136'. In some embodiments, pull wires can be attached at different longitudinal locations on the rail hypotube 136', thus providing for multiple bending locations in the rail hypotube 136', allowing for multidimensional steering.

In some embodiments, two distal pull wires 138' can extend to a distal section of the rail hypotube 136' and two proximal pull wires 140' can extend to a proximal section of the rail hypotube 136', however, other numbers of pull wires can be used, and the particular amount of pull wires is not limiting. For example, a single pull wire can extend to a distal location and a single pull wire can extend to a proximal location. In some embodiments, ring-like structures attached inside the rail hypotube 136', known as pull wire connectors, can be used as attachment locations for the pull wires. In some embodiments, the rail assembly 20' can include a distal pull wire connector and a proximal pull wire connector. In some embodiments, the pull wires can directly connect to an inner surface of the rail hypotube 136'.

The distal pull wires 138' can be connected (either on its own or through a connector) generally at the distal end of the rail hypotube 136'. The proximal pull wires 140' can connect (either on its own or through a connector) at a location approximately one quarter, one third, or one half of the length up the rail hypotube 136' from the proximal end. In some embodiments, the distal pull wires 138' can pass through small diameter pull wire lumens attached on the inside of the rail hypotube 136'. In some embodiments, the distal pull wires 138' can pass through small diameter coils and/or hypotubes to provide independent steering. The small diameter coils and/or hypotubes can be attached on the inside of the rail hypotube 136', which allows for both independent steering and flexibility in the shaft. This can prevent the wires 138' from pulling on the rail hypotube 136' at a location proximal to the distal connection. In some embodiments, these lumens can be attached to an outer surface of the nose cone shaft 31' distal to a location that the proximal pull wires 140' attach to the rail hypotube 136'.

For the pair of proximal pull wires 140', the wires can be spaced approximately 180° from one another to allow for steering in both directions. Similarly, for pair of distal pull wires 138', the wires can be spaced approximately 180° from one another to allow for steering in both directions. In some embodiments, the pair of distal pull wires 138' and the pair of proximal pull wires 140' can be spaced approximately 90° from each other. In some embodiments, the pair of distal pull wires 138' and the pair of proximal pull wires 140' can be spaced approximately 0° from each other. However, other locations for the pull wires can be used as well, and the particular location of the pull wires is not limiting.

The rail assembly 20' is disposed so as to be slidable over the nose cone assembly 31'.

Moving further inwards from the rail assembly is the nose cone assembly 31' also seen in FIG. 29. This may be a nose cone shaft 27', and in some embodiments, may have a nose cone 28' on its distal end. The nose cone 28' can be made of polyurethane for atraumatic entry and to minimize injury to venous vasculature. The nose cone 28' can also be radiopaque to provide for visibility under fluoroscopy.

The nose cone shaft 27' may include a lumen sized and configured to slidably accommodate a guide wire so that the delivery system 10' can be advanced over the guide wire through the vasculature. However, embodiments of the system 10' discussed herein may not use a guide wire and thus the nose cone shaft 27' can be solid. The nose cone shaft 27' may be connected from the nose cone 28' to the handle, or may be formed of different segments such as the other assemblies. Further, the nose cone shaft 27' can be formed of different materials, such as plastic or metal, similar to those described in detail above.

In some embodiments, one or more spacer sleeves (not shown) can be used between different assemblies of the delivery system 10'. For example, a first spacer sleeve can be located concentrically between the inner shaft assembly 18' and the rail assembly 20', generally between the inner and rail hypotubes 126'/136'. A second spacer sleeve can be located concentrically between the rail assembly 20' and the nose cone assembly 31', generally longitudinally within the rail hypotube 136'. The spacer sleeve can be made of a polymer material such as braided Pebax® and can be lined, for example with PTFE, on the inner diameter, though the particular material is not limiting. The spacer sleeve can advantageously reduce friction between the steerable rail assembly 20' and its surrounding assemblies. Thus, the spacer sleeves can act as a buffer between the rail assembly 20' and the inner/nose cone assembly 18730'. Further, the spacer sleeve can take up any gap in radius between the assemblies, preventing compressing or snaking of the assemblies during steering.

The spacer sleeve can be mechanically contained by the other lumens and components, and is thus not physically attached to any of the other components, allowing the spacer sleeve to be "floating" in that area. The floating aspect of the spacer sleeve allows it to move where needed during deflection and provide a support and/or lubricious bear surface/surfaces. Accordingly, the floating aspect allows the delivery system 10' to maintain flex forces. However, in some embodiments, the spacer sleeve can be connected to other components.

Hypotube Construction

Figure 30:
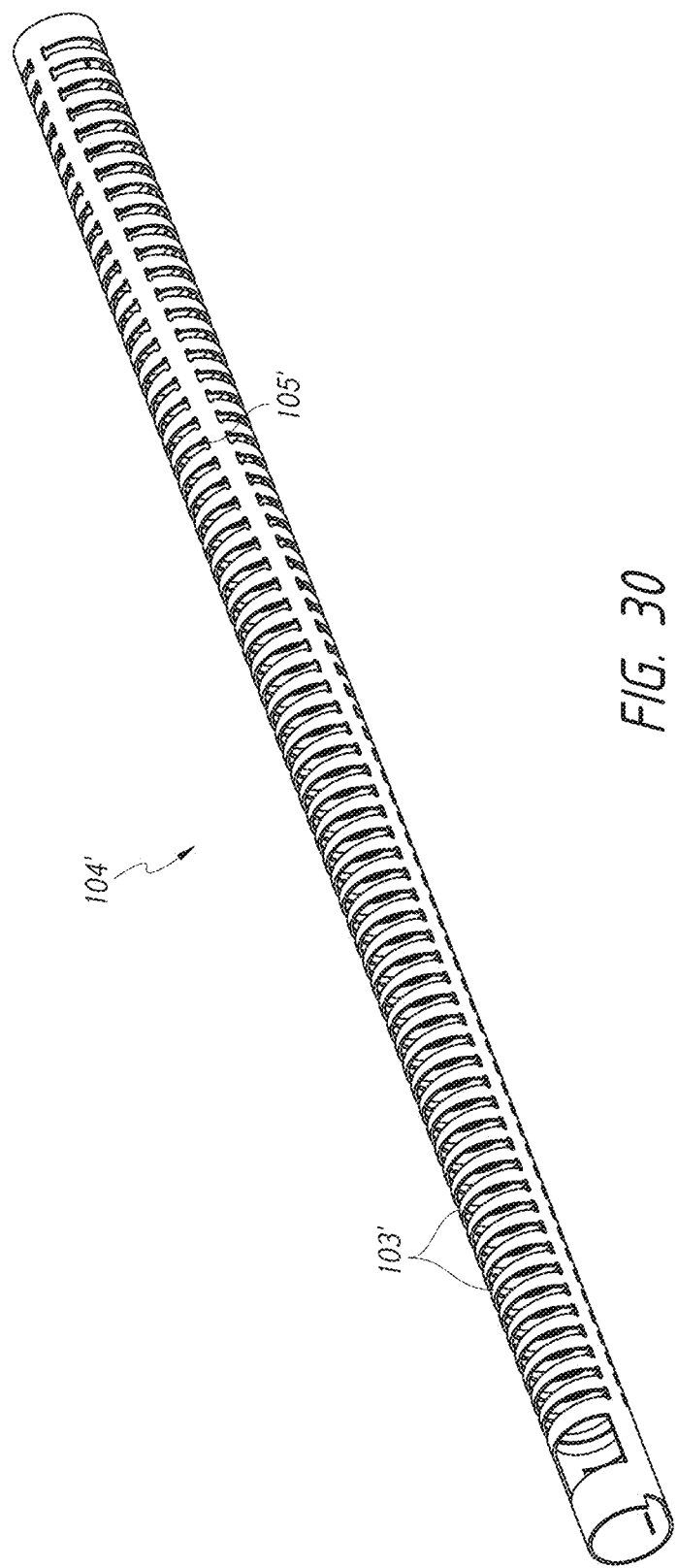
FIG. 30 illustrates an embodiment of an outer hypotube.
Figure 31:
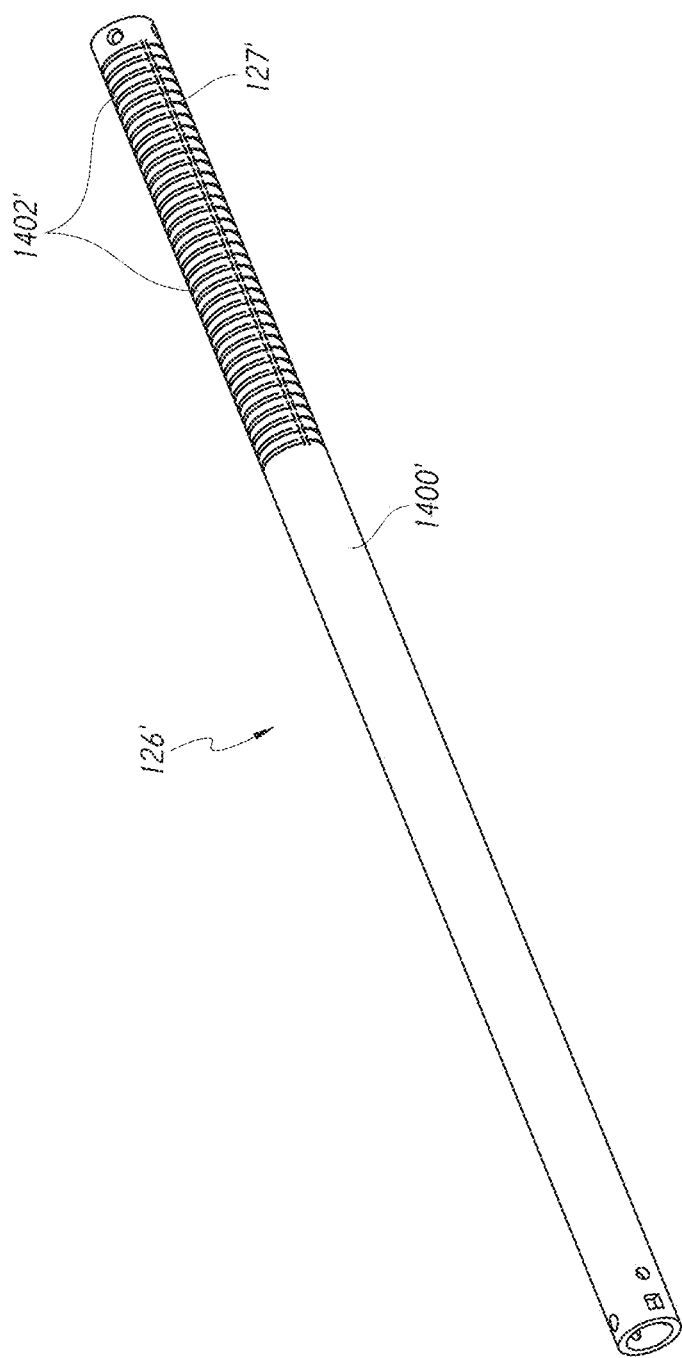
FIG. 31 illustrates an embodiment of an inner hypotube.
Figure 32:
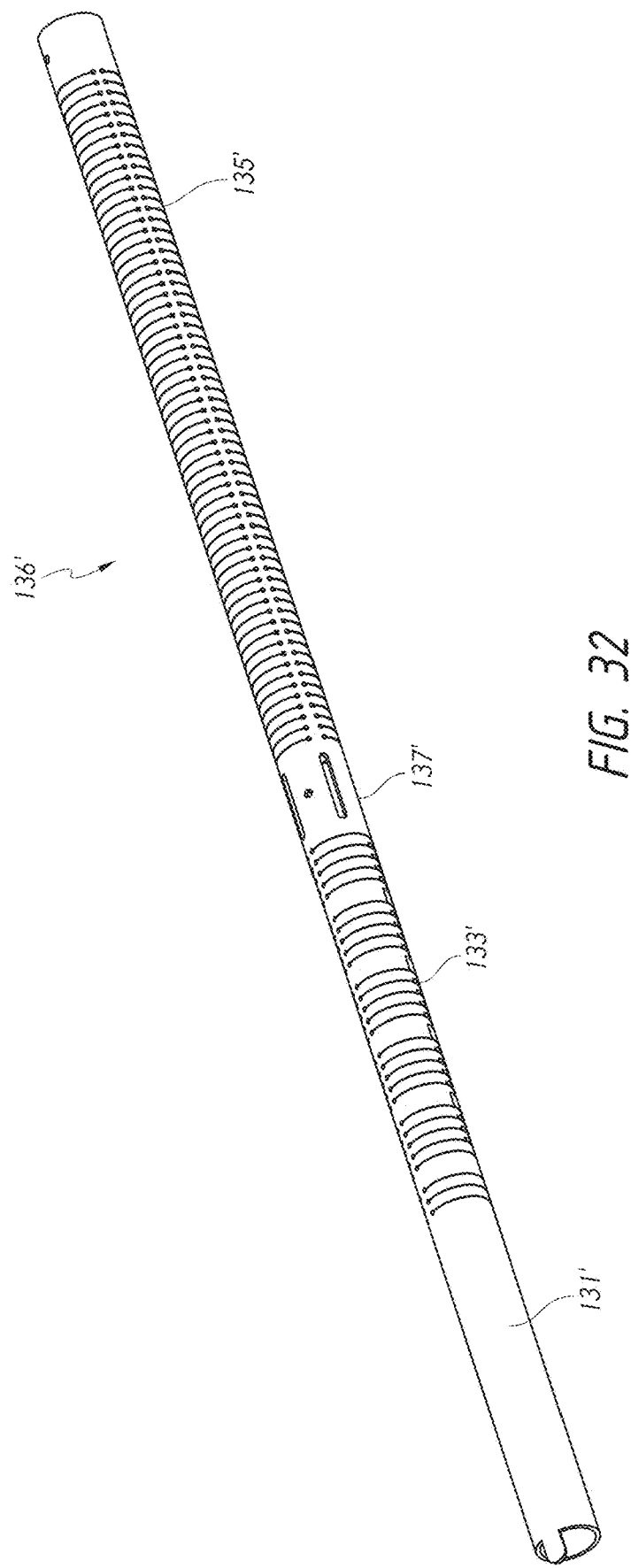
FIG. 32 illustrates an embodiment of a rail hypotube.

As discussed above, the outer sheath assembly 22', the inner assembly 18', and the rail assembly 20' can contain an outer hypotube 104', an inner hypotube 126', and a rail hypotube 136', respectively. Each of these hypotubes can be laser cut to include a number of slots, thereby creating a bending pathway for the delivery system to follow. While different slot assemblies are discussed below, it will be understood that any of the three hypotubes can have any of the slot configurations discussed below. FIGS. 30-32 show the different hypotubes in isolated format.

The outer hypotube 104', shown in FIG. 30 (distal end towards the right), can include a number slots 103' transverse to its lumen along most of the length of the outer hypotube 104'. Each of the slots can extend almost entirely around the circumference of the outer hypotube 104', thereby forming a single spine 105' of material extending between the proximal and distal ends of the outer hypotube 104'. In some embodiments, the outer hypotube 104' can contain more than one spine. As shown, the slots can extend generally from the proximal end of the outer hypotube 104' to the distal end of the hypotube 104', allowing the entirety of the outer hypotube 104' to more easily bend with the rail assembly 20'.

As shown, the spine 105' can circumferentially rotate while progressing from the proximal end to the distal end of the outer hypotube 104'. For example, the distal end of the spine 105' can be approximately 30°, 45°, 90°, 135°, or 180° offset from the proximal end of the spine 105'. In some embodiments, the spine 105' remains in the same circumferential location from the proximal end to approximately halfway the length of the outer hypotube 104'. At this point, the spine 105' can begin to circumferentially turn around the outer hypotube 104'. The curve of the spine helps direct the outer hypotube 105 during steering of the rail assembly 20'. The spine 105' generally follows the typical bend formed by the rail assembly 20' when entering the heart and directing towards the mitral valve, thus relieving some of the forces that may occur if the spine 105' was straight. However, in some embodiments the spine 105' of the outer hypotube 104' may be straight, and the particular configuration of the spine is not limiting.

Moving radially inwards in FIG. 31, the inner hypotube 126' also contains a number of slots 1402' (distal end towards the right). However, unlike the outer hypotube 104', the inner hypotube 126' in some embodiments does not contain slots along a majority of its length 1400', though in some embodiments it may. This allows the inner hypotube 126' to be more rigid as the inner hypotube 126' can experience a lot of compression and avoiding the spiral spine prevents coiling. Further, it allows the inner assembly 18' to direct the other assemblies to extend straight when advanced over the rail assembly 20', discussed below.

The inner hypotube 126' can contain slots transverse to its luminal axis along the distal ¼, ⅓, or ½ of its length starting generally from the distal end. In some embodiments, each circumferential position location can have two slots spanning less than 180°, thereby forming two spines 127' in the inner hypotube, unlike the single spine of the outer hypotube 104'. These spines 127' can be spaced approximately 180° apart, though in some embodiments different angles can be used depending on the desired bend. However, in some embodiments a single spine or more than two spines can be used. The additional spines can provide additional rigidity to the inner assembly 18'.

In some embodiments, the inner hypotube 126' can contain a single slot pattern forming the dual spines as discussed above. In some embodiments, the inner hypotube 126' can contain two different slot patterns. For example, at the distalmost end the slots may be configured for only one direction of bend (for example just on an X axis), making this section strong and robust but less flexible. However, slots in section proximal can be configured to includes multiple bending axis (such as an X axis and a Y axis), thus giving the inner hypotube 126' more flexibility for steering. In some embodiments, the configuration of the inner hypotube 126' creates forces that want to extend straight (e.g., not bend). Thus, when the inner hypotube 126' is advanced over the rail hypotube 136', it will achieve a straight configuration.

Next, again moving radially inward, FIG. 32 shows an embodiment of the rail hypotube 136' (distal end towards the right). The rail hypotube 136' can also contain a number of transverse slots. The rail hypotube can generally be broken into a number of different sections. At the most proximal end is an uncut (or unslotted) hypotube section 131'. This can take up approximately one quarter to one third of the rail hypotube 136'. Moving distally, the next section is the proximal slotted hypotube section 133'. This section includes a number of transverse slots cut into the rail hypotube. Generally, two slots are cut around each circumferential location forming almost half of the circumference. Accordingly, two backbones are formed between the slots extending up the length of the hypotube 136'. This is the section that can be guided by the proximal pull wires 140'. Moving further distally is the location 137' where the proximal pull wires 140' connect, and thus slots can be avoided. Thus section is just distal of the proximally slotted section.

Distally following the proximal pull wire connection area is the distal slotted hypotube section 135'. This section is similar to the proximal slotted hypotube section 133', but has significantly more slots cut out in an equivalent length. Thus, the distally slotted hypotube section 135' provides easier bending than the proximally slotted hypotube section 133'. In some embodiments, the proximal slotted section 133' can be configured to experience a bend of approximately 90 degrees with a half inch radius whereas the distal slotted section 135' can bend at approximately 180 degrees within a half inch. Further, as shown in FIG. 32, the spines of the distally slotted hypotube section 135' are offset from the spines of the proximally slotted hypotube section 133'. Accordingly, the two sections will achieve different bend patterns, allowing for three-dimensional steering of the rail assembly 20'. In some embodiments, the spines can be offset 30, 45, or 90 degrees, though the particular offset is not limiting.

At the distalmost end of the distal slotted hypotube section 135' is the distal pull wire connection area 139' which is again a non-slotted section of the rail hypotube 136'.

Handle

Figure 33:
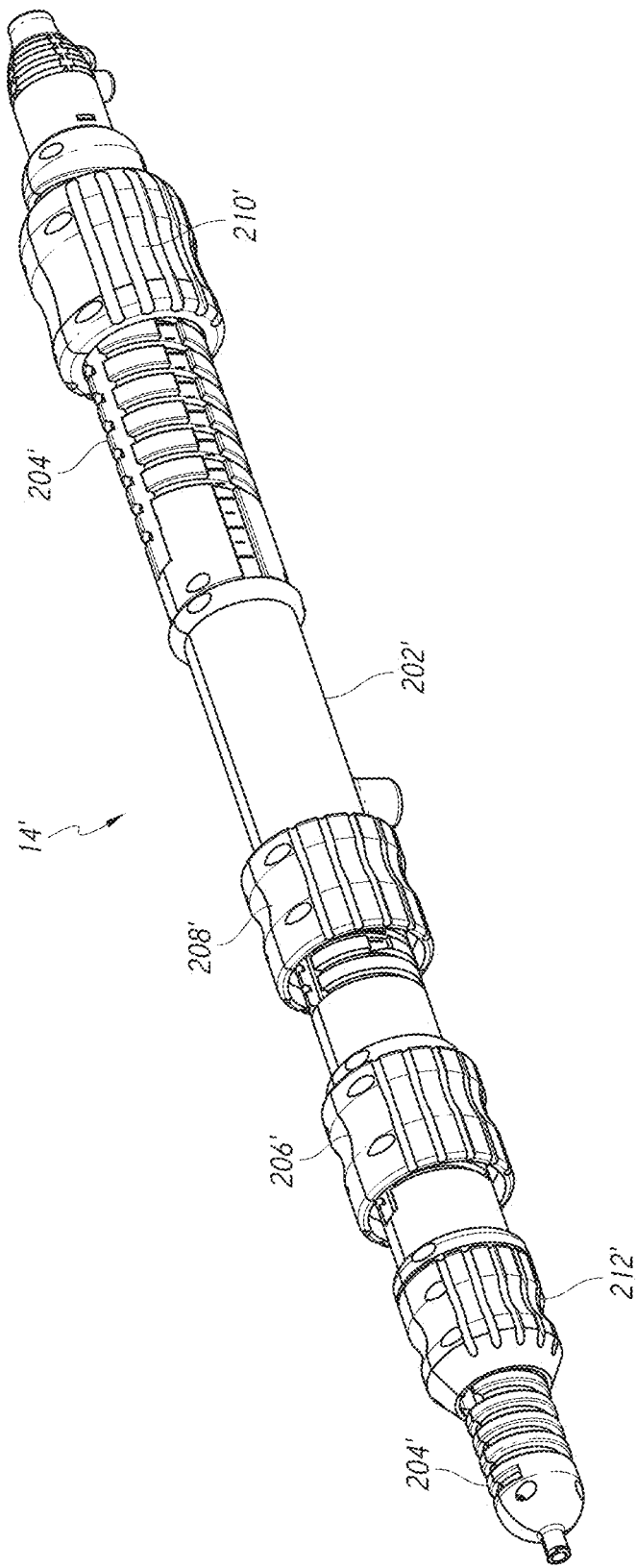
FIG. 33 illustrates an embodiment of a delivery system handle.

The handle 14' is located at the proximal end of the delivery system 10' and is shown in FIG. 33. It can include a number of actuators, such as rotatable knobs, that can manipulate different components of the delivery system. The operation of the handle 10' is described with reference to delivery of a replacement mitral valve prosthesis, though the handle 10' and delivery system 10' can be used to deliver other devices as well.

The handle 14' is generally composed of two housings, a rail housing 202' and a delivery housing 204', the rail housing 204' being circumferentially disposed around the delivery housing 204'. The inner surface of the rail housing 202 can include a screwable section configured to mate with an outer surface of the delivery housing 204'. Thus, the delivery housing 204' is configured to slide (e.g., screw) within the rail housing 202', as detailed below. The rail housing 202' generally surrounds about one half the length of the delivery housing 204', and thus the delivery housing 204' extends both proximally and distally outside of the rail housing 202'.

The rail housing 202' can contain two rotatable knobs, a distal pull wire knob 206' and a proximal pull wire knob 208'. However, the number of rotatable numbers on the rail housing 202' can vary depending on the number of pull wires being used. Rotation of the distal pull wire knob 206 can provide a proximal force, providing axial tension on the distal pull wires 138' and causing the distal slotted section 135' of the rail hypotube 136' to bend. The distal pull wire knob 206' can be rotated in either direction, allowing for bending in either direction. Rotation of the proximal pull wire knob 208' can provide a proximal force, and thus axial tension, on the proximal pull wires 140', thereby causing the proximal slotted section 133' of the rail hypotube 136' to bend. The proximal pull wire knob 108' can be rotated in either direction, allowing for bending in either direction. Thus, when both knobs are actuated, there can be two bends in the rail hypotube 136', allowing for three-dimensional steering of the rail shaft 132', and thus the distal end of the delivery system 10'. Further, the proximal end of the rail shaft 132' is connected on an internal surface of the rail housing 202'.

The bending of the rail shaft 132' can be used to position the system, in particular the distal end, at the desired patient location, such as at the native mitral valve. In some embodiments, rotation of the pull wire knobs 206'/208' can help steer the distal end of the delivery system 10' through the septum and left atrium and into the left ventricle so that the prosthesis 70 is located at the native mitral valve.

Moving to the delivery housing 204', the proximal ends of the inner shaft assembly 19', outer sheath assembly 22', and nose cone shaft assembly 30' can be connected to an inner surface of the delivery housing 204 of the handle 14'. Thus, they can move axially relative to the rail assembly 20' and rail housing 202'.

A rotatable outer sheath knob 210' can be located on the distal end of the delivery housing 204', being distal to the rail housing 202'. Rotation of the outer sheath knob 210' will pull the outer sheath assembly 22' in an axial direction proximally, thus pulling the capsule 106' away from the implant 70 and releasing the implant 70. The distal end 303' of the implant 70 can be released first, followed by release of the proximal end 301' of the implant 70 as the outer sheath knob 210' is continued to rotate.

On the proximal end of the delivery housing 204', and thus proximal to the rail housing 202', can be a rotatable depth knob 212'. As the depth knob 212' is rotated, the entirety of the delivery housing 204' moves distally or proximally with respect to the rail housing 202' which will remain in the same location. Thus, at the distal end of the delivery system 10', the inner shaft assembly 18', outer sheath assembly 22', and nose cone shaft assembly 30' move proximally or distally with respect to the rail assembly 20'. Accordingly, the rail shaft 132' can be aligned at a particular direction, and the other assemblies can move distally or proximally with respect to the rail shaft 132' for final positioning. The components can be advanced approximately 1, 2, 3, 5, 6, 7, 8, 9, or 10 cm along the rail shaft 132'. The components can be advanced more than approximately 1, 2, 3, 5, 6, 7, 8, 9, or 10 cm along the rail shaft 132'. The capsule 106' can then be withdrawn, releasing the implant 70. The assemblies other than the rail assembly 20' can then be withdrawn back over the rail shaft 132' by rotating the depth knob 212' in the opposite direction.

Delivery Method

Figure 34:
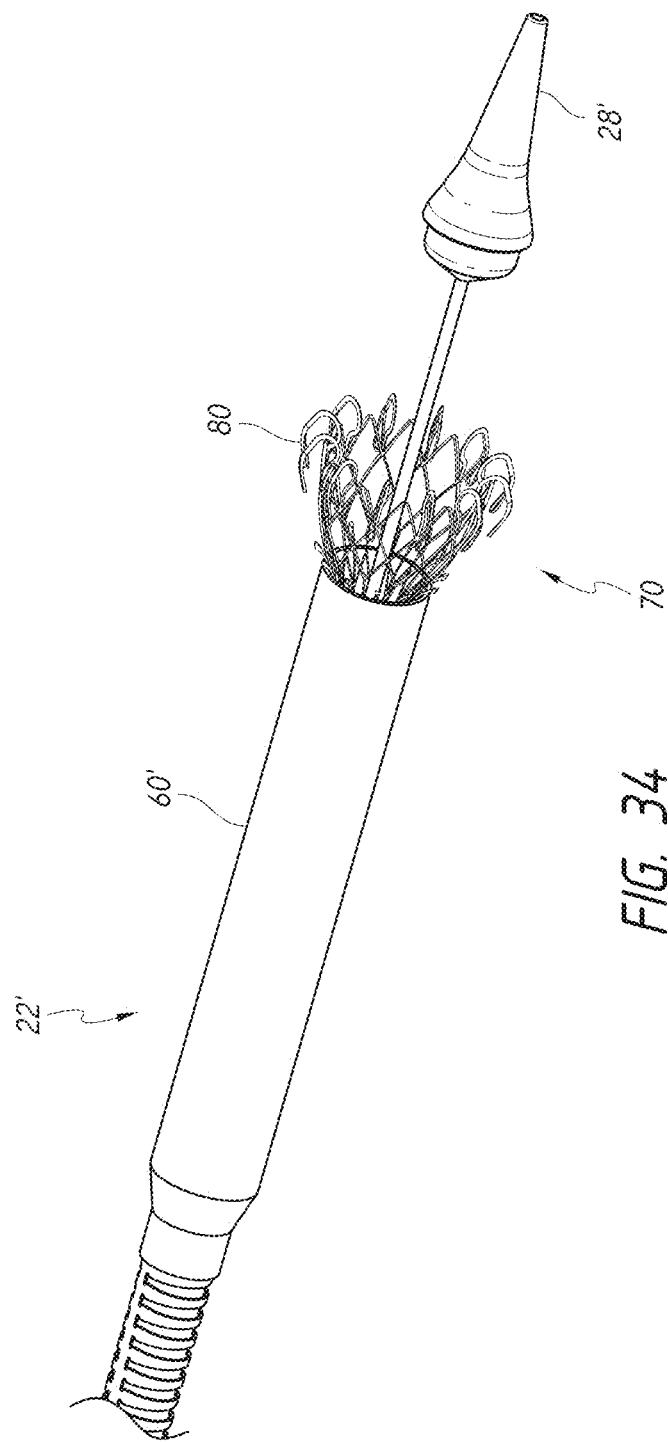
FIGS. 34-36 show steps of a method for delivery of the valve prosthesis to an anatomical location.
Figure 35:
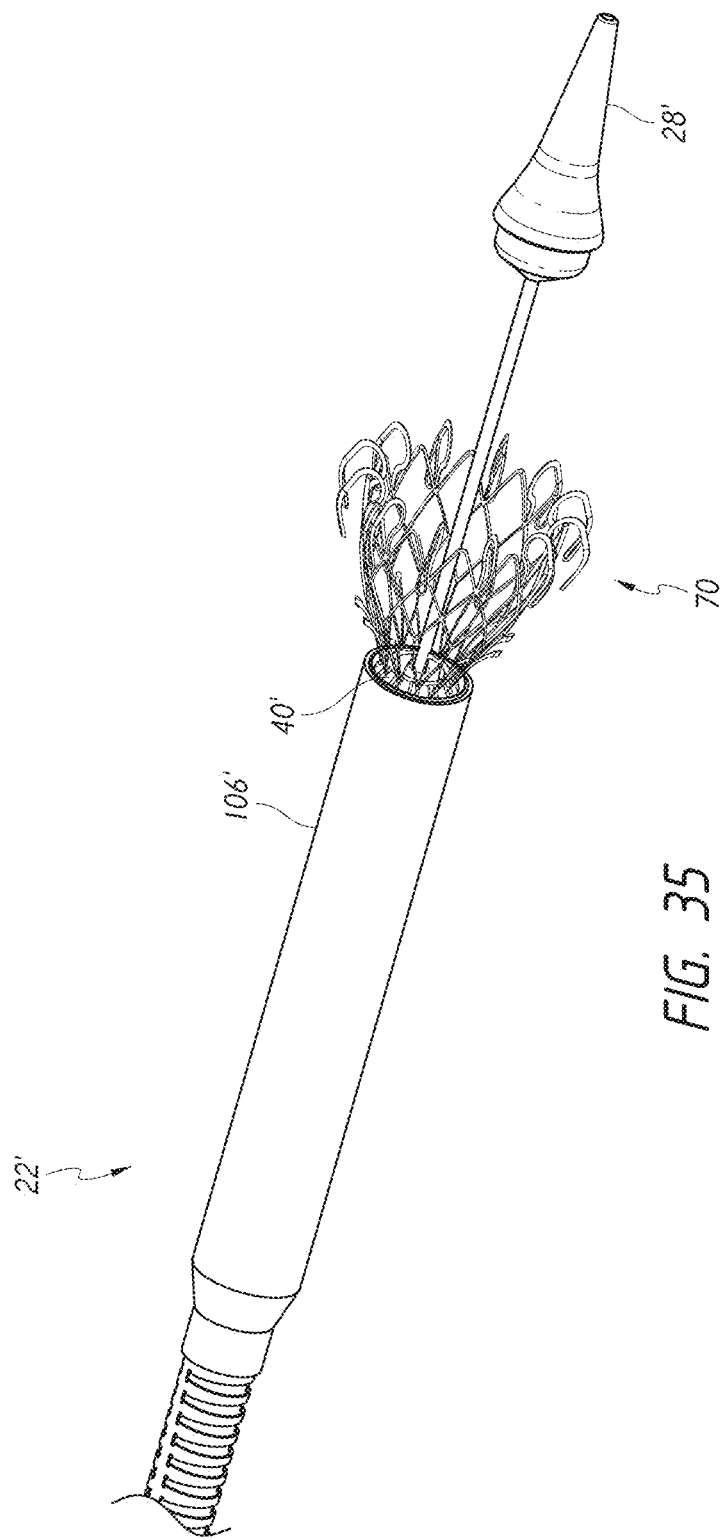
Figure 36:
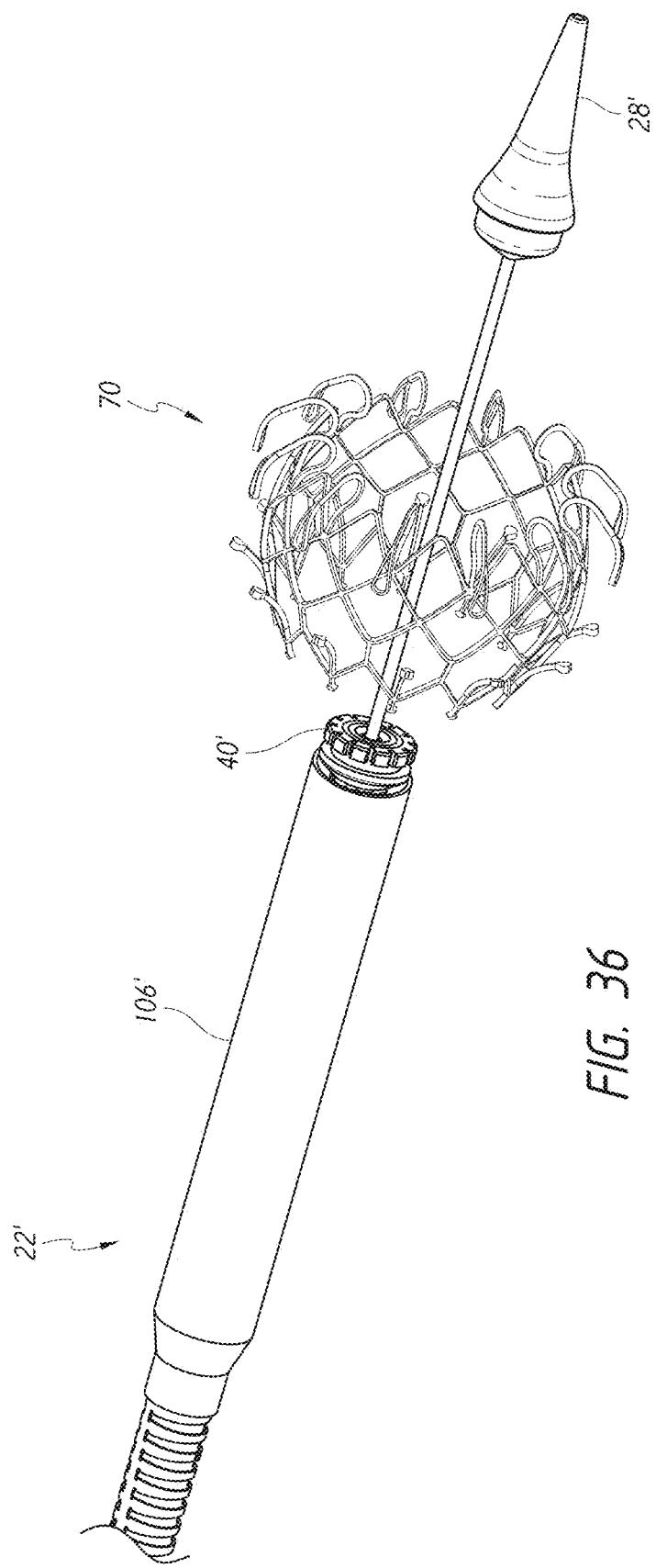

FIGS. 34-36 illustrate the release mechanism of the delivery system 10'. During the initial insertion of the prosthesis 70 and the delivery system 10' into the body, the prosthesis 70 can be located within the system 10', similar to as shown in FIG. 26A. The distal end 303' of the prosthesis 70, and specifically the distal anchors 80, are restrained within the capsule 106' of the outer sheath assembly 22', thus preventing expansion of the prosthesis 70. Similar to what is shown in FIG. 26A, the distal anchors 80 can extend distally when positioned in the capsule. The proximal end 301' of the prosthesis 70 is restrained within the capsule 106' and within a portion of the inner retention member 40' and thus is generally constrained between the capsule 106' and the inner retention member 40'.

The system 10' can first be positioned to a particular location in a patient's body, such as at the native mitral valve, through the use of the steering mechanisms discussed herein or other techniques.

Once the prosthesis 70 is loaded into the delivery system 10', a user can thread a guide wire into a patient to the desired location. The guide wire passes through the lumen of the nose cone assembly 31', and thus the delivery system 10' can be generally advanced through the patient's body following the guide wire. The delivery system 10' can be advanced by the user manually moving the handle 14' in an axial direction. In some embodiments, the delivery system 10' can be placed into a stand while operating the handle 14' controls.

Once generally in heart, the user can begin the steering operation of the rail assembly 20' using the distal pull wire knob 206' and/or the proximal pull wire knob 208'. By turning either of the knobs, the user can provide flexing/bending of the rail assembly 20' (either on the distal end or the proximal end), thus bending the distal end of the delivery system 10' into the desired configuration. As discussed above, the user can provide multiple bends in the rail assembly 20' to direct the delivery system 10' towards the mitral valve.

The user can also rotate and/or move the handle 14' itself in a stand for further fine tuning of the distal end of the delivery system 10'. The user can continually turn the proximal and/or distal pull wire knobs 208'/206', as well as moving the handle 14' itself, to orient the delivery system 10' for release of the prosthesis 70 in the body.

Following, the user can rotate the depth knob 212'. As discussed, rotation of this knob 212' advances the inner shaft assembly 18', outer sheath assembly 22', and nose cone assembly 31' over/through the rail assembly 20'. Due to the rigidity of, for example, the inner shaft assembly 18', these assemblies proceed straight forward in the direction aligned by the rail assembly 20'.

Once in the release position, the user can rotate the outer sheath knob 210', which translates the outer sheath assembly 22' (and thus the capsule 106') in a proximal direction towards the handle 14' as shown in FIG. 34. By doing so, the prosthesis 70 is uncovered in the body, allowing for the beginning of expansion. At this point, the distal anchors 80 can flip proximally and the distal end 303' begins to expand radially outward. For example, if the system 10' has been delivered to a native mitral valve location through a transseptal approach, the nose cone is positioned in the left ventricle, thus having the prosthesis 70 be generally perpendicular to the plane of the mitral annulus. The distal anchors 80 expand radially outward within the left ventricle. The distal anchors 80 can be located above the papillary heads, but below the mitral annulus and mitral leaflets. In some embodiments, the distal anchors 80 may contact and/or extend between the chordae in the left ventricle, as well as contact the leaflets, as they expand radially. In some embodiments, the distal anchors 80 may not contact and/or extend between the chordae or contact the leaflets. Depending on the position of the prosthesis 70, the distal ends of the distal anchors 80 may be at or below where the chordae connect to the free edge of the native leaflets.

With reference next to the step of FIG. 35, outer sheath assembly 22' can be further moved relatively away from the nose cone 28' to further uncover the prosthesis 70. As shown in the illustrated embodiment, the distal end 303' of the prosthesis 70 is expanded outwardly. It should be noted that the proximal end 301' of the prosthesis 70 can remain covered by the capsule 106' during this step such that the proximal end 301' remains in a radially compacted state. At this time, the system 10' may be withdrawn proximally so that the distal anchors 80 capture and engage the leaflets of the mitral valve, or may be moved proximally to reposition the prosthesis 70. Further, the system 10' may be torqued, which may cause the distal anchors 80 to put tension on the chordae through which at least some of the distal anchors may extend between. However, in some embodiments the distal anchors 80 may not put tension on the chordae. In some embodiments, the distal anchors 80 may capture the native leaflet and be between the chordae without any further movement of the system 10' after withdrawing the outer sheath assembly 22'.

Accordingly, during this step the system 10' may be moved proximally or distally to cause the distal or ventricular anchors 80 to properly capture the native mitral valve leaflets. In particular, the tips of the ventricular anchors 80 may be moved proximally to engage a ventricular side of the native annulus, so that the native leaflets are positioned between the anchors 80 and the body of the prosthesis 70. When the prosthesis 70 is in its final position, there may or may not be tension on the chordae, though the distal anchors 80 can be located between at least some of the chordae.

If an outer retention ring 42' is used, the distal end 303 of the prosthesis 70 will remain in the outer retention ring 42' after retraction of the capsule 106'. The outer retention ring 42' can then be retracted proximally to release the distal end 303 of the prosthesis 70.

As shown in FIG. 36, once the distal end 303 of the prosthesis 70 is fully expanded (or as fully expanded as possible at this point), capsule 106' can be further moved relatively proximally to expose the inner retention member 40', thus beginning the expansion of the proximal end 301 of the prosthesis 70. For example, in a mitral valve replacement procedure, after the distal or ventricular anchors 80 are positioned between at least some of the chordae tendineae and/or engage the native mitral valve annulus, the proximal end 301 of the prosthesis 70 may be expanded within the left atrium.

The capsule 106 can continue to be moved proximally such that the proximal end 301 of the prosthesis 70 can radially expand to its fully expanded configuration. After expansion and release of the prosthesis 70, the nose cone 28' can be withdrawn through the center of the expanded prosthesis 70 and into the outer sheath assembly 22'. The system 10' can then be removed from the patient.

Additional Valve Prostheses

Figure 37:
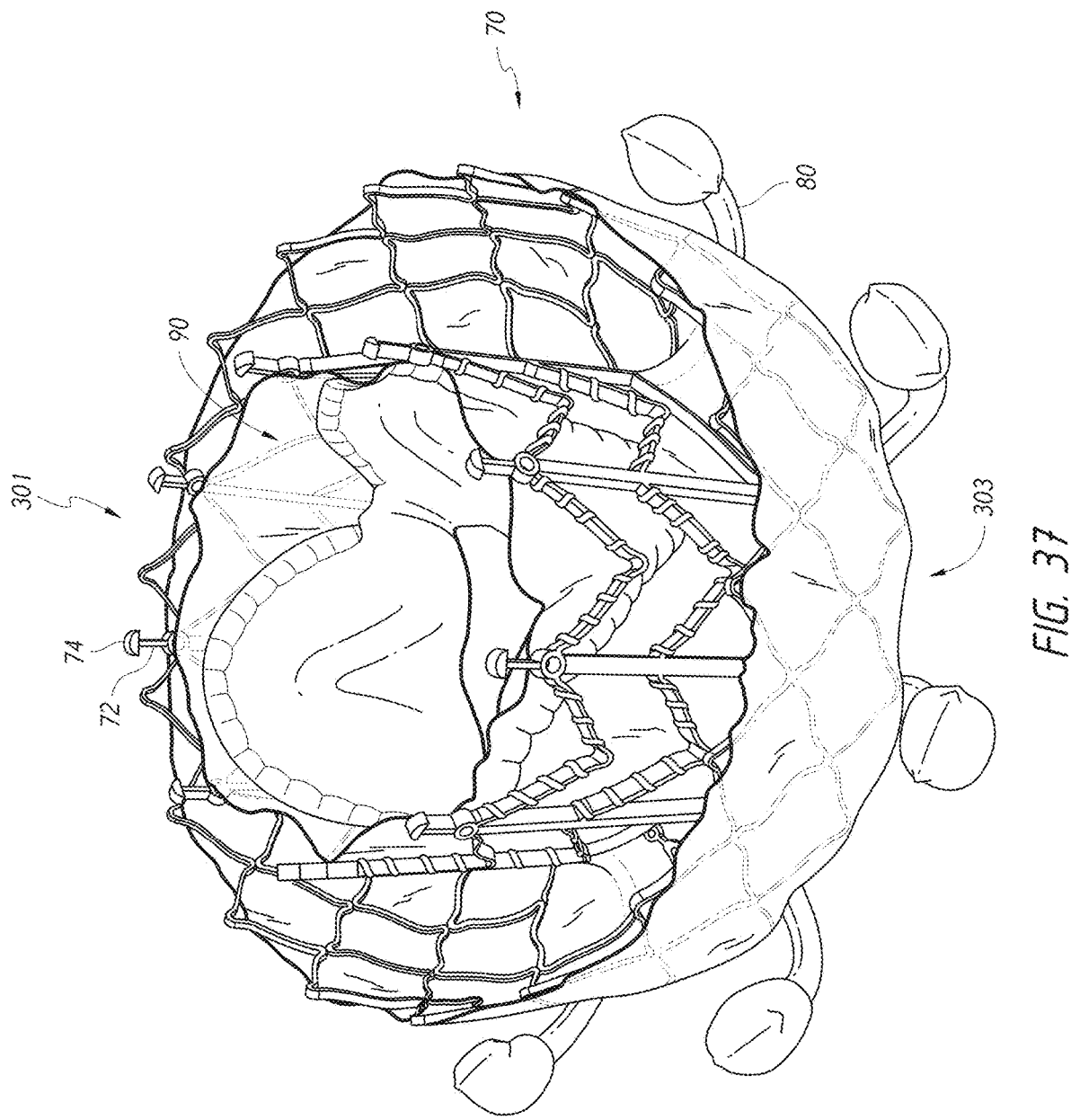
FIG. 37 shows a side view of an embodiment of a valve prosthesis that may be delivered using the delivery systems described herein.

FIGS. 37-50 illustrate alternative embodiments of a prosthesis that can used with the disclosed delivery systems 10 and methodology discussed herein. FIG. 37 illustrates one alternate embodiment of a prosthesis. Reference numbering of FIG. 37 are the same as discussed above with respect to FIG. 3A and further discussion can be found with respect to FIGS. 39-41 of U.S. Pat. Pub. No. 2018/0055629, hereby incorporated by reference in its entirety. FIGS. 38A-40 illustrates another alternate embodiment of a prosthesis, and further discussion can be found with respect to FIG. 33-35 of U.S. Pat. Pub. No. 2018/0055629 except that an outer frame anchoring feature is described in this publication. These embodiments can have similar or the same features to the prostheses discussed herein. In some embodiments, the prosthesis may be a single frame prosthesis. In some embodiments, the prosthesis may be a dual frame prosthesis. In some embodiments for use as a replacement mitral valve, the prosthesis includes distal or ventricular anchors similar to those described above (see, for example, anchoring feature 1524 described below), but does not include proximal or atrial anchors.

Figure 38A:
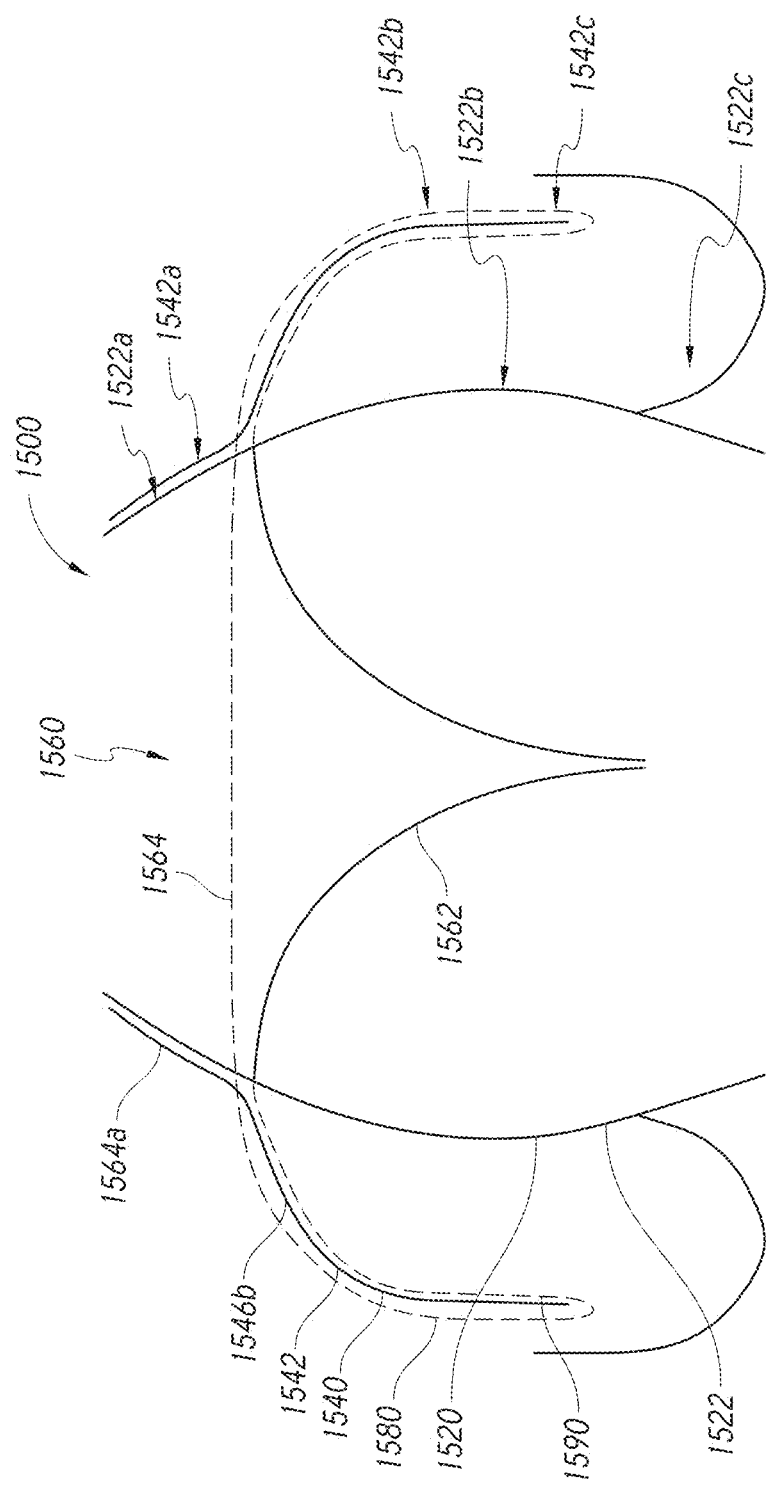
FIG. 38A-40 show views of an embodiment of a valve prosthesis that may be delivered using the delivery systems described herein.

With reference next to FIG. 38A, an embodiment of a prosthesis 1500 in an expanded configuration is illustrated. The prosthesis 1500 can include an inner frame 1520, an outer frame 1540, a valve body 1560, and one or more skirts, such as an outer skirt 1580 and an inner skirt 1590.

With reference first to the inner frame 1520, the inner frame 1520 can include an inner frame body 1522 and an inner frame anchoring feature 1524. The inner frame body 1522 can have an upper region 1522a, an intermediate region 1522*b*, and a lower region 1522*c*. As shown, the inner frame body 1522 can have a generally bulbous shape such that the diameters of the upper region 1522*a* and the lower region 1522*c* are less than the diameter of the intermediate region 1522*b*. The diameter of the upper region 1522*a* can be less than the diameter of the lower region 1522*c*. This can beneficially allow the use of a smaller valve body 1560 within the inner frame 1520 while allowing the inner frame body 1522 to have a larger diameter proximate the connection between the inner frame body 1522 and the inner frame anchoring feature 1524. This larger diameter can reduce the radial distance between the connection and the tip or end of the inner frame anchoring feature 1524. This can beneficially enhance fatigue resistance of the inner frame anchoring feature 1524 by reducing the length of the cantilever.

While the illustrated inner frame body 1522 is bulbous, it is to be understood that the diameters of the upper region 1522*a*, the intermediate region 1522*b*, and/or the lower region 1522*c* can be the same such that the inner frame body 1522 is generally cylindrical along one or more regions. Moreover, while the illustrated embodiment includes a lower region 1522*a* having a greater diameter than the upper region 1522*c*, it is to be understood that the diameters of the upper and lower regions 1522*a*, 1522*c* can be the same or the diameter of the upper region 1522*a* can be greater than the diameter of the lower region 1522*c*. Moreover, although the inner frame body 1522 has been described and illustrated as being cylindrical or having circular cross-sections, it is to be understood that all or a portion of the inner frame body 1522 can have a non-circular cross-section such as, but not limited to, a D-shape, an oval or an otherwise ovoid cross-sectional shape.

With reference next to the outer frame 1540 illustrated in FIG. 38A, the outer frame 1540 can be attached to the inner frame 1520 using any suitable fastener and/or other technique. Although the outer frame 1540 is illustrated as a separate component from the inner frame 1520, it is to be understood that the frames 1520, 1540 can be unitarily or monolithically formed.

As shown in the illustrated embodiment, the outer frame 1540 can include an outer frame body 1542. The outer frame body 1542 can have an upper region 1542*a*, an intermediate region 1542*b*, and a lower region 1542*c*. When in an expanded configuration such as a fully expanded configuration, the outer frame body 1542 can have an enlarged shape with the intermediate region 1542*b* and the lower region 1542*c* being larger than the upper region 1542*a*. The enlarged shape of the outer frame body 1542 can advantageously allow the outer frame body 1542 to engage a native valve annulus, native valve leaflets, or other tissue of the body cavity, while spacing the upper end from the heart or vessel wall.

The upper region 1542*a* of the outer frame body 1542 can include a first section 1546*a* and a second section 1546*b*. The first section 1546*a* can be sized and/or shaped to generally match the size and/or shape of the inner frame 1520. For example, the first section 1546*a* can have a curvature which matches a curvature of the upper region 1522*a* of the inner frame body 1522. The second section 1546*b* can extend radially outwardly away from the inner frame 1520. As shown in the illustrated embodiment, the transition between the first section 1546*a* and the second section 1546*b* can incorporate a bend such that the second section 1546*b* extends radially outwardly at a greater angle relative to the longitudinal axis.

The intermediate region 1542*b* of the outer frame body 1542 can extend generally downwardly from the outwardly-extending section 1546*b* of the upper region 1542*a*. As shown, the intermediate region 1542*b* can have a generally constant diameter from an upper end to a lower end such that the intermediate region 1542*b* forms a generally cylindrical shape. The lower region 1542*c* of the outer frame body 1542 can extend generally downwardly from the lower end of the intermediate region 1542*b*. As shown, the lower region 1542*c* of the outer frame body 1542 can have a generally constant diameter from an upper end to a lower end such that the lower region 1542*c* forms a generally cylindrical shape. As shown, the diameters of the intermediate region 1542*b* and the lower region 1542*c* are generally equivalent such that the intermediate region 1542*b* and the lower region 1542*c* together form a generally cylindrical shape.

While the intermediate and lower regions 1542*b*, 1542*c* have been described as cylindrical, it is to be understood that the diameters of the upper end, the lower end, and/or the portion therebetween can be different. For example, a diameter of the portion between the upper end and the lower end can be larger than the upper end and the lower end such that the intermediate region 1542*b* and/or lower region 1542*c* forms a generally bulbous shape. In some embodiments, the diameter of the lower end can be larger than the diameter of the upper end. In other embodiments, the diameter of the upper end can be larger than the diameter of the lower end. Moreover, although the outer frame body 1542 has been described and illustrated as being cylindrical or having circular cross-sections, it is to be understood that all or a portion of the outer frame body 1542 can be have a non-circular cross-section such as, but not limited to, a D-shape, an oval or an otherwise ovoid cross-sectional shape.

The outer frame 1540, such as the outer frame body 1542 can be used to attach or secure the prosthesis 1500 to a native valve, such as a native mitral valve. For example, the intermediate region 1542*b* of the outer frame body 1542 and/or the outer anchoring feature 1544 can be positioned to contact or engage a native valve annulus, tissue beyond the native valve annulus, native leaflets, and/or other tissue at or around the implantation location during one or more phases of the cardiac cycle, such as systole and/or diastole. As another example, the outer frame body 1542 can be sized and positioned relative to the inner frame anchoring feature 1524 such that tissue of the body cavity positioned between the outer frame body 1542 and the inner frame anchoring feature 1524, such as native valve leaflets and/or a native valve annulus, can be engaged or pinched to further secure the prosthesis 1500 to the tissue.

With continued reference to the prosthesis 1500 illustrated in FIG. 38A, the valve body 1560 is attached to the inner frame 1520 within an interior of the inner frame body 1522. The valve body 1560 functions as a one-way valve to allow blood flow in a first direction through the valve body 1560 and inhibit blood flow in a second direction through the valve body 1560.

The valve body 1560 can include a plurality of valve leaflets 1562, for example three leaflets 1562, which are joined at commissures. The valve body 1560 can include one or more intermediate components 1564. The intermediate components 1564 can be positioned between a portion of, or the entirety of, the leaflets 1562 and the inner frame 1520 such that at least a portion of the leaflets 1542 are coupled to the frame 1520 via the intermediate component 1564. In this manner, a portion of, or the entirety of, the portion of the valve leaflets 1562 at the commissures and/or an arcuate edge of the valve leaflets 1562 are not directly coupled or attached to the inner frame 1520 and are indirectly coupled or "float" within the inner frame 1520. For example, a portion of, or the entirety of, the portion of the valve leaflets 1562 proximate the commissures and/or the arcuate edge of the valve leaflets 1562 can be spaced radially inward from an inner surface of the inner frame 1520. By using one or more intermediate components 1564, the valve leaflets 1562 can be attached to non-cylindrical frames 1520 and/or frames 1520 having a diameter larger than that of the diameter of the valve leaflets 1562.

With reference next to the outer skirt 1580 illustrated in FIG. 38A, the outer skirt 1580 can be attached to the inner frame 1520 and/or outer frame 1540. As shown, the outer skirt 1580 can be positioned around and secured to a portion of, or the entirety of, the exterior of the outer frame 1540. The skirt 1580 can also be secured to a portion of the valve body 1560 such as, but not limited to, the intermediate components 1564. For example, the skirt 1580 can be attached to an inflow region of the intermediate components 1564. As shown, the outer skirt 1580 can follow the contours of the outer frame 1540; however, it is to be understood that at least a portion of the skirt 1580 can be spaced apart from at least a portion of both the inner frame 1520 and the outer frame 1540.

With reference next to the inner skirt 1590 illustrated in FIG. 38A, the inner skirt 1590 can be attached to the valve body 1560 and the outer skirt 1580. As shown, a first end of the inner skirt 1590 can be coupled to the valve body 1560 along portions of the valve body 1560 which are proximate the inner frame 1520. A second end of the inner skirt 1590 can be attached to the lower region of the outer skirt 1580. In so doing, a smooth surface can be formed under each of the leaflets. This can beneficially enhance hemodynamics by allowing blood to more freely circulate and reducing areas of stagnation. In some embodiments, the inner skirt 1590 can beneficially reduce contact between the outer frame body 1542 and the inner frame body 1522.

Although the prosthesis 1500 has been described as including an inner frame 1520, an outer frame 1540, a valve body 1560, and skirts 1580, 1590, it is to be understood that the prosthesis 1500 need not include all components. For example, in some embodiments, the prosthesis 1500 can include the inner frame 1520, the outer frame 1540, and the valve body 1560 while omitting the skirt 1580. Moreover, although the components of the prosthesis 1500 have been described and illustrated as separate components, it is to be understood that one or more components of the prosthesis 1500 can be integrally or monolithically formed. For example, in some embodiments, the inner frame 1520 and the outer frame 1540 can be integrally or monolithically formed as a single component.

Figure 38B:
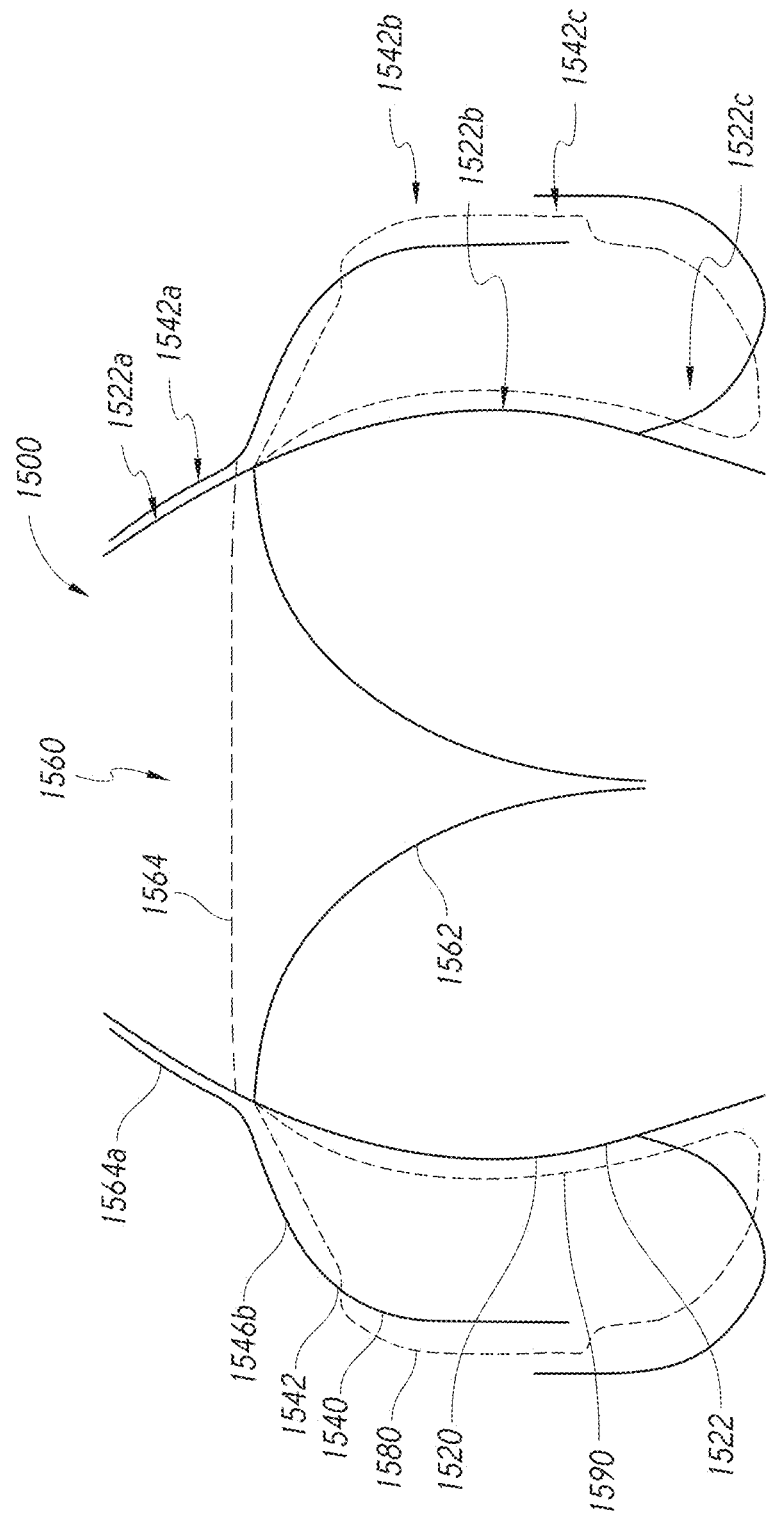

FIG. 38B illustrates an alternate embodiment of FIG. 38A with modifications to the design of the skirts (or cloth) 1580/1590. As shown, the skirts 1580/1590 can contact both the inner frame 1520 and outer frame 1540. The skirts 1580/1590 can start on the inside of the outer 1540, transition to the outside of the outer frame 1540, then attach to the bottom of the outside of the inner frame 1520, then proceed up along the outside of the inner frame 1520. By closing the skirts 1580/1590, this could avoid/reduce clot formation/embolization.

Figure 39:
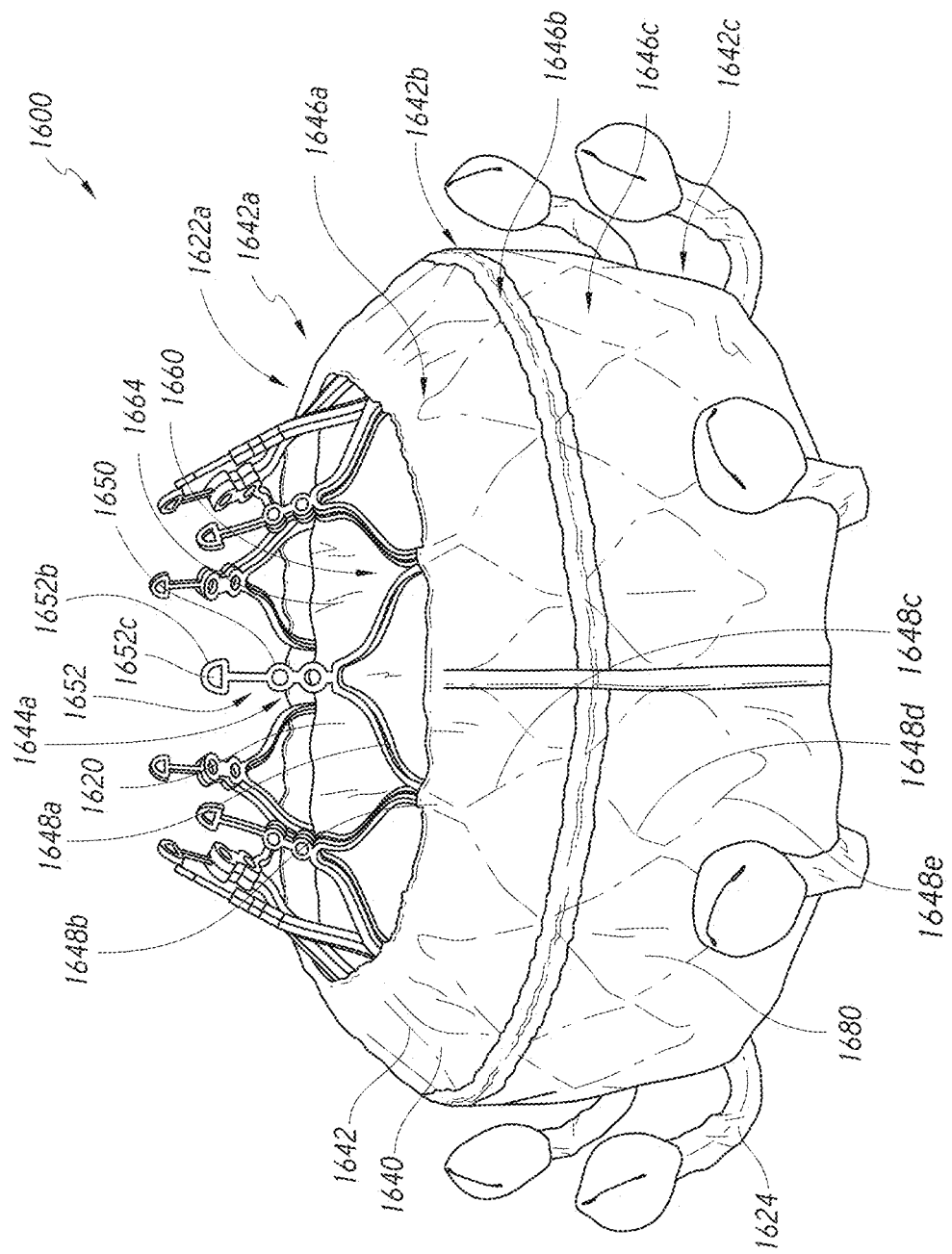
Figure 40:
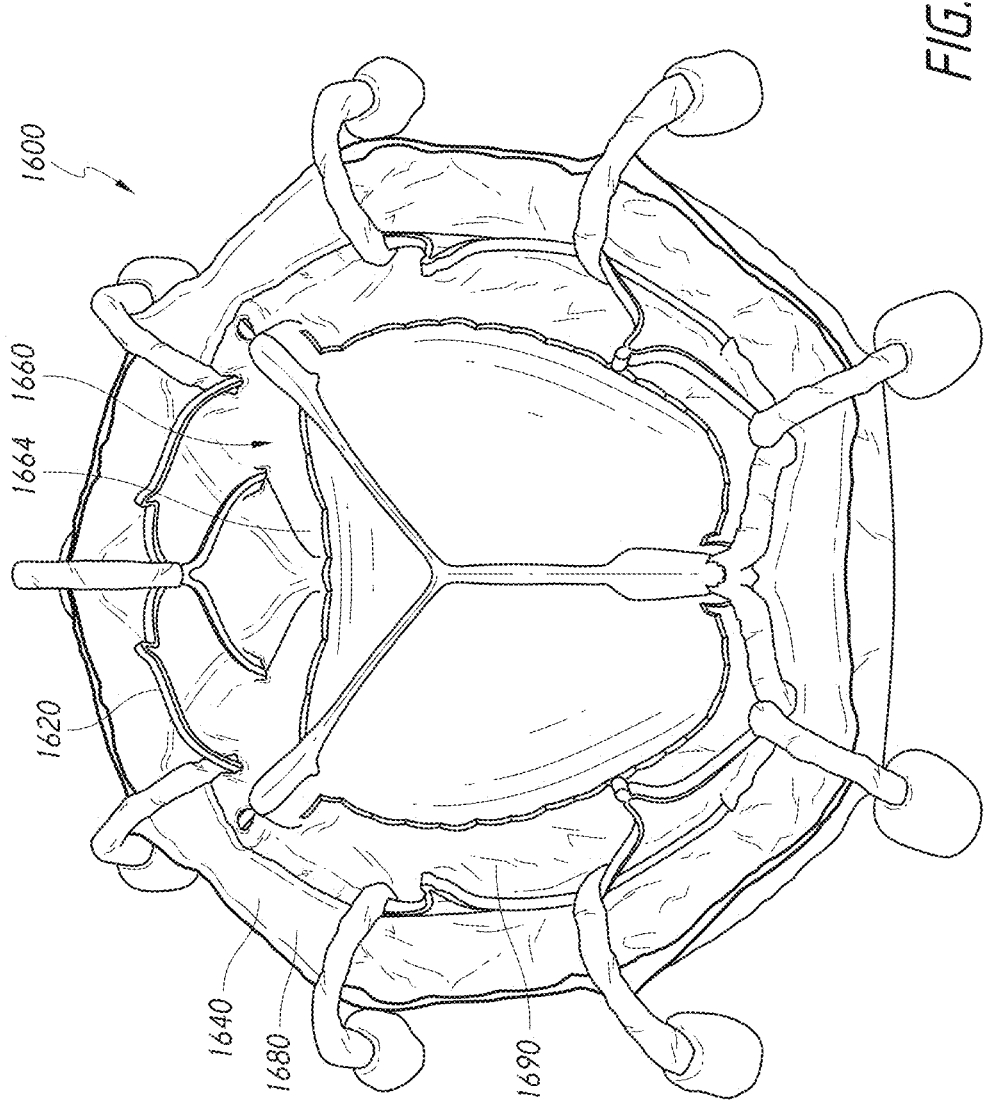

With reference next to FIGS. 39-40, an embodiment of a prosthesis 1600 in an expanded configuration is illustrated. This prosthesis 1600 may be similar in construction to the prosthesis 1500 described above. The prosthesis 1600 can include an inner frame 1620, an outer frame 1640, a valve body 1660, and one or more skirts, such as an outer skirt 1680 and an inner skirt 1690.

With reference first to the outer frame 1640 illustrated in FIGS. 39-40, the outer frame 1640 can be attached to the inner frame 1620 using any known fasteners and/or techniques. Although the outer frame 1640 is illustrated as a separate component from the inner frame 1620, it is to be understood that the frames 1620, 1640 can be unitarily or monolithically formed.

As shown in the illustrated embodiment, the outer frame 1640 can include an outer frame body 1642. The outer frame body 1642 can have an upper region 1642a, an intermediate region 1642b, and a lower region 1642c. At least a portion of the upper region 1642a of the outer frame body 1642 can be sized and/or shaped to generally match the size and/or shape of an upper region 1622a of the inner frame 1620. As shown in the illustrated embodiment, the upper region 1642a of the outer frame body 1642 can include one or more struts which generally match the size and/or shape of struts of the inner frame 1620. This can locally reinforce a portion of the prosthesis 1600 by effectively increasing the wall thickness of the combined struts.

When in an expanded configuration such as in a fully expanded configuration, the outer frame body 1642 can have a shape similar to that of outer frame body 1542 described above in connection with FIG. 38A. As shown, the intermediate region 1642b and the lower region 1642c can have a diameter which is larger than the diameter of the upper region 1642a. The upper region 1642a of the outer frame body 1642 can have a decreasing diameter from a lower end to an upper end such that the upper region 1642a is inclined or curved radially inwards towards the longitudinal axis of the prosthesis 1600. Although the outer frame body 1642 has been described and illustrated as being cylindrical or having circular cross-sections, it is to be understood that all or a portion of the outer frame body 1642 can be have a non-circular cross-section such as, but not limited to, a D-shape, an oval or an otherwise ovoid cross-sectional shape.

With continued reference to the outer frame 1600 illustrated in FIG. 39, the outer frame body 1642 can include a plurality of struts with at least some of the struts forming cells 1646a-c. Any number of configurations of struts can be used, such as rings of undulating struts shown forming ellipses, ovals, rounded polygons, and teardrops, but also chevrons, diamonds, curves, and various other shapes.

The upper row of cells 1646a can have an irregular octagonal shape such as a "heart" shape. This additional space can beneficially allow the outer frame 1640 to retain a smaller profile when crimped. The cell 1646a can be formed via a combination of struts. As shown in the illustrated embodiment, the upper portion of cells 1646a can be formed from a set of circumferentially-expansible struts 1648a having a zig-zag or undulating shape forming a repeating "V" shape. The struts 1648a can extend radially outwardly from an upper end to a lower end. These struts can generally match the size and/or shape of struts of the inner frame 1620.

The middle portion of cells 1646a can be formed from a set of struts 1648b extending downwardly from bottom ends of each of the "V" shapes. The struts 1648b can extend radially outwardly from an upper end to a lower end. The portion of the cells 1646a extending upwardly from the bottom end of struts 1648b may be considered to be a substantially non-foreshortening portion of the outer frame 1640.

The lower portion of cells 1646a can be formed from a set of circumferentially-expansible struts 1648c having a zig-zag or undulating shape forming a repeating "V" shape. As shown in the illustrated embodiment, the struts 1648c can incorporate a curvature such that the lower end of struts 1648c extend more parallel with the longitudinal axis than the upper end of the struts 1648c. One or more of the upper ends or tips of the circumferentially-expansible struts 1648c can be a "free" apex which is not connected to a strut. For example, as shown in the illustrated embodiment, every other upper end or tip of circumferentially-expansible struts 1648b is a free apex. However, it is to be understood that other configurations can be used. For example, every upper apex along the upper end can be connected to a strut.

The middle and/or lower rows of cells 1646b-c can have a different shape from the cells 1646a of the first row. The middle row of cells 1646b and the lower row of cells 1646c can have a diamond or generally diamond shape. The diamond or generally diamond shape can be formed via a combination of struts.

The upper portion of cells 1646b can be formed from the set of circumferentially-expansible struts 1648c such that cells 1646b share struts with cells 1646a. The lower portion of cells 1646b can be formed from a set of circumferentially-expansible struts 1648d. As shown in the illustrated embodiment, one or more of the circumferentially-expansible struts 1648d can extend generally in a downward direction generally parallel to the longitudinal axis of the outer frame 1640.

The upper portion of cells 1646c can be formed from the set of circumferentially-expansible struts 1648d such that cells 1646c share struts with cells 1646b. The lower portion of cells 1646c can be formed from a set of circumferentially-expansible struts 1648e. Circumferentially-expansible struts 1648e can extend generally in a downward direction.

As shown in the illustrated embodiment, there can be a row of nine cells 1646a and a row of eighteen cells 1646b-c. While each of the cells 1646a-c are shown as having the same shape as other cells 1646a-c of the same row, it is to be understood that the shapes of cells 1646a-c within a row can differ. Moreover, it is to be understood that any number of rows of cells can be used and any number of cells may be contained in the rows.

As shown in the illustrated embodiment, the outer frame 1600 can include a set of eyelets 1650. The upper set of eyelets 1650 can extend from an upper region 1642a of the outer frame body 1642. As shown, the upper set of eyelets 1650 can extend from an upper portion of cells 1646a, such as the upper apices of cells 1646a. The upper set of eyelets 1650 can be used to attach the outer frame 1640 to the inner frame 1620. For example, in some embodiments, the inner frame 1620 can include one or more eyelets which correspond to the eyelets 1650. In such embodiments, the inner frame 1620 and outer frame 1640 can be attached together via eyelets 1650 and corresponding eyelets on the inner frame 1620. For example, the inner frame 1620 and outer frame 1640 can be sutured together through said eyelets or attached via other means, such as mechanical fasteners (e.g., screws, rivets, and the like).

As shown, the set of eyelets 1650 can include two eyelets extending in series from each "V" shaped strut. This can reduce the likelihood that the outer frame 1640 twists along an axis of the eyelet. However, it is to be understood that some "V" shaped struts may not include an eyelet. Moreover, it is to be understood that a fewer or greater number of eyelets can extend from a "V" shaped strut.

The outer frame 1640 can include a set of locking tabs 1652 extending from at or proximate an upper end of the upper region 1642a. As shown, the locking tabs 1652 can extend upwardly from the set of eyelets 1650. The outer frame 1640 can include twelve locking tabs 1652, however, it is to be understood that a greater number or lesser number of locking tabs can be used. The locking tabs 1652 can include a longitudinally-extending strut 1652a. At an upper end of the strut 1652a, the locking tab 1652 can include an enlarged head 1652b. As shown, the enlarged head 1652b can have a semi-circular or semi-elliptical shape forming a "mushroom" shape with the strut 1652a. The locking tab 1652 can include an eyelet 1652c which can be positioned through the enlarged head 1652b. It is to be understood that the locking tab 1652 can include an eyelet at other locations, or can include more than a single eyelet.

The locking tab 1652 can be advantageously used with multiple types of delivery systems. For example, the shape of the struts 1652a and the enlarged head 1652b can be used to secure the outer frame 1640 to a "slot" based delivery system, such as the inner retention member 40 described above. The eyelets 1652c and/or eyelets 1650 can be used to secure the outer frame 1640 to a "tether" based delivery system such as those which utilize sutures, wires, or fingers to control delivery of the outer frame 1640 and the prosthesis 1600. This can advantageously facilitate recapture and repositioning of the outer frame 1640 and the prosthesis 1600 in situ.

The outer frame 1640, such as the outer frame body 1642 can be used to attach or secure the prosthesis 1600 to a native valve, such as a native mitral valve. For example, the intermediate region 1642b of the outer frame body 1642 and/or the outer anchoring feature 1644 can be positioned to contact or engage a native valve annulus, tissue beyond the native valve annulus, native leaflets, and/or other tissue at or around the implantation location during one or more phases of the cardiac cycle, such as systole and/or diastole. As another example, the outer frame body 1642 can be sized and positioned relative to the inner frame anchoring feature 1624 such that tissue of the body cavity positioned between the outer frame body 1642 and the inner frame anchoring feature 1624, such as native valve leaflets and/or a native valve annulus, can be engaged or pinched to further secure the prosthesis 1600 to the tissue. As shown, the inner frame anchoring feature 1624 includes nine anchors; however, it is to be understood that a fewer or greater number of anchors can be used. In some embodiments, the number of individual anchors can be chosen as a multiple of the number of commissures for the valve body 1660. For example, for a valve body 1660 have three commissures, the inner frame anchoring feature 1624 can have three individual anchors (1:1 ratio), six individual anchors (2:1 ratio), nine individual anchors (3:1 ratio), twelve individual anchors (4:1 ratio), fifteen individual anchors (5:1 ratio), or any other multiple of three. In some embodiments, the number of individual anchors does not correspond to the number of commissures of the valve body 1660.

With continued reference to the prosthesis 1600 illustrated in FIGS. 39-40, the valve body 1660 is attached to the inner frame 1620 within an interior of the inner frame body 1622. The valve body 1660 functions as a one-way valve to allow blood flow in a first direction through the valve body 1660 and inhibit blood flow in a second direction through the valve body 1660.

The valve body 1660 can include a plurality of valve leaflets 1662, for example three leaflets 1662, which are joined at commissures. The valve body 1660 can include one or more intermediate components 1664. The intermediate components 1664 can be positioned between a portion of, or the entirety of, the leaflets 1662 and the inner frame 1620 such that at least a portion of the leaflets 1642 are coupled to the frame 1620 via the intermediate component 1664. In this manner, a portion of, or the entirety of, the portion of the valve leaflets 1662 at the commissures and/or an arcuate edge of the valve leaflets 1662 are not directly coupled or attached to the inner frame 1620 and are indirectly coupled or "float" within the inner frame 1620.

With reference next to the outer skirt 1680 illustrated in FIG. 39, the outer skirt 1680 can be attached to the inner frame 1620 and/or outer frame 1640. As shown, the outer skirt 1680 can be positioned around and secured to a portion of, or the entirety of, the exterior of the outer frame 1640. The inner skirt 1690 can be attached to the valve body 1660 and the outer skirt 1680. As shown in FIG. 40, a first end of the inner skirt 1690 can be coupled to the valve body 1660 along portions of the valve body 1660 which are proximate the inner frame 1620. A second end of the inner skirt 1690 can be attached to the lower region of the outer skirt 1680. In so doing, a smooth surface can be formed along under each of the leaflets. This can beneficially enhance hemodynamics by allowing blood to more freely circulate and reducing areas of stagnation.

Although the prosthesis 1600 has been described as including an inner frame 1620, an outer frame 1640, a valve body 1660, and skirts 1680, 1690, it is to be understood that the prosthesis 1600 need not include all components. For example, in some embodiments, the prosthesis 1600 can include the inner frame 1620, the outer frame 1640, and the valve body 1660 while omitting the skirt 1680. Moreover, although the components of the prosthesis 1600 have been described and illustrated as separate components, it is to be understood that one or more components of the prosthesis 1600 can be integrally or monolithically formed. For example, in some embodiments, the inner frame 1620 and the outer frame 1640 can be integrally or monolithically formed as a single component.

From the foregoing description, it will be appreciated that an inventive product and approaches for implant delivery systems are disclosed. While several components, techniques and aspects have been described with a certain degree of particularity, it is manifest that many changes can be made in the specific designs, constructions and methodology herein above described without departing from the spirit and scope of this disclosure.

Certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as any subcombination or variation of any subcombination.

Moreover, while methods may be depicted in the drawings or described in the specification in a particular order, such methods need not be performed in the particular order shown or in sequential order, and that all methods need not be performed, to achieve desirable results. Other methods that are not depicted or described can be incorporated in the example methods and processes. For example, one or more additional methods can be performed before, after, simultaneously, or between any of the described methods. Further, the methods may be rearranged or reordered in other implementations. Also, the separation of various system components in the implementations described above should not be understood as requiring such separation in all implementations, and it should be understood that the described components and systems can generally be integrated together in a single product or packaged into multiple products. Additionally, other implementations are within the scope of this disclosure.

Conditional language, such as "can," "could," "might," or "may," unless specifically stated otherwise, or otherwise understood within the context as used, is generally intended to convey that certain embodiments include or do not include, certain features, elements, and/or steps. Thus, such conditional language is not generally intended to imply that features, elements, and/or steps are in any way required for one or more embodiments.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than or equal to 10% of, within less than or equal to 5% of, within less than or equal to 1% of, within less than or equal to 0.1% of, and within less than or equal to 0.01% of the stated amount. If the stated amount is 0 (e.g., none, having no), the above recited ranges can be specific ranges, and not within a particular % of the value. For example, within less than or equal to 10 wt./vol. % of, within less than or equal to 5 wt./vol. % of, within less than or equal to 1 wt./vol. % of, within less than or equal to 0.1 wt./vol. % of, and within less than or equal to 0.01 wt./vol. % of the stated amount.

Some embodiments have been described in connection with the accompanying drawings. The figures are drawn to scale, but such scale should not be limiting, since dimensions and proportions other than what are shown are contemplated and are within the scope of the disclosed inventions. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

While a number of embodiments and variations thereof have been described in detail, other modifications and methods of using the same will be apparent to those of skill in the art. Accordingly, it should be understood that various applications, modifications, materials, and substitutions can be made of equivalents without departing from the unique and inventive disclosure herein or the scope of the claims.

What is claimed is:

1. A method for delivering an expandable implant to a body location, the method comprising:
   delivering an expandable replacement heart valve within a delivery system toward a location of a native heart valve,
   wherein the expandable replacement heart valve comprises a distal end and a proximal end, wherein the delivery system comprises an outer sheath assembly, a rail assembly, and an inner shaft assembly, wherein the outer sheath assembly comprises an outer shaft having an outer lumen and a capsule configured to retain the expandable replacement heart valve in a radially compressed configuration, wherein the rail assembly is located within the outer lumen of the outer sheath assembly, the rail assembly comprising a steerable rail shaft having a rail lumen and at least one pull wire attached on an inner surface of the rail shaft configured to provide an axial force on the steerable rail shaft to steer the rail assembly, wherein the inner assembly is disposed within the rail lumen of the rail assembly, the inner assembly comprising an inner shaft having an inner lumen and an inner retention member configured to be releasably attached to the expandable replacement heart valve;

activating the at least one pull wire in the rail assembly to provide at least one bend to the steerable rail shaft to steer the delivery assembly toward the location of the native heart valve;

moving the outer sheath assembly and the inner retention member distally together relative to the rail assembly to position the expandable replacement heart valve at the location of the native heart valve while the expandable replacement heart valve remains in the radially compressed configuration within the capsule; and proximally retracting the outer sheath assembly relative to the inner retention member in order to at least partially expand the expandable replacement heart valve from the radially compressed configuration at the location of the native heart valve.

2. The method of claim 1, further comprising activating a second pull wire in the rail assembly to provide a second bend to the steerable rail shaft to steer the delivery assembly toward the location of the native heart valve.

3. The method of claim 1, further comprising moving a mid shaft assembly comprising an outer retention member configured to radially restrain at least a portion of the expandable replacement heart valve distally together with the outer sheath assembly and the inner retention member to position the expandable replacement heart valve at the location of the native heart valve while the expandable replacement heart valve remains in the radially compressed configuration, wherein the mid shaft assembly is located within the outer lumen of the outer sheath assembly and comprises a mid shaft having a middle lumen.

4. The method of claim 1, wherein delivering the expandable replacement heart valve within the delivery system toward the location of the native heart valve comprises advancing the delivery system into an atrium of the heart using a transseptal approach.

5. The method of claim 1, wherein the native heart valve is a native mitral valve.

6. The method of claim 1, wherein the native heart valve is a native tricuspid valve.

7. The method of claim 1, wherein the inner retention member comprises a ring.

8. The method of claim 1, wherein the capsule is positioned at the distal end of the outer sheath and comprises:
an outer polymer layer; and
a metal middle layer located on a radially inner surface of the outer polymer layer;
an inner liner located on a radially inner surface of the middle layer.

9. A method for delivering an expandable implant to a body location, the method comprising:

delivering the expandable implant within an outer sheath assembly of a delivery system toward the body location, the expandable implant having a distal end and a proximal end, wherein the expandable implant is in a compressed configuration within the outer sheath assembly and is releasably retained by an inner retention member positioned at a distal end of an inner shaft assembly;

activating a pull wire attached to a steerable rail shaft of a rail assembly of the delivery system to steer the delivery system, the rail assembly being located within an outer lumen of the outer sheath assembly, wherein activating the pull wire provides at least one bend to the steerable rail shaft to steer the delivery system toward the body location, wherein the inner shaft assembly is positioned within a lumen of the rail assembly;

moving the outer sheath assembly and the inner retention member distally together relative to the rail assembly to position the expandable implant at the body location while the expandable implant remains in a radially compressed configuration within the outer sheath assembly; and proximally retracting the outer sheath assembly relative to the inner retention member in order to at least partially expand the expandable implant from the radially compressed configuration.

10. The method of claim 9, further comprising activating a second pull wire in the rail assembly to provide a second bend to the steerable rail shaft.

11. The method of claim 9, further comprising:
moving a mid shaft assembly located within the outer lumen of the outer sheath assembly and comprising an outer retention member configured to radially restrain at least a portion of the expandable implant distally together with the outer sheath assembly and the inner retention member to position the expandable implant at the body location while the expandable implant remains in the radially compressed configuration.

12. The method of claim 11, further comprising moving a nose cone assembly comprising a nose cone shaft and a nose cone distally together with the outer sheath assembly and the inner retention member to position the expandable implant at the body location while the expandable implant remains in the radially compressed configuration, wherein the nose cone assembly is located within an inner lumen of an inner shaft of the inner shaft assembly.

13. The method of claim 12, further comprising proximally retracting the mid shaft assembly relative to the inner retention member in order to at least partially expand the expandable implant.

14. A method for delivering an expandable implant to a body location, the method comprising:

delivering the expandable implant within an outer sheath assembly of a delivery system toward the body location, the expandable implant having a distal end and a proximal end, wherein the expandable implant is in a compressed configuration within the outer assembly and is releasably retained in the outer sheath assembly by an inner retention member of an inner shaft assembly of the delivery system;

actuating a steerable rail shaft of a rail assembly of the delivery system positioned within the outer sheath assembly to steer the delivery system, the steerable rail shaft having a rail lumen and a proximal end and a distal end, wherein actuating the steerable rail shaft provides at least one bend to the steerable rail shaft to steer the delivery system toward the body location;

moving the outer sheath assembly and the inner retention member distally together relative to the rail assembly to position the expandable implant at the body location while the expandable implant remains in the compressed configuration; and proximally retracting the outer sheath assembly relative to the inner retention member in order to at least partially expand the expandable implant from the compressed configuration at the body location.

15. The method of claim 14, wherein the inner shaft assembly comprises an inner shaft having an inner lumen, wherein the outer sheath assembly comprises an outer shaft having an outer lumen, wherein the rail assembly is located within the outer lumen of the outer shaft, and wherein the inner shaft assembly is located within the rail lumen of the rail assembly.

16. The method of claim 15, further comprising moving a mid shaft assembly comprising an outer retention member configured to radially restrain at least a portion of the expandable implant distally together with the outer sheath assembly and the inner retention member to position the expandable implant at the body location while the expandable implant remains in the compressed configuration, wherein the mid shaft assembly is located within the outer lumen of the outer shaft.

17. The method of claim 15, further comprising moving a nose cone assembly comprising a nose cone shaft and a nose cone distally together with the outer sheath assembly and the inner retention member to position the expandable implant at the body location while the expandable implant remains in the compressed configuration, wherein the nose cone assembly is located within the inner lumen of the inner shaft.

18. The method of claim 17, further comprising proximally retracting the mid shaft assembly relative to the inner retention member in order to at least partially expand the expandable implant.

19. The method of claim 14, wherein actuating the steerable rail shaft comprises activating at least one pull wire in the rail assembly to provide the at least one bend to the rail shaft to steer the delivery system toward the body location.

20. The method of claim 14, wherein the body location is a native mitral valve or a native tricuspid valve.

* * * * *